US012752046B2

(12) United States Patent
Sharma et al.

(10) Patent No.: US 12,752,046 B2
(45) Date of Patent: Oct. 6, 2026

(54) FECAL MANAGEMENT SYSTEMS AND METHODS

(71) Applicant: CM Technologies, Inc., San Diego, CA (US)

(72) Inventors: Amit Kumar Sharma, New Delhi (IN); Nishith Chasmawala, Surat (IN); Geetika Garg, Ghaziabad (IN); Shreyas Dighe, Nagpur (IN)

(73) Assignee: CM Technologies, Inc., San Diego, CA (US)

( * ) Notice: Subject to any disclaimer, the term of this patent is extended or adjusted under 35 U.S.C. 154(b) by 774 days.

(21) Appl. No.: 17/881,252

(22) Filed: Aug. 4, 2022

(65) Prior Publication Data

US 2022/0379001 A1 Dec. 1, 2022

Related U.S. Application Data

(63) Continuation-in-part of application No. 17/444,430, filed on Aug. 4, 2021, now Pat. No. 11,628,085.

(30) Foreign Application Priority Data

Aug. 4, 2020 (IN) ............................ 202011033387

(51) Int. Cl.
*A61M 1/00* (2006.01)
*A61B 10/00* (2006.01)
(Continued)

(52) U.S. Cl.
CPC ........... *A61M 1/77* (2021.05); *A61B 10/0038* (2013.01); *A61F 5/4405* (2013.01); *A61M 1/74* (2021.05);
(Continued)

(58) Field of Classification Search
CPC ........ A61F 5/44; A61F 5/4405; A61F 5/4407; A61F 5/451; A61M 1/77; A61M 1/74;
(Continued)

(56) References Cited

U.S. PATENT DOCUMENTS 3,349,768 A 10/1967 Xavier
3,511,241 A 5/1970 Lee
(Continued)

FOREIGN PATENT DOCUMENTS

BG 1571657 A 7/1980
EP 0032138 B1 11/1984
(Continued)

*Primary Examiner* — Jessica Arble
*Assistant Examiner* — Nhu Q. Tran
(74) *Attorney, Agent, or Firm* — Budzyn IP Law, LLC

(57) ABSTRACT

Fecal management methods and apparatuses (e.g., devices, systems, etc.) are described herein. The fecal management apparatuses may apply one or more fecal removal cycles of suction and irrigation (and in some examples air) to actively remove fecal material. The apparatus may control the timing of delivery of the fecal removal cycles as well as the parameters of the applied suction, irrigation and/or air within and between fecal removal cycles. The invention additionally provides methods, and computer program products for controlling an apparatus or system that is configured for removal of fecal material from a patient's rectum.

19 Claims, 24 Drawing Sheets

(51) Int. Cl.
*A61F 5/44* (2006.01)
*A61M 3/02* (2006.01)

(52) U.S. Cl.
CPC ............ *A61M 1/85* (2021.05); *A61M 3/0202* (2021.05); *A61M 3/0258* (2013.01); *A61M 2210/1067* (2013.01)

(58) Field of Classification Search
CPC .... A61M 1/85; A61M 3/0202; A61M 3/0258; A61M 2210/1067; A61M 1/772; A61M 2205/8206; A61M 2209/082; A61M 3/0266; A61M 3/0283; A61M 3/0287; A61B 10/0038; A61B 1/015; A61B 1/31; A61B 2017/22037
See application file for complete search history.

(56) References Cited

U.S. PATENT DOCUMENTS 3,512,185 A 5/1970 Ellis
3,881,486 A 5/1975 Fenton
4,020,843 A 5/1977 Kanall
4,022,213 A 5/1977 Stein
4,084,589 A 4/1978 Kulvi
4,178,934 A 12/1979 Forman
4,246,901 A 1/1981 Frosch et al.
4,257,418 A 3/1981 Hessner
4,281,655 A 8/1981 Terauchi
4,387,726 A 6/1983 Denard
4,457,314 A 7/1984 Knowles
4,466,888 A 8/1984 Verkaart
4,622,981 A 11/1986 Sherlock
4,625,734 A 12/1986 Sherlock et al.
4,637,814 A * 1/1987 Leiboff ............... A61M 3/0283 604/27
4,692,160 A 9/1987 Nussbaumer
4,747,166 A 5/1988 Kuntz
4,795,449 A 1/1989 Schneider et al.
4,799,928 A 1/1989 Crowley
4,804,377 A 2/1989 Hanifl et al.
4,842,583 A * 6/1989 Majlessi ............. A61M 3/0283 604/275
4,886,508 A 12/1989 Washington
4,889,533 A 12/1989 Beecher
4,941,878 A 7/1990 Petrik
5,141,504 A 8/1992 Herweck et al.
5,300,052 A 4/1994 Kubo
5,401,262 A 3/1995 Karwoski et al.
5,735,837 A 4/1998 Ishikawa
5,827,257 A 10/1998 Fujioka et al.
6,129,715 A 10/2000 Cunningham
6,311,339 B1 11/2001 Kraus
6,464,674 B1 10/2002 Palumbo et al.
6,530,909 B1 3/2003 Nozaki et al.
6,569,133 B2 5/2003 Cheng et al.
6,585,720 B2 7/2003 Lapcevic
6,635,038 B2 10/2003 Scovel
6,732,384 B2 5/2004 Scott
6,857,137 B2 2/2005 Otto
7,022,101 B2 * 4/2006 Xu ........................ A61M 31/00 604/28
7,186,245 B1 3/2007 Cheng et al.
7,390,320 B2 6/2008 Machida et al.
7,755,497 B2 7/2010 Wada et al.
7,927,320 B2 4/2011 Goldwasser et al.
8,287,508 B1 10/2012 Sanchez
8,303,554 B2 11/2012 Tsai et al.
8,357,105 B2 1/2013 Fontaine et al.
9,788,992 B2 10/2017 Harvie
10,064,774 B2 9/2018 Onoda
RE47,285 E * 3/2019 Loske ................... A61M 1/916
10,226,376 B2 3/2019 Sanchez et al.
10,376,406 B2 8/2019 Newton
10,376,407 B2 8/2019 Newton
10,390,989 B2 8/2019 Sanchez et al.
10,857,025 B2 12/2020 Davis et al.
10,952,889 B2 3/2021 Newton et al.
10,973,678 B2 4/2021 Newton et al.
11,207,206 B2 12/2021 Sharma et al.
11,253,389 B2 2/2022 Sharma et al.
2002/0087131 A1 7/2002 Wolff et al.
2003/0163120 A1 8/2003 Harvie
2004/0006321 A1 1/2004 Cheng et al.
2004/0039348 A1 * 2/2004 Kim .................... A61M 3/0262 604/523
2005/0256464 A1 * 11/2005 Pallas ............ A61B 17/320708 604/319
2006/0025729 A1 * 2/2006 Leiboff ................. A61M 3/022 604/317
2006/0111681 A1 5/2006 Vernon
2006/0173244 A1 * 8/2006 Boulais .................. A61B 1/015 600/156
2006/0218709 A1 10/2006 Langford
2006/0253091 A1 11/2006 Vernon
2008/0004560 A1 1/2008 Miskie
2008/0091153 A1 4/2008 Harvie
2008/0178377 A1 7/2008 Liu
2008/0281284 A1 11/2008 Garfield et al.
2009/0143722 A1 * 6/2009 Kim ...................... A61M 3/022 604/28
2009/0193571 A1 * 8/2009 Nakamura ............... A61G 9/00 4/300
2009/0270910 A1 10/2009 Hargens et al.
2010/0063436 A1 * 3/2010 Tanghoej ............ A61M 3/0208 604/27
2010/0160881 A1 6/2010 Lin et al.
2010/0256447 A1 * 10/2010 Dubi .................. A61B 1/00135 600/115
2010/0268154 A1 10/2010 Vining
2010/0298773 A1 * 11/2010 Nitsan ................. A61M 3/0283 604/150
2010/0298789 A1 11/2010 Santimaw
2011/0022011 A1 1/2011 Edward
2011/0060300 A1 3/2011 Weig et al.
2011/0092892 A1 * 4/2011 Nitsan ................ A61B 1/00068 604/524
2011/0282311 A1 * 11/2011 Nishtala ................ A61F 5/4405 604/332
2012/0029485 A1 * 2/2012 Tan ..................... A61M 3/0287 604/540
2012/0103347 A1 5/2012 Wheaton et al.
2012/0116336 A1 5/2012 Sharma et al.
2012/0233761 A1 9/2012 Huang
2013/0085442 A1 * 4/2013 Shtul ...................... A61B 1/126 604/28
2014/0005479 A1 * 1/2014 Loske ................... A61M 1/916 600/156
2014/0157499 A1 6/2014 Suzuki et al.
2014/0182051 A1 7/2014 Tanimoto et al.
2014/0276494 A1 9/2014 Cisko et al.
2015/0135423 A1 5/2015 Sharpe et al.
2016/0051395 A1 2/2016 Ugarte
2016/0206805 A1 * 7/2016 Hassidov ................ A61M 1/77
2016/0317000 A1 * 11/2016 Hassidov ............... A61B 1/018
2016/0367226 A1 12/2016 Newton et al.
2017/0000642 A1 1/2017 Cisko et al.
2017/0007438 A1 1/2017 Harvie
2017/0042724 A1 2/2017 Ugarte
2017/0087284 A1 * 3/2017 Shtul ................... A61M 3/0279
2017/0252202 A9 9/2017 Sanchez et al.
2017/0304526 A1 * 10/2017 Jo ....................... A61M 3/0216
2017/0312405 A1 11/2017 Newton
2019/0038451 A1 2/2019 Harvie
2019/0247222 A1 8/2019 Ecklund et al.
2019/0247566 A1 8/2019 Hassidov et al.
2019/0343445 A1 11/2019 Burnett et al.
2019/0365561 A1 12/2019 Newton et al.
2020/0037832 A1 * 2/2020 Wang ...................... A61F 5/451
2020/0046544 A1 2/2020 Godinez et al.
2020/0085610 A1 3/2020 Cohn et al.
2020/0093977 A1 * 3/2020 Hassidov ............ A61M 3/0283
2020/0315838 A1 10/2020 Eckert

(56) References Cited

U.S. PATENT DOCUMENTS

| | | | | |
|---|---|---|---|---|
| 2020/0390591 | A1 | 12/2020 | Glithero et al. | |
| 2021/0069008 | A1 | 3/2021 | Blabas et al. | |
| 2021/0093157 | A1* | 4/2021 | Lichtenstein ...... | A61B 1/00154 |
| 2021/0113130 | A1 | 4/2021 | Tran | |
| 2022/0040395 | A1 | 2/2022 | Sharma et al. | |

FOREIGN PATENT DOCUMENTS

| | | | |
|---|---|---|---|
| GB | 2260907 | B | 5/1995 |
| JP | H08117329 | A | 5/1996 |
| WO | 199309736 | A2 | 5/1993 |
| WO | 2004026194 | A1 | 4/2004 |
| WO | 2007005851 | A2 | 1/2007 |
| WO | 2016103242 | A1 | 6/2016 |
| WO | 2019212949 | A1 | 11/2019 |
| WO | 2019212950 | A1 | 11/2019 |
| WO | 2019212951 | A1 | 11/2019 |
| WO | 2019212955 | A1 | 11/2019 |
| WO | 2019212956 | A1 | 11/2019 |
| WO | 2021231532 | A1 | 11/2021 |
| WO | 2021231724 | A1 | 11/2021 |

* cited by examiner

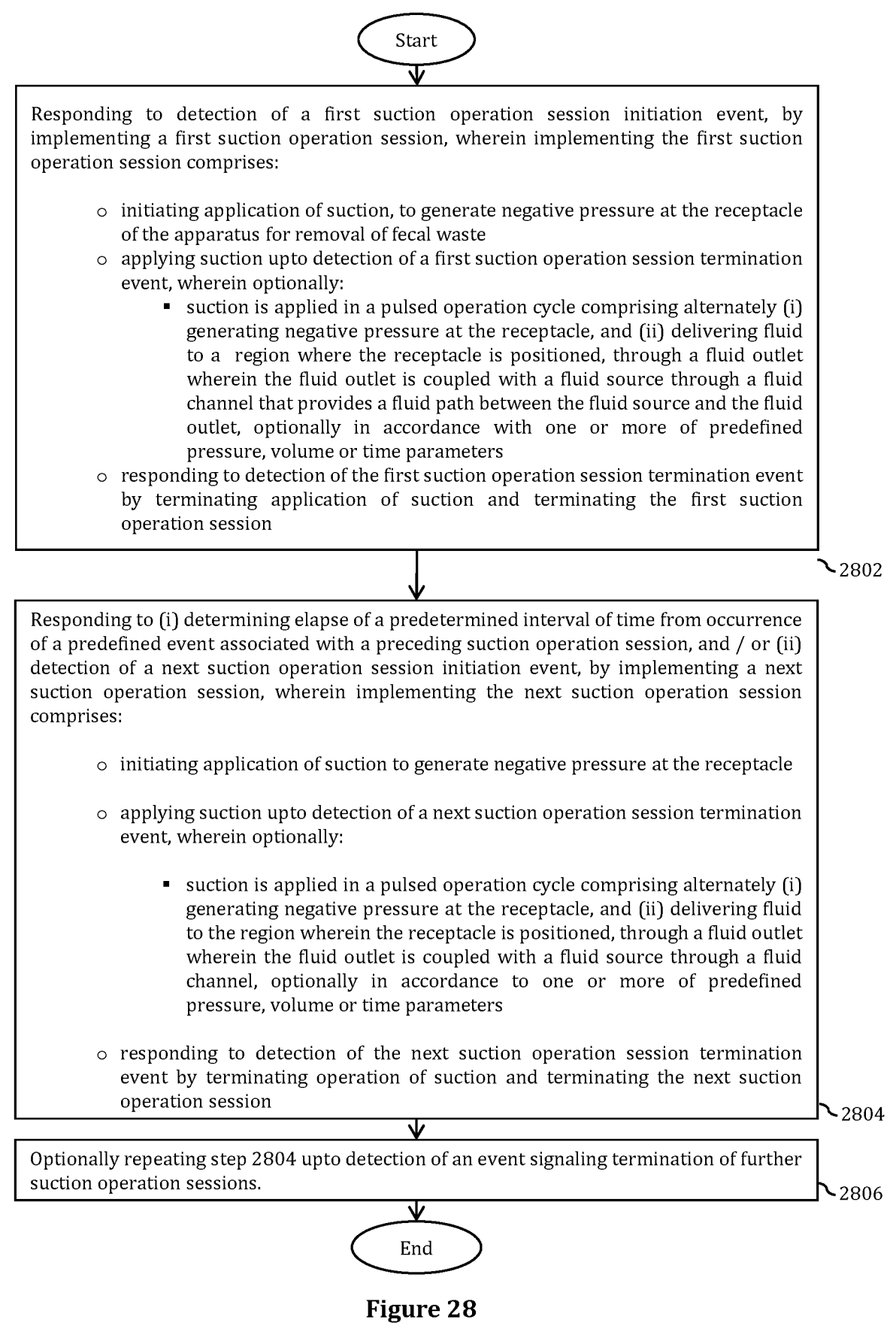

Start

Responding to detection of a first suction operation session initiation event, by implementing a first suction operation session, wherein implementing the first suction operation session comprises:

- initiating application of suction, to generate negative pressure at the receptacle of the apparatus for removal of fecal waste
- applying suction upto detection of a first suction operation session termination event, wherein optionally:
    - suction is applied in a pulsed operation cycle comprising alternately (i) generating negative pressure at the receptacle, and (ii) delivering fluid to a region where the receptacle is positioned, through a fluid outlet wherein the fluid outlet is coupled with a fluid source through a fluid channel that provides a fluid path between the fluid source and the fluid outlet, optionally in accordance with one or more of predefined pressure, volume or time parameters
- responding to detection of the first suction operation session termination event by terminating application of suction and terminating the first suction operation session

2802

Responding to (i) determining elapse of a predetermined interval of time from occurrence of a predefined event associated with a preceding suction operation session, and / or (ii) detection of a next suction operation session initiation event, by implementing a next suction operation session, wherein implementing the next suction operation session comprises:

- initiating application of suction to generate negative pressure at the receptacle
- applying suction upto detection of a next suction operation session termination event, wherein optionally:
    - suction is applied in a pulsed operation cycle comprising alternately (i) generating negative pressure at the receptacle, and (ii) delivering fluid to the region wherein the receptacle is positioned, through a fluid outlet wherein the fluid outlet is coupled with a fluid source through a fluid channel, optionally in accordance to one or more of predefined pressure, volume or time parameters
- responding to detection of the next suction operation session termination event by terminating operation of suction and terminating the next suction operation session

2804

Optionally repeating step 2804 upto detection of an event signaling termination of further suction operation sessions.

2806

End

Figure 28

FECAL MANAGEMENT SYSTEMS AND METHODS

CROSS-REFERENCE TO RELATED APPLICATION

This application is a continuation-in-part of U.S. patent application Ser. No. 17/444,430, filed Aug. 4, 2021, now pending, which claims priority to Indian Patent Application No. 202011033387, filed Aug. 4, 2020, the entire contents of which are incorporated by reference herein.

BACKGROUND

Fecal incontinence (FI), the inability to control the release of the flatus or stool causing involuntary leakage, is a clinical problem that is commonly encountered by gastrointestinal physicians and care providers the world over. Ranging in severity from minor soiling to a complete loss of bowel control, FI is a psychologically distressing condition that significantly affects quality of life. There is a list of abnormalities that causes FI and depending upon the underlying causes, treatment method differs in a variety of clinical solutions. These clinical solutions for fecal incontinence can be classified in four main categories: pharmacological, containment or management, electro-muscular stimulation, and surgical restoration of the anorectal neuro-muscular apparatus. All containment and management options, to a varying degree, result in complications such as incontinence-associated dermatitis, maceration, constipation, impaction, moisture associated pressure injuries, ulceration, catheter associated urinary tract infection, blood stream infection, and sepsis. Other secondary complications include necrosis, sphincter dysfunction, anal erosion, patient discomfort, trauma, or bleeding, which may arise from the use of a pad, pouch or an indwelling catheter. Such outcomes increase the length of hospitalization, significantly add to the cost of care, reduce the Quality of Life and increase the mortality rate. The primary complications are mainly attributed to the fact that the fecal output in patient, once it has exited the anal canal, continues to remain there until it is physically removed by way of cleaning using a washcloth, fluid flush, change of containment layer (diaper, pad), milking of catheters or removal of pouch.

One must also draw a key difference in managing fecal material before, during and after the defecation process. A patient may have presence of fecal material within their rectum, but the process of defecation is initiated by the physiological process of peristaltic contractions. The normal position of the rectum is to remain contracted. Only changes in intra-rectal pressures and build-up of feces in the rectal vault, causes the rectum to expand and eventually open up for the process of defecation.

The majority of currently available fecal management solutions include non-powered products like absorbent pads or diapers, adhesive collection pouches, and indwelling collection catheters. Although powered products that use negative pressure to vacuum out defecated stool into a collection chamber are known, they also incur a number of undesirable complications. Continuous and unregulated use of vacuum suction to manage fecal material may force the rectum to remain collapsed interfering with normal flow of blood in the capillaries surrounding the ano-rectal apparatus. Continuous and unregulated use of vacuum suction may also alter the moisture levels leading to excessive dehydration of both the anorectal anatomy as well as the feces of the patient. Outside of the patient's body, the use of negative pressure, requires the apparatus to be made of rigid components and airtight containers. Both of these are challenging in a clinical setting as they could injure the patient's anatomy or interfere in care-providers work-flow. Furthermore, all current solutions for fecal management, non-powered or powered, are passive solutions that depend on the user to defecate first.

Described herein are method and apparatuses for managing fecal exudate (e.g., stool) in patients. These methods and apparatuses may use a vacuum, i.e. a negative pressure source or a positive pressure source to actively manage fecal material in a patient before, during or after the process of defecation has been initiated by the body, with minimal input from the care-provider.

SUMMARY OF THE DISCLOSURE

Described herein are fecal management methods and apparatuses (e.g., devices, systems, etc.). The apparatuses described herein for managing fecal waste (e.g., stool) may be referred to as active management solutions, or active stool management solutions. These methods and apparatuses do not depend on a patent defecation process but may collect stool from within the patient's (e.g., user's, subject's, etc.) rectum and may transfer it to a collection chamber (e.g., external collection bag or canister) in a closed-loop, odor free, and hygienic manner. These apparatuses and methods may be considered as methods and systems for containment or management of fecal output. Typical fecal containment or management systems may include one or combination of absorbent pads (in the form of pads), diapers, sanitary napkins, anal plugs (also known as anal tampons), fecal collectors in form of collection bags or pouches and/or indwelling catheters.

The methods and apparatuses described herein may include a vacuum-assisted fecal incontinence management device to autonomously evacuate liquid and semi-formed fecal effluents in bed ridden patients and contain them in an odor-proof collection bag. These devices may apply a softening/loosening material (such as a fluid, including in particular, water) that may be controllably applied by the apparatus (and/or as part of the method). The method or system may also include suction, e.g., the application of negative pressure, which may be generated by a portable pump that may be housed in apparatus. This pump may be powered by a battery (a rechargeable battery) and may be controlled by a controller (e.g., a microcontroller). The battery and/or controller may be housed in the apparatus, which may be configured as a canister. The negative pressure generated by the pump may be applied to patient rectum via a soft, universal receptacle. The apparatus may be programmed to activate periodically, assess the state of rectal contents, and apply a combination of negative pressure (suction) along with a stream of air, water or both, to suction out the rectal effluent material into a collection chamber and/or a collection chamber. The collection chamber may be a single or multiple use external collection chamber (e.g., "collection bag" or "collection canister"). In some examples negative pressure and/or positive pressure may be used to push out the rectal effluent material from the rectum to the external collection chamber. In any of these apparatuses, the apparatus may deliver positive pressure inside the rectum by pumping in air or CO2 which will then push the stool out through the transit tube into a collection bag. Thus the controller may inject positive pressure.

Thus, in general, the methods and apparatuses described herein facilitate the collection of fecal material before, after or in combination with the natural defecation process of the subject (e.g., patient, user, etc.), without interfering with the anorectal anatomy/physiology, causing any discomfort to the patients or altering the flow of nursing treatment. For example, an apparatus as described herein may include components that work together and provide an effective way to manage fecal waste that is safe, efficacious and beneficial to patients and care providers alike.

In general, any of these apparatuses may include a receptacle interfacing with the subject's rectum, connecting tubing coupling the receptacle to a control unit, which may be housed within a housing (e.g., a cannister) and an external collection chamber (e.g., collection bag). The control unit (also referred to herein as a "master control unit") may include a controller with one or more processors, memory, circuitry for controlling one or more pumps, one or more valves, and/or one or more sensors. The control unit may include or be coupled to a pump or pumps or external source doing the function of the said pump or pumps. A power source (e.g., battery or other power source) may be housed within the housing along with a pump or pumps or may be external to the housing. The apparatus may include a reservoir for fluid (e.g., water) and/or a connection (e.g., tubing) to an external source of fluid. The apparatus may also include a secure coupling to an external collection chamber for collecting the stool and/or other waste (including waste fluid). The apparatus may also include one or more outputs, such as a display, LEDs, etc. The apparatus may also include one or more inputs (e.g., buttons, controls, knobs, etc.) for user (e.g., physician, nurse, technician, caregiver, etc.) selected inputs (e.g., turning the device on, selecting the pre-programmed setting, setting a use profile, etc.). The apparatus may also include one or more outputs that act as alerts, such as sonic (e.g. tone, alarms, etc.) and/or visual alerts (lights, etc.). In some examples the apparatus may include one or more communications circuits for communicating, including wireless communicating with a remote server or patient monitoring station and/or user communication device (e.g., phone, tablet, etc.). The apparatus may transmit data regarding the status of the device (in use, disabled, in need of bag change, fluid reservoir fill level, and/or error codes).

For example, a receptacle may be a collection structure that is configured to be applied to the patient anatomy and has the ability to collect and/or direct fecal material. The receptacle can be on either side of or within the anal canal, and/or inside the rectum. For example, the receptacle may be configured to be positioned near, or in certain embodiments, external to the patient's body but affixed to either the anal opening, perineum, buttocks or all of the above. The receptacle may collect, contain and facilitate the diversion of fecal material using vacuum suction or negative pressure, without causing erythema, necrosis, ulceration, dysfunction, erosion, dermatitis, maceration, etc. The receptacle may be firm, absorbable, lubricious, flow-directing, compliant, biocompatible to derma, mucosa, blood and sub-cutaneous contact, etc. In some examples the receptacle may be funnel-shaped, and may couple at the proximal end to the connecting tube.

The receptacle can be applied to the anatomy in a variety of different ways for the purpose of collecting and diverting fecal material. The receptacle may be applied external to the body and may be secured using one or more: of adhesive, straps, gravity reliant flat pads, wrap-around garments, or two-way attachment mechanisms like Velcro, double-sided tapes, magnets or crystalizing/fast cure chemicals. In some examples, especially when the receptacle is held within the patient's body or on the anal verge, application may involve finger (digital) insertion or insertion with the aid of one or more mechanical construct that may include a mechanism to push, pull, twist, rotate, peel, and/or slide the receptacle for delivery. The insertion (including digital insertion) may involve one or more mechanism in which activation is triggered by an external device. Thus, the receptacle may be configured for delivery by one or more applicators which may include, for example but not limited to, applicators including an inflation mechanism, telescoping mechanism, irising mechanism, ratcheting mechanism linear screw mechanism, etc.

The receptacle may be configured for external application and may be secured at least in part by a securing mechanism configured in various shapes like circular, horse-shoe shaped (U), cross U shape where both vertical arms overlap, oval and other shape that contours along the pelvic-buttock anatomy. The receptacle may include a material such as a derma friendly tapes, adhesives, hydrocolloid/colloids, silicon-based adhesives that can be used over follicles, breathable, moisture absorbing, fluid channeling, material designed with modified surface properties, that may facilitate the anchoring and affixation of the receptacle. The receptacle itself may facilitate the collection and diversion of fecal material. The receptacle may be formed of any biocompatible material, including biocompatible polymers (e.g., silicone, polyurethane, polyvinyl chloride, etc.).

Fecal matter generally discharged from the colon into the rectum and is then expelled from the body by a wave-like muscular contraction of the colon and rectal walls (peristalsis) and a corresponding relaxation of the puborectalis muscle and sphincter. Peristaltic contractions cause the rectal walls to expand and contract to move fecal matter towards the anal opening.

The receptacle in any of these variations may be coupled to a vacuum source. A pre- or self-calibrated vacuum pressure may thus be created over a pre- or self-determined period of time, in order to divert fecal material, before, during or after the defecation process, out through the receptacle. The negative pressure (vacuum or suction) may be calibrated so that it does not significantly collapse the colorectal anatomy, dehydrate the colorectal apparatus, or cause any injury, trauma or foreign body sensation to the patient. In general, the apparatus may account for the anatomy and physiology of the rectum and anal canal. The anorectal junction (the boundary between rectum and anal canal) provides a limiting boundary for particular nerve types. Visceral nerves are found above the anorectal junction (towards the rectum), while somatic nerves are found below the said junction (towards the anal canal). Somatic nerves are capable of sensing pain, while visceral nerves only sense pressure and not pain. Because of the presence of somatic nerves, the portion between anorectal junction and anal verge is extremely sensitive and can cause a high level of discomfort when pressure (e.g., vacuum or other similar forces) is applied, and/or if a large bore, rigid object is placed within the anal canal or at the anorectal junction.

Thus, the apparatuses described herein may apply the vacuum to the receptacle at a location such that vacuum conduit is flush with a distal most point of the receptacle, and/or the vacuum forces are diffused and directed by the receptacle such pain, discomfort (or injury) at the anorectal apparatus is avoided. The applicators described herein may be configured to distribute the vacuum applied.

Any appropriate vacuum source may be used. For example, a vacuum source may be configured to be in-line, and programmed to a pre- or self-determined pressure, frequency and amplitude. In some examples the apparatus may be configured to operate off of an external vacuum source, rather than rely on a pump or other included source of suction. Thus, the apparatus may include an adapter for use with a separate source of negative pressure (e.g., suction or vacuum). In some examples the apparatus is configured to use a source of "wall" vacuum, so that the vacuum source used is a central source within the healthcare facility, or other external source. Source of negative pressure may include suction that is due to one or all of, a cylinder, plunger, piston, bellow, squeeze ball, or suction created by a chemical reaction or absorption. The suction adapter may include one or more valves (including a bleed valve), constrictor valve, etc. and/or a manifold and one or more sensors (pressure sensors, flow sensors, etc.) for adapting a pressure from a source of negative (or in some examples, positive) pressure.

Any of the apparatuses and methods descried herein may include irrigation and therefore control the application of a fluid (e.g., water) from a source of irrigation fluid. Alternatively, or additionally gas (air) may be applied. Thus, in addition to the use of vacuum, or negative pressure for the management of fecal material, the apparatus may also apply additional fluid, such as water, to liquefy the stool and/or to hydrate the rectum. A lack of hydration may lead to problems in defecation. In the normal case, as stool moves towards the rectum moisture is absorbed by the colon and the rectum. While this natural process does not typically dehydrate the anatomy, in some cases dehydration may arise because of one or more comorbidities, such as therapeutic dosages and changes in intra-rectal pressures caused by internal or external triggers (including the application of negative pressure) may dehydrate the anatomy and impact patient pathophysiology.

Thus, the methods and apparatuses described herein may include a fluid source that hydrates the stool and well as anorectal anatomy by delivering fluid, in the form of a stream, jet, spray, mist or vapor, which may be delivered in continuous, pulsating, or intermittent form, e.g., via a dedicated conduit that may be connected to a fluid reservoir (e.g., within the housing of the apparatus or coupled to the housing). Fluid movement down connecting tube from the housing (e.g., cannister) to the receptacle may be driven by natural forces (like gravitational or capillary) or may be mechanized (e.g., pumped) or a combination of these. Similar to vacuum delivery, the fluid delivery may be based on a pre- or self-determined volume, frequency and location to hydrate the anatomy without interfering in any anorectal physiology.

The application of fluid may also help to soften and remove material (fecal material) from within the rectum. The use of fluid, in conjunction with vacuum, may also enable the apparatus to divert fecal material that is otherwise difficult to collect, including fecal material that is harder on the Bristol scale. As the patient's overall clinical condition improves, their stool hardens which may be a positive development for the patient. However, most indwelling fecal management devices are rendered non-functional once the stool changes from a Bristol 6-7 to a Bristol 5 or lower. The apparatuses described herein are able to divert fecal material from virtually any consistency including Bristol 7 and lower.

The addition of fluid through the apparatus, including from out of the receptacle, may be configured to flow in a pre- or self-determined pattern, location and pressure within the patient's anatomy. The additional of fluid may also be configured to assists in ensuring that no or minimal residual fecal material is left stationary anywhere in the rectum or the device and facilitates in containing the malodor emanating from the transfer conduit. In some examples, the applied fluid may be applied near the opening(s) of the receptacle so that fluid may be used to help wash of flush the fecal material, including harder fecal material, through the receptacle and connection tubing and ultimately in the external collection chamber (e.g., collection bag). In general, the external collection chambers described herein may be referred to as collection canister or collection bag.

The receptacle may include one or more conduit that may pass from the anal canal into the collection tubing. In general, the anal canal is about 25-50 millimeters in length and is supported by internal and external sphincter muscles. In a healthy individual, internal diameter of anal canal in its resting state is close to zero, but it can distend to about 30 millimeters in diameter to facilitate the outward purge of fecal material and flatulence. The receptacle may therefore be configured to include a soft, compliant, sheath or tube (in examples, may be a lay-flat) that is configured to traverse through the anal canal without eroding the canal or causing any injury, and may limit foreign body sensation to the patient.

Thus, the receptacle and/or connecting tube may form a conduit that houses independent channels to deliver vacuum pressure and the fluid. The conduit may be configured so as to not easily collapse under vacuum, thereby preventing a vacuum lock in the system, and also so as to not cause any erosion of the anal canal. In some examples the apparatus includes a sheath or lay-flat or tube that may be braided, webbed, have surface indentation(s), may include specialized material(s) or other features that provide column strength to prevent the collapse. In some examples, the conduit can be a co-extruded lumen that is optimized for space and sensitivity to the anatomy, and/or may have secondary braiding or molded features along the length to create micro-corrugated structure, and may be made of material that is lubricious, may have a pre-determined tensile strength, may be amorphous or non-amorphous, and may be biocompatible.

The connecting tube, which may form a transit conduit, may start approximately after the anal opening, and may rest between the legs of the patient. The receptacle may be separate from and connected/coupled to the connecting tube, or in some examples it may be continuous with the connecting tube. The distal end of the connecting tube may be fluidly connected with a source of vacuum (negative pressure) and source of fluid (e.g., the irrigation fluid). The apparatus may therefore include one or more conduit that houses the independent channels to deliver fluid and vacuum pressure. The conduit may be configured so as to resist collapse under vacuum (e.g., under negative pressure of 15 mmHg, 100 mmHg, 200 mmHg, 300 mmHg, 500 mmHg, 600 mmHg, 700 mmHg, 800 mmHg, etc. or more), thereby preventing a vacuum lock in the system. The conduit may be configured to prevent injury to the patient from scrapping, rough edges, hard features or excessive moisture wicking properties. For example, the conduit (e.g., connecting tubing and/or receptacle) may be smoot and rounded, preventing or minimizing sharp edges.

In some examples the conduit may be supported by a non-absorbent pad or sleeve to help wick away any moisture that may build up around the anal opening, buttocks or the larger perineal region, to absorb any leakage of bodily secretions from the anal canal. This non-absorbent pad (e.g., sleeve, etc.) may be configured to provide an easier (in terms of ergonomics and physical effort) method to change the receptacle and/or connecting tube as compared to an absorbent pad or a diaper. The conduits (e.g., connecting tubes) described herein may also or alternatively be configured to have an interface for a port to allow the collection of a stool sample. The sampling port can be configured to be operated via aspirating, scooping, squeezing, or diverting desired volume of stool sample from the transit conduit. The sampling port may include one or more mechanisms that support one-way movement of fluid, like flutter valve, duckbill valve, vacuum assist chambers, fluid pushed reservoirs, etc. The sampling port may be before or part of the housing (e.g., canister) portion.

Also described herein are apparatuses including one or more analytic outputs or sensors. For example, any of these apparatuses may be configured to perform or allow visualization of fecal material, including but not limited to recording output volume, discharge frequency, stool consistency, stool color, and/or confirming or identifying the presence of blood or other bio-markers in the stool. The apparatuses, including the conduits described herein may be configured for sensing or measuring properties of the collected stool in a non-contact manner, e.g., though the collecting tube, receptacle, collecting bag, etc. For example, the apparatus may include one or more regions of amorphous and crystalline polymers that may provide a combination of opaque, transparent, and translucent conduit. Materials such as PVDC, EVOH and other similar acetates and chlorides may be used to allow sensing or sampling of properties of the stool without contacting the stool. Any of these apparatuses may be used in conjunction with carbon or charcoal based filters, and with or without the use of negative or positive pressure to prevent the escape of malodorous materials (fecal matter) from the apparatus.

Any of these apparatuses may also of alternatively include or communicate with an output, including an interface that may act as a main communication hub for the users (e.g., nurses, caregivers, physicians, technicians, etc.).

In general, the apparatus may interface via a dedicated port for connection between the components, such as where the conduit (e.g., connecting tube) attaches to the vacuum source and/or controller, as described above. The connection may include a connection mechanism like snap fit, interference fit, friction fit, screwed, clipped on, or by way of various temporary adhesion and securing mechanism. In some examples the interface may include a dedicated port where the transit conduit (connecting tube) attaches to a fluid pump (irrigation source), as described, e.g., via connection mechanisms like Leur locks, snap fit, interference fit, friction fit, screwed, clipped on, or by way of various temporary adhesion and securing mechanism. The interface can be a rigid, semi-rigid, flexible, opaque and/or transparent interface and may be sized so that an in-line vacuum source, a fluid pump, a power source, and electronics that support either solid state or electromechanical relays, are housed together. The interface may include an external on/off switch, a visual display and other connection paraphernalia to further connect the vacuum and fluid source and a multi-chamber construct, with differential pressure, to house a bag or a container for collection and disposal of fecal material.

Any of the apparatuses described herein may include a manifold of (or connected to) a vacuum source within the interface. This manifold may help manage flatulence and odor from within the system. The manifold may include one or more filters, including carbon, charcoal, and other filters, which may be arranged in conjunction with other soft or hard structures to neutralize odor before releasing to the environment.

The apparatuses described herein may also include one or more electromechanical and solid-state relays, configured as pre- or self-programmed or programmable relays that may perform an electromechanical function, and may coordinate the operation and function of the apparatus, and in some examples may coordinate operation with the subject's natural GI motility, which may minimize disruption of the physiology of the subject's normal anorectal physiology. For example, solid state relay(s) may be included and programmed to create a defined sequence of injecting fluid inside the anatomy, generating negative/vacuum pressure throughout the device, reinjecting fluids and creating a negative pressure once more, such that this sequence is replicated and repeated in a precise and accurate manner for as long as the apparatus is in use. Periods of off- or standby-time may be included between one or more cycles of injection fluid and removing material (applying suction). The same process can be reset and repeated any number of times with a steady source of power to the Interface.

In some examples the apparatus can be re-programmed and customized to the clinical needs, or preferences, of the patient. A combination of programmable logic circuit, independent or in conjunction with hard wired programmable tools, or over WiFi or by using Bluetooth connectivity function may be used.

The apparatuses described herein may calibrate the flow of fluids and suction that does not interfere in GI motility, physiology of the anorectal anatomy and to avoid any trauma, pain and discomfort for the patient in the discharge and collection of fecal material by means of vacuum. For example, the apparatus may be configured such that a precise amount of fluids (saline, distilled water, tap water, etc., so any combination of these which may be mixed with a therapeutic or wellness substrates, such as a drug) may be discharged at a pressure no greater than some maximum threshold (e.g., 0.1 psi, 1 psi, 2 psi, 3 psi, 4 psi, 5 psi, 10 psi, 50 psi, etc.), at a fixed or variable, pre- or self-programmed interval and in sequence thereof, to maintain an adequate level of hydration, evacuation force and hygiene inside the anatomy. In addition to fluid flush, vacuum force (suction) of between about 1-500 mm of Hg below atmospheric pressure may be applied for a certain interval. The suction may be variable (including may be ramped up and/or pulsatile) or constant, or a combination of these. In some examples a lower vacuum force may be applied immediately before or after full vacuum force is applied to completely evacuate fecal material from the receptacle to a collection container. The specific force range and duration may be optimized to accommodate variation in stool consistency (e.g., Bristol 7 or lower) and loss of vacuum pressure between the source, receptacle, collection chamber and connectors in between.

Any of these apparatuses may include a housing, which may be configured as a canister, that includes an interface that connects to a transit conduit and one or more irrigation channels. The housing (canister) may house a vacuum pump or may be adapted to couple with (and control) an external vacuum source and/or an interface to vacuum source. The housing may enclose a fluid delivery pump or may be configured to interface to fluid source. The housing may enclose a power source or an interface to power source and associated electronics (e.g., a battery, capacitor, power control circuitry, etc.). The housing may also enclose or partially enclose an intermediary collection chamber (also referred to herein as a stool collection chamber of stool collection cannister) that houses the diverted fluid material (waste, including fecal matter) while the vacuum source is in operation. The housing may enclose or couple with a disposable or reusable collection chamber and/or a fluid reservoir. The housing may also enclose or couple with one or more mechanisms (e.g., valves, channels, sensors, etc.) to regulate the flow of fluid in pre-determined direction, including one or more connectors and conduits. Any of these apparatuses may also include a hanging mechanism to attach the housing (e.g., canister) or the collection bag to a hospital bed, wheelchair, surgical table, fluid pole, or other suitable platform.

In examples including an intermediary flow chamber, the intermediary flow chamber may be made of a rigid or semi-rigid material and may have a central tapered flow feature that is connected to a flutter valve that regulates the fluid flow using gravity in some examples. The intermediary chamber may be configured to create and maintain a differential pressure with respect to the collection bag that is typically downstream and the transit conduit that is typically upstream of the intermediary chamber. This differential pressure may create a unidirectional flow way to facilitate the movement of fecal material in synchronization with the vacuum pressure from the receptacle to the collection bag, via transit conduit and the canister.

In some examples, the intermediary flow chamber may be made of a rigid or semi-rigid material, may be external to a disposable or reusable collection chamber, and may rely on the displacement of fecal material from this external chamber to inside the collection chamber. The interface of these two chambers may work on the principle of mating orifices that provide a leak proof displacement of material. Examples of such an interface may include one-way nozzles, vales, Leur connections, and/or O-ring-ball-bearing-spring compression mechanisms. The intermediary flow chamber may also have an overflow prevention mechanism along the lines of a ball-valve float or hydrophobic cutoff valve or an electronic cutoff valve. This valve is used to prevent overflow from the chamber, as well as send an operational signal to the vacuum and fluid pump in the interface above.

Any of the apparatuses described herein may include one or more transparent windows (e.g., in the housing, collection chamber(s), tubing, etc.) to enable easy visualization of fluid, fecal material and efficacy of the connector joints. The fluid reservoir may be located in the lower half of the canister to provide more stability to overall system when hanging the bed of the patient.

The apparatuses described herein may also be configured to reduce or minimize sound during operation. Alternate repeated cycles of both the vacuum and fluid pumps may negatively impact the decibel level in the care environment, thereby interfere with patient recovery and cause discomfort to the patient, their visitors and their care providers. Sound-reduction features that may be included with any of these apparatuses may include insulating the internal walls of housing (e.g., canister) as well as muffling the outlets.

The housing may be configured to be ergonomic, shatter proof, and consumer friendly by incorporating materials including vinyl blends added to base polymers, and/or by incorporating safety-oriented design features in all molded and assembled components. The electronics and pumps may be insulated by materials used to make them resistant to fire.

Any of the apparatuses described herein may also include one or more disposable bags. The housing may be re-usable or semi-reusable, however reusing collection canister possess risk of increasing nosocomial infection among patients. To mitigate such issues, a disposable bag may be used, such as a flexible bag that is made of two or more layers of olephins, acetates and chlorides films; such bags may reduce odor and may enable easy and leak-proof connect-disconnect features and may be configured to allow the caregiver to visualize, record and monitor fecal waste.

Any of these disposable bags may have a one-way valve to prevent back-flow of fecal waste. For example, an assembly comprising charcoal filters, membranes of fluoropolymers, and other absorbent substrates may help manage flatulence. These apparatuses may also help maintain and hold a certain internal pressure to facilitate the movement of material in a predetermined direction. Any of these apparatuses may include a sensor to automatically record the quantum of output. As mentioned, these apparatuses may include an isolated chamber for fluid for irrigation, flushing, cleaning, hydrating, etc. The fluid chamber can be either disposed with each bag exchange or be reused, based on user preference. The fluid chamber can also be used to deliver therapeutic or wellness agents (e.g., drugs or other therapeutic compositions) for management and/or treatment of disease, and/or for dis-impacting, softening, cleaning of the lower GI tract.

As mentioned, these methods and apparatuses may also help manage gas, flatulence, smoke, odor, debris, lint, etc. to prevent such secretions from occluding the system and rendering it inoperable. For example, any of these apparatuses may include a flatulence release and deodorizing assembly that may be connected to the suction outlet line in a manner that the odor is neutralized and then expelled from the system. The assembly may include a carbon filter, charcoal filter, or another odor absorbing substrate, that is either encapsulated, shielded or layered with micro-porous structure. In some examples a charcoal filter may be covered with a film of fluoropolymers that has been optimized for barrier transmission, absorption of malodor and release of gases.

The receptacle may be configured for withdrawal from the body. The inner diameter of the anal canal is almost zero in resting state which can be distended up to 30 mm, while the inner diameter of the rectum (near the anorectal junction) is larger and can be between 30-60 mm. The receptacle may be configured to reside within the anatomy and may be delivered in a compressed form using one of the application methods described above. These apparatuses may be withdrawn from the anatomy after use and may include a mechanism allowing the receptacle (which may be substantially circular in shape), e.g., having a diameter of 8 mm, or larger, to be collapsed and removed from the anatomy by application of forces, e.g., near a transit conduit region of the apparatus. These forces may be transferred longitudinally along this conduit, which in turn disorients the receptacle to a linear form and can be moved out of the anatomy. In another example a deflation device may be used to collapse the receptacle, or a reverse scissor mechanism may be used to collapse and remove the receptacle. Also described herein are wrap-around mechanisms that work on the principle of purse draw-string, that are configured with the receptacle and transit conduit which can provide either a unidirectional ratchet like lock-in using gears, frictional forces, mechanical blocks, or free-flowing draw strings that relies of the user's physical force to collapse and retrieve the receptacle. Other withdrawal mechanisms described herein which may be used include a trigger that rebalances the negative pressure to assist in the removal of the product, activation of bioresorbable agents, and unwinding of tethers, tapes, or other support systems to facilitate the removal of receptacle away from the body.

For example, described herein are apparatuses (e.g., systems) for removal of fecal material from a patient's rectum that include: a receptacle configured to be applied in communication with the patient's rectum (e.g., held within the rectum); a connecting tube comprising a suction channel and one or more irrigation channels, the connecting tube configured to couple the suction channel to a suction port of the receptacle and the irrigation channel to an irrigation outlet of the receptacle; a canister housing from which the connecting tube extends; a fluid pump within the canister housing configured to couple to an irrigation fluid reservoir; a controller within the canister housing, the controller configured to apply one or more fecal removal cycles including applying suction through the suction port and applying irrigation from the irrigation outlet by controlling the fluid pump and by controlling a source of negative pressure; and a stool collection chamber configured to receive fecal material from the suction channel. The source of negative pressure may include a suction pump. The controller may also be configured to release suction (e.g., through the irrigation outlet or through a separate air outlet).

A system may include a receptacle configured to be applied in communication with the patient's rectum; a connecting tube comprising a suction channel and an irrigation channel, the connecting tube configured to couple the suction channel to a suction port of the receptacle and the irrigation channel to an irrigation outlet of the receptacle; a canister housing from which the connecting tube extends; a fluid pump within the canister housing configured to couple to an irrigation fluid reservoir; a controller within the canister housing, the controller configured to apply one or more fecal removal cycles including applying suction through the suction port and applying irrigation from the irrigation outlet by controlling the fluid pump to deliver between 1 ml and 1000 ml of irrigation fluid and by controlling a source of negative pressure to deliver between 15 mmHg and 500 mmHg of suction; and a stool collection chamber configured to receive fecal material from the suction channel.

For example a system may include: a receptacle configured to be applied in communication with the patient's rectum; a connecting tube comprising a suction channel, an air channel and an irrigation channel, the connecting tube configured to couple the suction channel to a suction port of the receptacle, the air channel to an air outlet of the receptacle and the irrigation channel to an irrigation outlet of the receptacle; a canister housing from which the connecting tube extends; a fluid pump within the canister housing configured to couple to an irrigation fluid reservoir; a controller within the canister housing, the controller configured to apply one or more fecal removal cycles including applying suction through the suction port, applying air from the air outlet, and applying irrigation from the irrigation outlet by controlling the fluid pump and one or more valves; and a stool collection chamber configured to receive fecal material from the suction channel.

The controller may be configured to determine parameters of a fecal removal cycle using sensor data from one or more sensor on the receptacle. The controller may be configured to determine parameters of a fecal removal cycle using pressure sensor data from one or more pressure sensors. The controller may be configured to alternate the application of suction and irrigation during each fecal removal cycle. The controller may be configured to apply a stream of irrigation fluid from the irrigation outlet of the receptacle. The controller may be configured to finish each fecal removal cycle by applying irrigation. The controller may be configured to automatically trigger the application of the one or more fecal removal cycles. In some examples the controller may be configured to automatically trigger the application of the one or more fecal removal cycles based on sensor data received from one or more sensors.

The connecting tube may include an air channel configured to couple to an air outlet of the receptacle. The controller may be configured to apply air through the air outlet when the controller detects a vacuum lock.

Any of these systems may include a vacuum pump within the canister housing, providing the source of negative pressure. The vacuum pump lay provide positive pressure as well as negative pressure; alternatively the system may include a pump for applying positive pressure.

Any of these systems may include an intermediate stool collection chamber within the canister housing having rigid walls and in fluid communication with the suction channel. The stool collection chamber may include a stool collection bag coupled to the intermediate stool collection chamber and configured to passively receive fecal material from the intermediate stool collection chamber when suction may be not being applied through the suction channel. The irrigation fluid reservoir may be coupled to the stool collection chamber.

The controller may be configured to issue an alert to add irrigation fluid when a level of irrigation fluid in the irrigation fluid reservoir falls below a threshold.

A system for removal of fecal matter from a patient's rectum may include: a receptacle configured to be applied in communication with the patient's rectum; a connecting tube comprising a suction channel and an irrigation channel, the connecting tube configured to couple the suction channel to a suction port of the receptacle and the irrigation channel to an irrigation outlet of the receptacle; a canister housing enclosing an intermediate stool collection chamber having rigid walls; a fluid pump within the canister housing configured to couple to an irrigation fluid reservoir; a suction pump within the canister housing; a controller configured to apply one or more fecal removal cycles including applying suction through the suction port and applying irrigation from the irrigation outlet by controlling the fluid pump to deliver between 1 ml and 100 ml of irrigation fluid and by controlling the suction pump to deliver between 25 15 mmHg and 500 mmHg of suction; a stool collection bag coupled to the canister housing; and a valve between the stool collection bag and the intermediate stool collection chamber, wherein the valve may be configured to be opened when suction may be not being applied so that collected fecal material may be transferred to the stool collection bag.

The controller may be configured to determine parameters of a fecal removal cycle using sensor data from one or more sensor on the receptacle. The controller may be configured to determine parameters of a fecal removal cycle using pressure sensor data from one or more pressure sensors. The controller may be configured to alternate the application of suction and irrigation during each fecal removal cycle. The controller may be configured to apply a stream of irrigation fluid from the irrigation outlet of the receptacle. The controller may be configured to finish each fecal removal cycle by applying irrigation. The controller may be configured to automatically trigger the application of the one or more fecal removal cycles. The controller may be configured to automatically trigger the application of the one or more fecal removal cycles based on sensor data received from one or more sensors. The controller may be configured to issue an alert to add irrigation fluid when a level of irrigation fluid in the irrigation fluid reservoir falls below a threshold.

The connecting tube may further comprise an air channel configured to couple to an air outlet of the receptacle. The controller may be configured to apply air through the air outlet when the controller detects a vacuum lock.

The irrigation fluid reservoir may be within the stool collection bag.

Also described herein are methods of removing fecal material from a patient's rectum, the method comprising: performing one or more fecal removal cycles of: applying between 15 mmHg and 500 mmHg of suction and between 1 ml and 500 ml of an irrigation fluid from a receptacle within the patient's rectum; and collecting fecal material from a suction lumen of the receptacle in a stool collection container. The stool collection container may be part of a system for removal of fecal material positioned near the patient.

Any of these methods may include sensing pressure within the patient's rectum at the receptacle and adjusting the one or more fecal removal cycles based on the sensed pressure. The method may include applying air from an air outlet of the receptacle into the patient's rectum as part of the one or more fecal removal cycles. In some examples, the method includes periodically repeating the performance of the one or more fecal removal cycles over the course of between 1 day to 29 days. Any of these methods may include inserting the receptacle into the patient's rectum.

In some examples, these methods include detecting that the stool collection container may be full or nearly full and alerting a caregiver to replace or empty the stool collection container. A method may include alerting a caregiver to add irrigation fluid when a level of irrigation fluid in an irrigation fluid reservoir falls below a threshold.

Performing the one or more fecal removal cycles may include applying suction followed by applying irrigation fluid. In some examples, performing the one or more fecal removal cycles comprises applying irrigation fluid followed by applying suction. Performing the one or more fecal removal cycles may include finishing an iteration of the one or more fecal removal cycles with an application of irrigation fluid.

Collecting fecal material in the stool collection container may include transferring the fecal material from a rigid-walled intermediate collection chamber to a collection bag comprising the stool collection container when suction may be not being applied from the receptacle.

A method of removing fecal material from a patient's rectum may include: detecting, from a receptacle residing within the patient's anal canal, a pressure level within the patient's rectum; processing the pressure level to determine parameters of a fecal removal cycle, wherein the fecal removal cycle includes applying suction from a suction port of the receptacle, and applying one or both of: an irrigation fluid from an irrigation outlet of the receptacle and air from an air outlet of the receptacle; controlling a source of negative pressure and a fluid pump that are both in communication with the receptacle to apply the fecal removal cycle according to the determined parameters; and collecting fecal material from the receptacle in a stool collection container.

Processing the pressure level to determine parameters of the fecal removal cycle may include selecting a negative pressure level and suction duration, wherein the negative pressure level may be between 25 mmHg and 500 mmHg. Processing the pressure level to determine parameters of the fecal removal cycle may include determining if irrigation fluid or air or both are applied as part of the fecal removal cycle. In some examples processing the pressure level to determine parameters of the fecal removal cycle comprises selecting an amount of irrigation fluid to apply as part of the fecal removal cycle, wherein the amount of irrigation fluid may be between 1 ml and 100 ml.

Any of these methods may include inserting the receptacle into the patient's rectum. These methods may include detecting that the stool collection container is full or nearly full and alerting a caregiver to replace or empty the stool collection container. The methods described herein may include alerting a caregiver to add irrigation fluid when a level of irrigation fluid in a reservoir falls below a threshold.

Controlling the source of negative pressure and the fluid pump to apply the fecal removal cycle according to the determined parameters comprises applying suction followed by applying irrigation fluid. Collecting fecal material and irrigation fluid in the stool collection container may include transferring the fecal material and irrigation fluid from a rigid-walled intermediate collection chamber to a collection bag comprising the stool collection container when suction is not being applied from the suction port of the receptacle.

For example, a method of removing fecal material from a patient's rectum may include: detecting, from a receptacle residing within the patient's anal canal, a pressure level within the patient's rectum; processing the pressure level to determine parameters of a fecal removal cycle, wherein the fecal removal cycle includes applying suction from a suction port of the receptacle, and applying one or both of: an irrigation fluid from an irrigation outlet of the receptacle and air from an air outlet of the receptacle; controlling a source of negative pressure to apply a negative pressure level of between 15 mmHg and 500 mmHg according to the determined parameters; controlling a fluid pump to apply between 1 and 500 ml of irrigation fluid according to the determined parameters; and collecting fecal material and irrigation fluid from the receptacle in a stool collection container.

For example, a method of removing fecal material from a patient's rectum may include: performing one or more fecal removal cycles of: applying between 15 mmHg and 500 mmHg of suction and between 1 ml and 500 ml of an irrigation fluid from a receptacle within the patient's rectum; collecting fecal material from a suction lumen of the receptacle in an intermediate stool collection container having rigid walls; and passively transferring collected fecal material from the intermediate stool collection container into a stool collection bag when suction is not being applied from the receptacle.

Passively transferring collected fecal matter may comprise transferring by gravity. In some examples passively transferring comprises opening a valve between the intermediate stool collection container and the stool collection bag.

Performing the one or more fecal removal cycles may include applying the irrigation fluid by drawing irrigation fluid from an irrigation reservoir in the stool collection bag. Any of these methods may include inserting the receptacle into the patient's rectum. The method may include detecting that the stool collection bag is full or nearly full and alerting a caregiver to replace or empty the stool collection bag. The method may include alerting a caregiver to add irrigation fluid when a level of irrigation fluid in an irrigation fluid reservoir falls below a threshold.

Performing the one or more fecal removal cycles may include applying suction followed by applying irrigation fluid. Performing the one or more fecal removal cycles may include applying suction followed by applying irrigation fluid, followed by applying suction. In some examples, performing the one or more fecal removal cycles comprises applying irrigation fluid, followed by applying suction.

The invention additionally provides methods, apparatuses and computer program products for controlling an apparatus or system that is configured for removal of fecal material from a patient's rectum.

In an embodiment, the invention provides a method for controlling an apparatus configured for removal of fecal material from a patient's rectum. The apparatus includes a receptacle configured to be positioned at least partially within a patient's lower gastrointestinal tract, a connecting tube comprising at least a suction channel, the connecting tube configured to couple the suction channel to a suction port of the receptacle, a controller configured to apply one or more fecal removal cycles including applying suction through the suction port and by controlling a source of negative pressure to deliver suction, and a stool collection chamber configured to receive fecal material from the suction channel. The method comprises (i) responding to detection of a first suction operation session initiation event, by implementing a first suction operation session wherein implementation of the first suction operation session comprises (a) applying suction for generating negative pressure at the receptacle, (b) responding to detection of a first suction operation session termination event by terminating the first suction operation session, and wherein terminating the first suction operation session comprises terminating application of suction for generating negative pressure at the receptacle, (2) implementing a next suction operation session, wherein implementation of the next suction operation session comprises (c) applying suction for generating negative pressure at the receptacle, and (d) responding to detection of a next suction operation session termination event by terminating the next suction operation session, and wherein terminating the next suction operation session comprises terminating application of suction for generating negative pressure at the receptacle. Termination of the application of suction within the first suction session and initiation of application of suction within the next suction operation session may in specific embodiments be separated by an interval of time. Additionally, the receptacle may be positioned at least partially within a patient's lower gastrointestinal tract for the interval of time separating the termination of application of suction within the first suction session and the initiation of application of suction within the next suction operation session.

In a further embodiment of the method, the next suction operation session, is implemented in response to either of (i) determining elapse of a predetermined interval of time from occurrence of a predefined event associated with a preceding suction operation session, and (ii) detection of a next suction pump operation session initiation event.

In a method embodiment, within the first suction operation session, applying suction for generating negative pressure at the receptacle comprises applying suction in a pulsed operation cycle, said pulsed operation cycle comprising alternately (i) generating negative pressure at the receptacle, and (ii) delivering fluid to a region where the receptacle is positioned, through a fluid outlet wherein the fluid outlet is coupled with a fluid source by a fluid channel that provides a fluid path between fluid source and the fluid outlet.

In another method embodiment, within the second suction operation session, applying suction for generating negative pressure at the receptacle comprises applying suction in a pulsed operation cycle comprising alternately (i) generating negative pressure at the receptacle, and (ii) delivering fluid to a region where the receptacle is positioned, through a fluid outlet wherein the fluid outlet is coupled with a fluid source by a fluid channel that provides a fluid path between fluid source and the fluid outlet.

In more specific embodiments any of the above methods, the fluid delivered through a fluid outlet is a liquid or a gas.

The invention also provides an apparatus configured for removal of fecal material from a patient's rectum, the apparatus comprising (i) a receptacle configured to be positioned at least partially within a patient's lower gastrointestinal tract, (ii) a connecting tube comprising at least a suction channel, the connecting tube configured to couple the suction channel to a suction port of the receptacle, and (iii) a processor implemented controller configured to apply one or more fecal removal cycles including applying suction through the suction port and by controlling a source of negative pressure to deliver suction; and a stool collection chamber configured to receive fecal material from the suction channel.

The controller is configured for (i) responding to detection of a first suction operation session initiation event, by implementing a first suction operation session wherein implementation of the first suction operation session comprises (a) applying suction for generating negative pressure at the receptacle, (b) responding to detection of a first suction operation session termination event by terminating the first suction operation session, and wherein terminating the first suction operation session comprises terminating application of suction for generating negative pressure at the receptacle, (2) implementing a next suction operation session, wherein implementation of the next suction operation session comprises (c) applying suction for generating negative pressure at the receptacle, and (d) responding to detection of a next suction operation session termination event by terminating the next suction operation session, and wherein terminating the next suction operation session comprises terminating application of suction for generating negative pressure at the receptacle. Termination of the application of suction within the first suction session and initiation of application of suction within the next suction operation session may in specific embodiments be separated by an interval of time. Additionally, the receptacle may be positioned at least partially within a patient's lower gastrointestinal tract for the interval of time separating the termination of application of suction within the first suction session and the initiation of application of suction within the next suction operation session.

In an embodiment the apparatus may be configured such that, the next suction operation session, is implemented in response to either of (i) determining elapse of a predetermined interval of time from occurrence of a predefined event associated with a preceding suction operation session, and (ii) detection of a next suction pump operation session initiation event.

In an embodiment the apparatus may be configured such that, within the first suction operation session, applying suction for generating negative pressure at the receptacle comprises applying suction in a pulsed operation cycle, said pulsed operation cycle comprising alternately (i) generating negative pressure at the receptacle, and (ii) delivering fluid to a region where the receptacle is positioned, through a fluid outlet wherein the fluid outlet is coupled with a fluid source by a fluid channel that provides a fluid path between fluid source and the fluid outlet.

In another embodiment the apparatus may be configured such that, within the second suction operation session, applying suction for generating negative pressure at the receptacle comprises applying suction in a pulsed operation cycle comprising alternately (i) generating negative pressure at the receptacle, and (ii) delivering fluid to a region where the receptacle is positioned, through a fluid outlet wherein the fluid outlet is coupled with a fluid source by a fluid channel that provides a fluid path between fluid source and the fluid outlet.

In more specific embodiments any of the apparatus described above, the fluid delivered through a fluid outlet is a liquid or a gas.

The invention also provides a computer program product for controlling an apparatus configured for removal of fecal material from a patient's rectum. The apparatus includes a receptacle configured to be positioned at least partially within a patient's lower gastrointestinal tract, a connecting tube comprising at least a suction channel, the connecting tube configured to couple the suction channel to a suction port of the receptacle, a controller configured to apply one or more fecal removal cycles including applying suction through the suction port and by controlling a source of negative pressure to deliver suction, and a stool collection chamber configured to receive fecal material from the suction channel. The computer program product comprises a non-transitory computer usable medium having computer readable program code embodied therein, the computer readable program code comprising instructions for implementing at a processor, the steps of (i) responding to detection of a first suction operation session initiation event, by implementing a first suction operation session wherein implementation of the first suction operation session comprises (a) applying suction for generating negative pressure at the receptacle, (b) responding to detection of a first suction operation session termination event by terminating the first suction operation session, and wherein terminating the first suction operation session comprises terminating application of suction for generating negative pressure at the receptacle, (2) implementing a next suction operation session, wherein implementation of the next suction operation session comprises (c) applying suction for generating negative pressure at the receptacle, and (d) responding to detection of a next suction operation session termination event by terminating the next suction operation session, and wherein terminating the next suction operation session comprises terminating application of suction for generating negative pressure at the receptacle. Termination of the application of suction within the first suction session and initiation of application of suction within the next suction operation session may in specific embodiments be separated by an interval of time. Additionally, the receptacle may be positioned at least partially within a patient's lower gastrointestinal tract for the interval of time separating the termination of application of suction within the first suction session and the initiation of application of suction within the next suction operation session.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

In FIGS. 5A-5C the receptacles are reinforced to enhance collapse strength.

FIG. 17A shows a front view, and FIG. 17B shows a back view.

in FIG. 25 the apparatus includes separate stool collection and fluid source chambers (e.g., bags).

in FIG. 25 the fluid source chamber (e.g., bag) is within the housing (e.g., cannister).

FIG. 28 is a flowchart illustrating a first method for controlling a fecal management apparatus for eliminating buildup or accumulation of substantial amount of fecal matter in the rectum of a subject or user of said apparatus.

DETAILED DESCRIPTION

In general, the apparatuses described herein are configured to collect fecal waste material from a patient that is in need therefore, such as a bedridden and/or incontinent, including unconscious, mobility-impaired or comatose patients. Thus, described herein are apparatuses (systems, devices, etc.) and methods of collecting and managing fecal waste material.

An apparatus for collecting fecal waste as described herein may generally include a receptacle for interfacing with the subject (e.g., patient, human or non-human), a connecting tube, a source of fluid, one or more pumps (e.g., fluid pump, vacuum pump), a collection chamber (e.g., collection bag) and a controller coordinating the operation of the apparatus. The apparatus may also include one or more valves, filters, controllers, outputs (e.g., displays), inputs (e.g., controls) or there like. These apparatuses may be active stool management systems, which do not depend on patent defecation process to operate. These apparatuses may collect stool from within the subject's rectum and transfer it to a collection chamber (e.g., collection bag) in a closed-loop, low-odor, hygienic manner.

Any of these apparatuses may be vacuum assisted fecal incontinence management apparatuses (also referred to as fecal collection or stool collection apparatuses) that are configured to autonomously evacuate liquid and semi-formed fecal waste in bedridden subjects and contain the solid and/or liquid waste in an odor-proof collection container (e.g., collection bag). These apparatuses may be configured to operate on virtually any consistency of stool and may be configured to apply patterns of liquid (e.g., water) and suction to efficiently and cleanly remove waste. In some examples a negative pressure (e.g., suction) may be generated by a portable pump housed in the apparatus. This pump may be powered by a battery (e.g. rechargeable battery) and may be controlled by a microcontroller, all of which may be housed in the apparatus, such as in a canister. The negative pressure generated by the pump may be applied to a subject's rectum via a soft, universal receptacle. The device may be programmed to activate periodically, assess the state of rectal contents, and apply a combination of negative suction pressure along with stream of air, water or both, to suction out the rectal waste into a collection chamber and/or container. Voided waste material may be collected in a single-use collection bag. Either or both negative and positive pressure may be used to push out waste from the rectum to the collection bag.

Figure 1A:
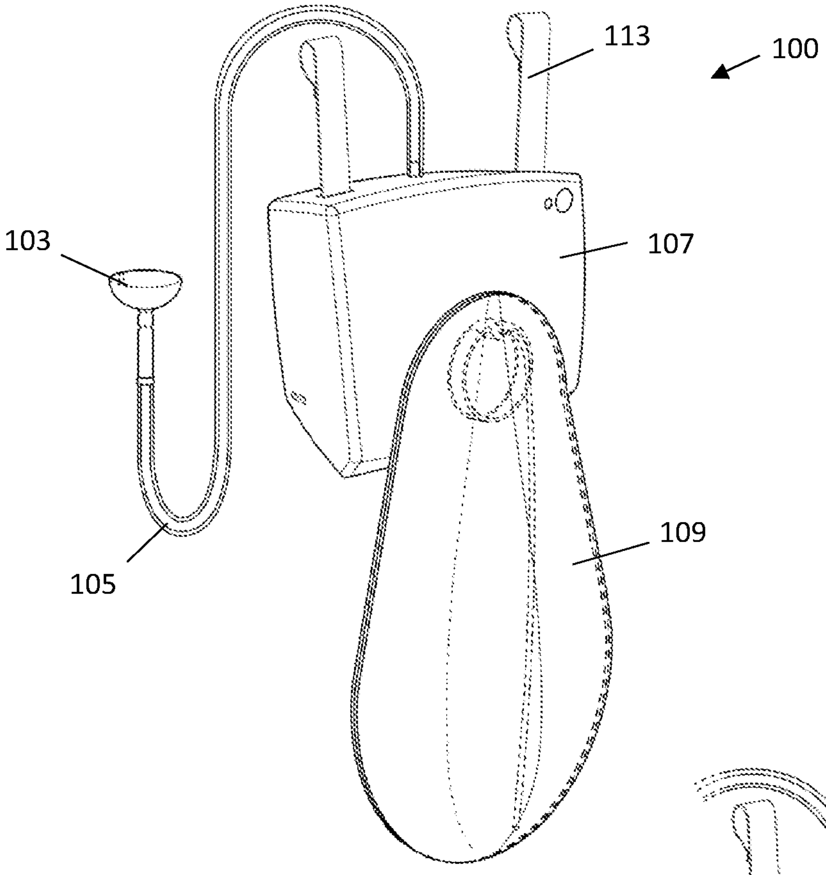
FIG. 1A is one example of an apparatus for collecting fecal matter as described herein.

For example, FIGS. 1A-1D illustrate examples of apparatuses for collecting fecal material. In FIG. 1A, the apparatus 100 includes a receptacle 103 that is configured for insertion into the rectal cavity and connected to a connecting tube 105 that couples the receptacle to the rest of the apparatus. In FIG. 1A the apparatus includes a housing ("cannister" 107) that may enclose electronic and electromechanical components such as a controller, one or more pumps, the power circuitry (which may include a rechargeable battery), and one or more valves, and vents. In FIG. 1A a removable container (bag 109) is coupled to the housing. In this example the same removably container (bag 109) is configured to hold both the fluid to be injected or applied (e.g., water) and to collect waste (e.g., fecal material). The removable container may be referred to as a bag, a stool collection and water storage bag, or the like. This dual removable container may include compartments for both, fluid to be applied and for collecting waste (e.g., fecal material). Each compartment is separated from the other with a middle plastic layer. In FIG. 1A the apparatus may also include one or more mounts 113 or attachment mechanisms for securing the apparatus to a stand, bed, wall, etc. The mounts may include straps, clips, or the like.

Figure 1B:
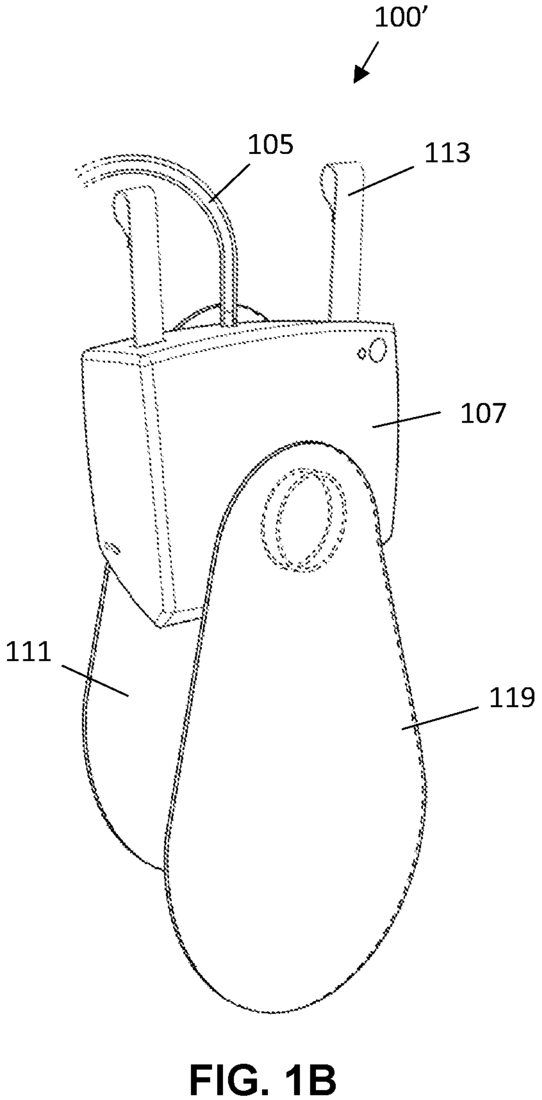
FIG. 1B is another example of an apparatus for collecting fecal matter.
Figure 1C:
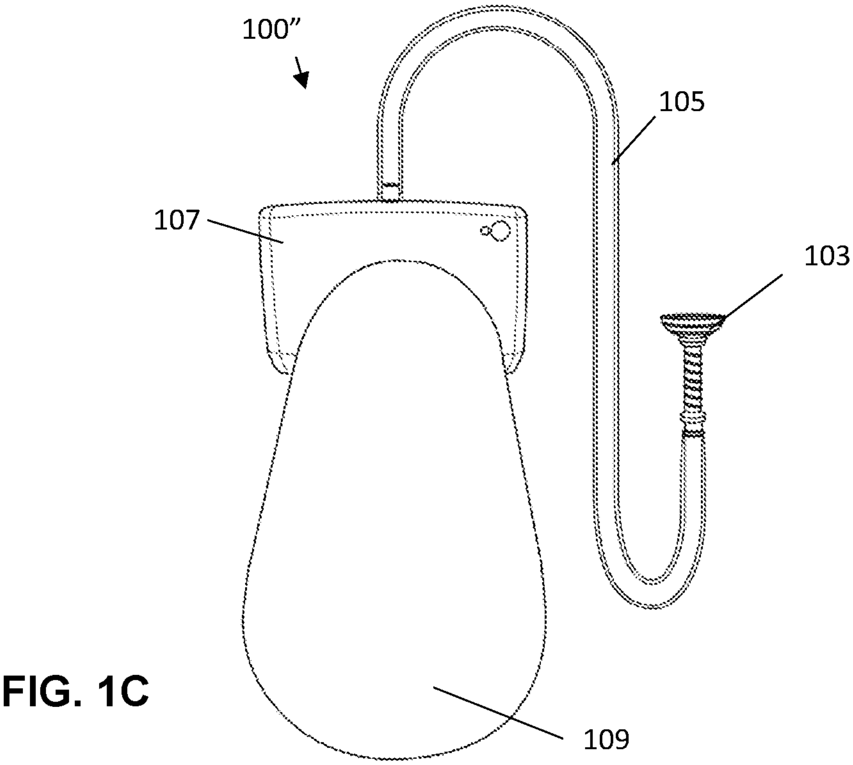
FIG. 1C is a front view of an example of an apparatus for collecting fecal matter.
Figure 1D:
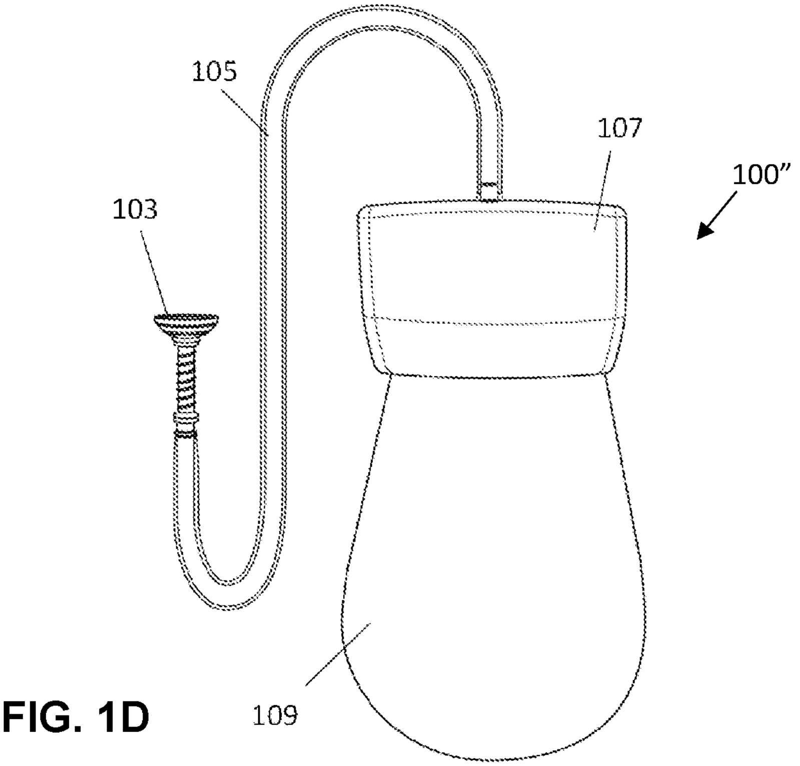
FIG. 1D is a back view of the apparatus of FIG. 1C.

FIG. 1B shows another example of an apparatus 100' for collecting fecal material similar to that shown in FIG. 1A, including a receptacle (not shown), connecting tube(s) 105, and cannister 107. The apparatus may also include separate containers for collecting fecal material 119 and for providing fluid (flushing fluid) 111. Both containers may be bags that may be attached to the housing, as shown in FIG. 1B. FIGS. 1C and 1D shows front and back views, respectively, of another example of an apparatus 100" similar to that shown in FIG. 1A.

Any of the apparatuses described herein may include an inserted or insertable collection structure (referred to herein as a "receptacle") that may interface with the patient and collect fecal matter and fluid (or in some examples gas) from the rectum. The receptacle may also deliver fluid and/or gas into the rectum, to help soften, dislodge and/or move fecal matter into the receptacle and out of the rectum. In some cases, the receptacle may be removable and replaceable. The receptacle may be held close to, and may interface with, the patient's anatomy. The receptacle may collect and/or direct fecal matter. The receptacle can be on either side of, or within, the anal canal, and may be inside the rectum near, or in certain embodiments, external to the patient's body but affixed to either the anal opening, perineum, buttocks or all of these.

Figure 2A:
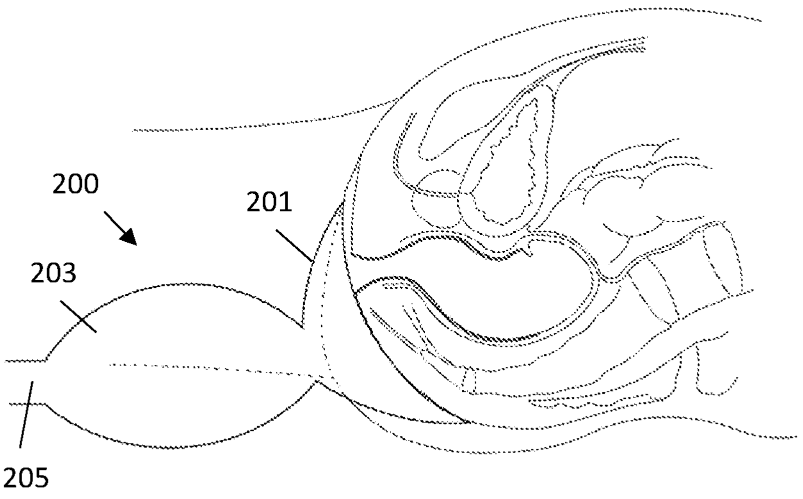
FIG. 2A illustrates one example of a receptacle attached to a patient (in this example, adhesively attached to the patient's perineum). This example includes an intermediate holding chamber within the receptacle.

The receptacle may collect, contain and facilitate the diversion of fecal matter using vacuum suction, e.g., negative pressure, before, during or after the defecation process, without causing any erythema, necrosis, ulceration, dysfunction, erosion, dermatitis, maceration, etc. The receptacle may be soft, yet firm, absorbable, lubricious, flow-directing, compliant, biocompatible to derma, mucosa, blood and sub-cutaneous contact, etc. For example, the receptacle may include an absorbent material supported by a non-permeable membrane and an adhesive layer, that applies over the anal opening, perineum, and buttocks of the patient. One example of a receptacle 200 is illustrated in FIG. 2A. In this example the receptacle includes an opening placed over the anus and is secured by a pad 201 to the patient's anatomy. The receptacle in this example is attached to patient perineum with an adhesive. Upon defecation by the patient, the stool is collected in the holding chamber 203 of the receptacle and is then moved to a collection chamber (not shown) using negative suction or gravity. The receptacle may be coupled to or integral with a connecting tube 205. The shape of the pad may be predefined to cover the patient's anatomy but can also be customized based on the anatomy by way of cutting, trimming or tearing along per-perforated line. The adhesive may be applied to exposed skin along the perimeter of the pad, over it or at select points, in a manner that may avoid moisture build up, redness, dermatitis, maceration. In some examples the receptacle may include an absorbent material that may be supported by a non-permeable membrane and may be kept flat below on a patient surface. In some examples the absorbent material may be supported by a non-permeable membrane, and wrapped around the patient's anatomy, similar to an application of a diaper or an undergarment.

Any of the receptacles described herein may include one or more sensors. For example, a receptacle may be configured to house one or more moisture and/or motion sensors that can be used for both activating the vacuum mechanism or alerting a caregiver by way of either sound or visual indication.

Figure 2B:
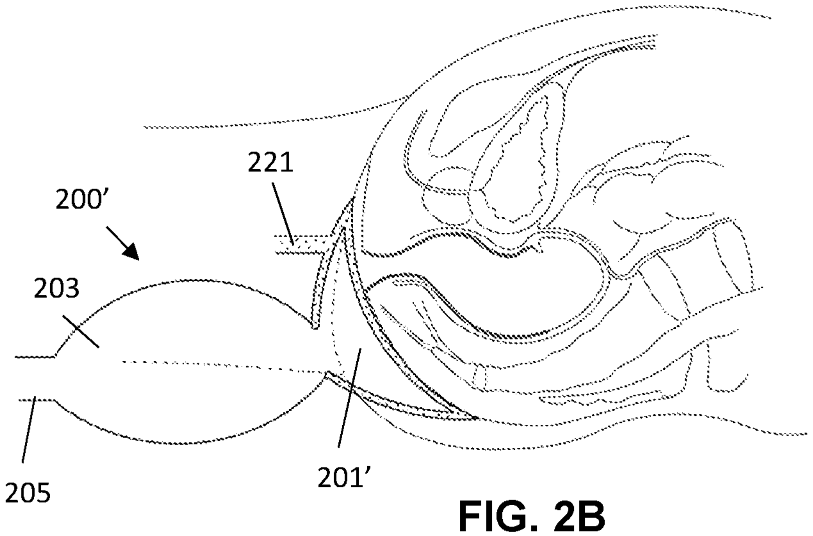
FIG. 2B shows another example of a receptacle attached to a patient, held in place by negative pressure. This example also includes an intermediate holding chamber within the receptacle.

The receptacle 200 shown in FIG. 2A includes a cup-like structure that is anchored flush with the anal opening and is external to the patient. The cup 201 can be one of a variety of shapes and may be configured to closely fit with the patient's anatomy. In FIGS. 2A and 2B the receptacle 200, 200' includes an interim volume 203 ("holding chamber") to collect the fecal material and then transfer it to a collection container (not shown). The cup shapes may be one or more of: round, oval, elliptical, umbel, parabolic, semi-circle, disc, hyperbolic, etc. The cup can be molded or formed of any soft, pliable material like silicone, polyurethane, thermoplastic elastomer or blend of polymers that can also include a fluoropolymer, chlorides or olephins.

As shown in FIGS. 2A-2B, the cup can be anchored to the anal opening by means of negative pressure (FIG. 2B), a strap that can be wrapped around the pelvic region, an adhesive that is applied to the periphery of the cup (FIG. 2A), or by way of physical pressure such that the cup abuts against the anal opening. In FIG. 2B the receptacle 200' is held in place using negative pressure and not adhesive. For example, the cup 201' includes a suction port 221 that may be used to apply suction to secure the periphery of the cup to the patient's anatomy.

Figure 2C:
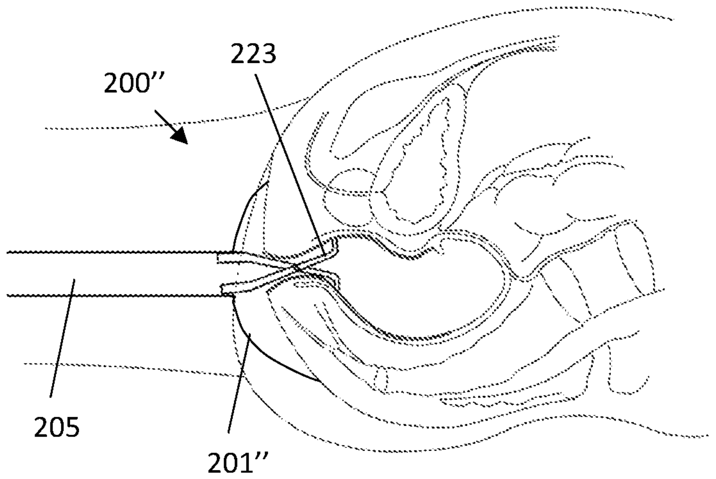
FIG. 2C shows an example of a receptacle anchored within the patient's rectum.
Figure 2D:
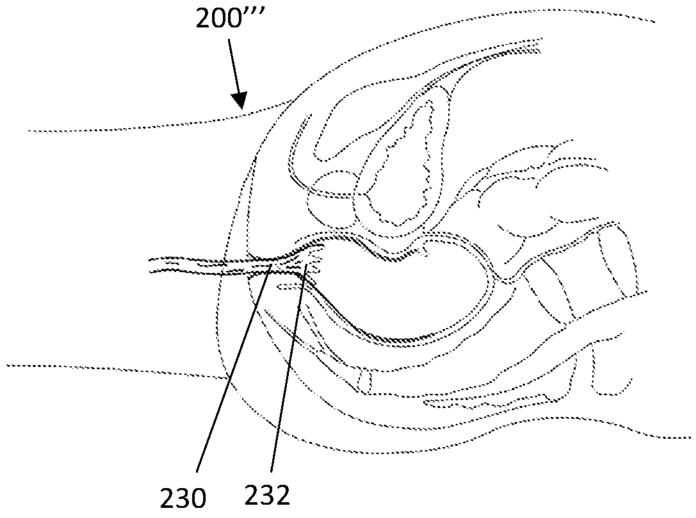
FIG. 2D shows an example of a receptacle anchored within the patient's rectum using a self-expanding member (configured as a self-expanding frame).
Figure 2E:
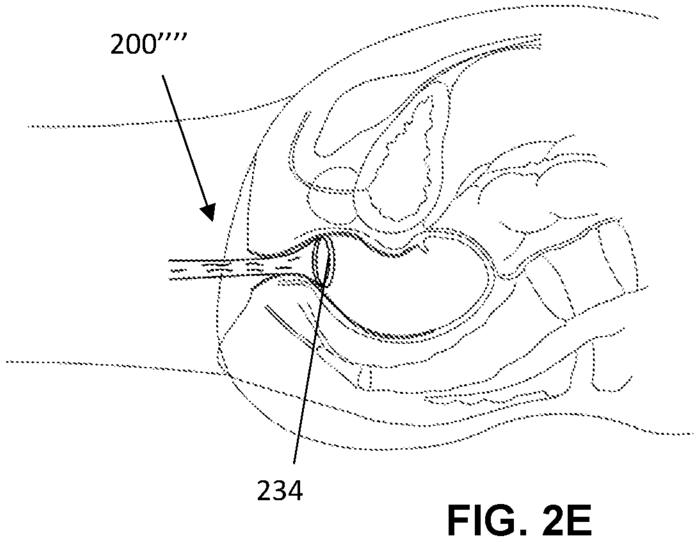
FIG. 2E shows an example of a receptacle anchored within the patient's rectum using a self-expanding member (configured as an expanding ring).
Figure 2F:
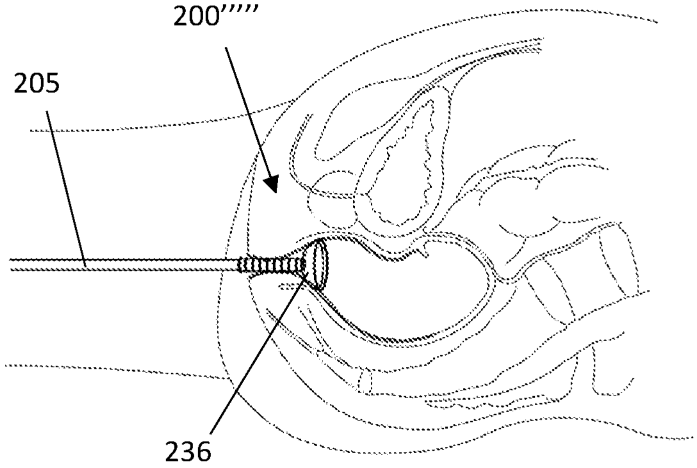
FIG. 2F shows an example of a receptacle anchored within the patient's rectum using a self-expanding member (configured as a self-expanding cup).

In some examples the anorectal junction may be used to anchor the receptacle, such as a cup portion 201", on the outside of anal canal. This mechanism is similar to a parachute like device, where the filaments of the chute are flowing distally/away from the cup inside the anatomy. Conceptually, instead of a filament a more rigid structure like tentacles or 'S' or 'J', or other angled shaped hooks can also be used to latch on to the anorectal junction and abut against the anal opening. FIG. 2C illustrates an example of a receptacle 200" that is anchored inside the patient rectum using anchors 223 (shown as inverted hooks or barbs). This variation also does not include a holding chamber (e.g., 203 in FIGS. 2A-2B). The stool is removed directly from the rectum into a collection chamber using negative suction pressure. In any of the receptacles described herein the anal canal may be used to anchor the receptacle on the outside of anal canal and/or within the anal canal, as shown in FIGS. 2D-2F, below. This securement mechanism shown in FIG. 2C may include a self-expanding material such as a foam, wicking fabrics, gels, etc. with a lumen that both anchors the receptacle as well as provides a smooth lumen for the flow of bodily secretions. These mechanisms can rely on a tight fit due to surface friction and/or due to adhesion. In FIG. 2C, the anchors may be, for example, a lattice including two arms that scissor together having a pivot or junction point that may be located outside the body where the proximal end may be connected to a vacuum source and the distal end touches the walls of the rectal mucosa and functions as a receptacle.

Any of the apparatuses described herein, including the receptacle portion of the apparatus, may include moisture and/or motion sensor that can be used for both activating the vacuum mechanism or alerting an individual by way of either sound or a visual indication. For example, the receptacle may include one or more sensors (e.g., moisture sensors) with the cup region.

FIGS. 2D-2F illustrate examples of receptacles that may be used herein, shown inserted. In each of these examples the receptacle resides in the rectum and is anchored within the anus. For example, FIG. 2D shows and example of a receptacle 200''' that is anchored inside the patient rectum using a stent or a similar self-expanding structure having arms or ribs that are biased to expand gently, so that the distal end region 232 expands more than the more proximal neck region 230. The neck region in any of these receptacles may have a minimum collapse profile (e.g., of 0.5 cm, 0.6 cm, 0.7 cm, 0.8 cm, 0.9 cm, 1 cm, 1.1 cm, 1.2 cm, 1.3 cm, 1.4 cm, 1.5 cm, 2 cm, 2.5 cm, 3 cm, etc. to maintain the patency of the receptacle waste channel even during the application of suction and against the constriction of the anal sphincter. The self-expanding structure may be covered or coated with a fluid-impermeable, biocompatible polymeric material. Thus, the receptacle may include a sleeve-like construction with self-expanding members attached or secured therein. In FIG. 2D, for example, the receptacle may include a self-expanding tubular or ring like structure 234 and the proximal end of the receptacle may transition into a sheath that facilitates the removal of fecal matter. The tubular structure can be cut to form a lattice and used like a stent. The lattice may have multiple struts that can be either fixed or flexible to expand and contract, scissor-like, inside the anatomy. In one example, a straight wire of optimal tensile strength may be formed into a repeating patterned loops (e.g., sinusoidal loops, zig-zag loops, etc.) that make receptacle malleable, particularly the neck region. The wire can be compatible for MR examination. In some examples the lattice wires may be circumferential in nature and can be made either from a single wire or multiple wires that are connected using a connector or welded at the ends. A straight wire of optimal tensile strength may be converted into a wire form which the struts are circumferential and have a wave form that allows the lattice to compress during peristaltic contractions and may make the wire-form malleable/pliable.

FIG. 2E shows another example of a receptacle 200"" inserted into the body. In FIG. 2E, the receptacle is anchored inside the patient rectum using a ring 234 or a similar self-expanding mechanism. The neck region in this example may also be configured to have a minimum collapse profile. For example, in any of these receptacles the receptacle may include supports (ribs, rings, etc.) configured to prevent collapse. In FIG. 2E, the ring-like structure can be formed into a purely circumferential configuration or onto an amoeba or star shape, having flared flanges to connect to the rectal walls. The ring may be made of an amorphous polymer with good surface frictional properties to anchor on the walls of the mucosa. In some examples, the ring may be made of two or more materials that are of different durometers, tensile strength and flexural modulus while also being MR compatible.

In some examples the receptacle may be anchored inside the patient rectum using a resilient, self-expanding cup or a balloon. For example, the example of the receptacle 200'"" shown in FIG. 2F is configured as a self-conforming cup-shaped structure 236 that resides in the rectum. The inserted cup-shaped structure can be semi-circle, spherical, umbel, elliptical, parabolic, or hyperbolic. The cup can be made of an amorphous or semi-crystalline polymer in either singular/block or co-blended form.

The inserted cup-shaped structure (cup) typically has a larger open face at the distal end to collect fecal waste that is getting pushed towards it during GI Motility (or drawn to it using the suction), and a slightly smaller luminal opening at the opposite proximal end from where the waste is suctioned out to collection chambers. The cup may also include a hub (shown in greater detail below) from where the fluid may be injected into rectum; a separate channel (the central waste lumen) may be used to apply negative pressure (vacuum/suction).

Figure 3A:
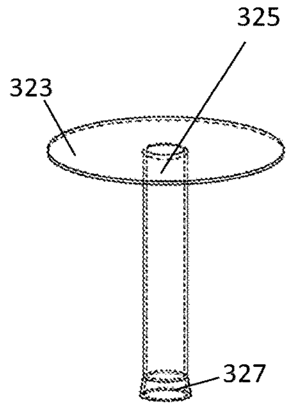
FIGS. 3A-3C illustrate example of receptacles including features that may be used with any of the apparatuses descried herein.
Figure 3B:
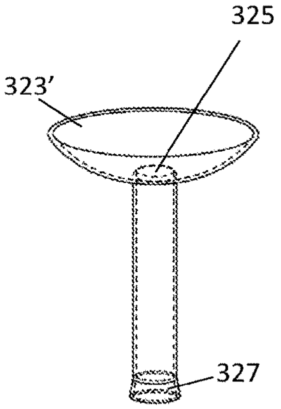
Figure 3C:
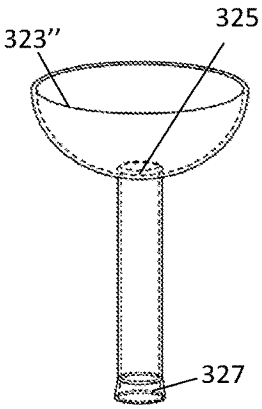

FIGS. 3A-3C illustrate examples of receptacles that may be used in any of the apparatuses described herein. In any of these examples the receptacle may be formed of a soft, resilient material, such as or including silicone, PU, TPU, TPE or other soft, shape-retaining materials. The receptacle may be reinforced (e.g., with a nitinol or other shape-memory material, e.g., forming ribs, rings, struts, etc.). In FIG. 3A the receptacle includes a flanged distal end 323 and a central (waste) lumen 325. The proximal end may include a connector to connect to a connecting tube (e.g., waste removal tube) or it may be integrally formed with and/or attached to the connecting tube (not shown).

The example receptacle shown in FIG. 3B includes a curved (parabolic shaped) cup region at the distal end 323'. In some examples the curved distal end region may be shaped to fit against the wall of the rectum. For example, the distal end region may be curve outwards more (e.g., transition to a more convex, trump shape). FIG. 3C shows an example in which the curved (parabolic shaped) cup region at the distal end 323" is slightly larger than in FIG. 3B.

Figure 4A:
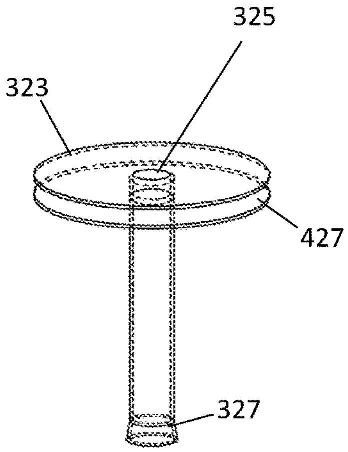
FIGS. 4A-4C show examples of receptacles including features that may be used with any of the apparatuses descried herein. The receptacles shown in FIGS. 4A-4C include multiple anchors to assist in securing the receptacle within the rectum.
Figure 4B:
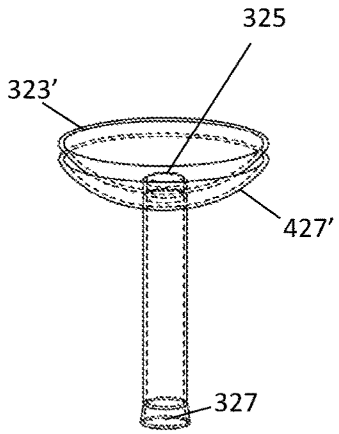
Figure 4C:
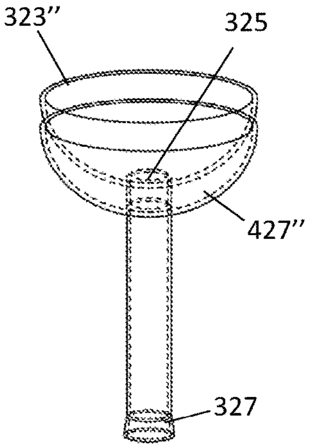

Any of the receptacles described herein may include multiple layers in the distal cup-shaped region. For example, the distal cup-shaped region of the receptacle may include two or more layers with a spacer in between, as shown FIGS. 4A-4C. The spacer 427, 427', 427" can be in the form of a lattice, molded struts, ball/square like form, or other similar designs, to maximize the collection and diversion of fecal material. The spacer may be positioned parallel to the cup-shaped region. In some examples, the spacer may be smaller than the cup-shaped region or may be formed as arms or struts extending behind the cup-shaped region. In addition to the materials described, the cup can also have moisture absorbing materials that are either affixed, layers, or molded with the cup, to further reduce any incidence of leakage or seepage. The additional layers may act as additional anchors. The more than one layer may therefor help anchor the receptacle within the rectum for better stability and reduced leakage.

Figure 5A:
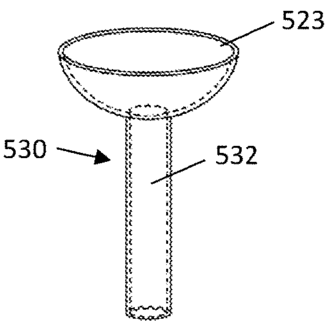
FIGS. 5A-5C show examples of receptacles including features that may be used with any of the apparatuses described herein.
Figure 5B:
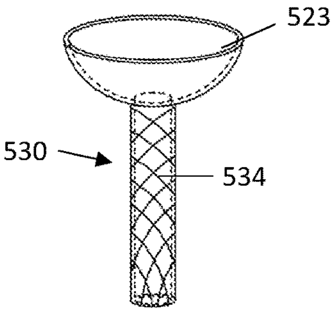
Figure 5C:
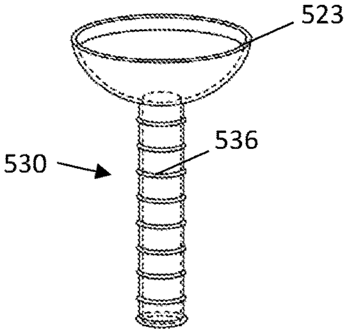

As mentioned above, any of the receptacles descried herein may include supports, in particular in the neck region of the receptacle. For example, FIGS. 5A-5C illustrate receptacles including supports. FIG. 5A shows a receptacle in which the neck (or shaft) region 530 is formed of a material 532 that is less resilient than the material forming the distal cup-shaped region 523. In some examples the neck/shaft region may have a larger wall thickness than the cup-shaped region along its length (or a portion of its length). In FIG. 5B the neck or shaft region 530 includes a reinforcing material, such as wires or struts 534 that may strengthen and prevent collapse. Thus, in any of these receptacles the neck (e.g., shaft) of the receptacle may be strengthened or supported using ribs, breading, etc. to increase the collapse strength under negative pressure and/or radial compression. FIG. 5C shows another example of a receptacle in which the shaft or neck region 530 is supported by a series of support rings 536 that may be formed of the same material (but have a larger wall thickness) or a different material, such as a metal, polymer, etc.

Figure 6A:
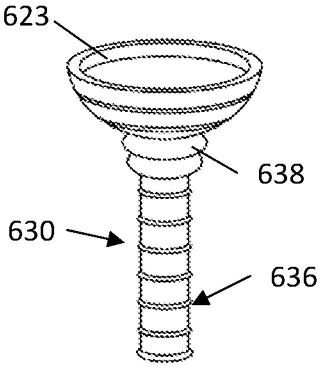
FIGS. 6A-6C show examples of receptacles including features that may be used with any of the apparatuses described herein. The receptacles shown in FIGS. 6A-6C show receptacles including ribs to enhance the strength of the receptacle and to prevent kinking.
Figure 6B:
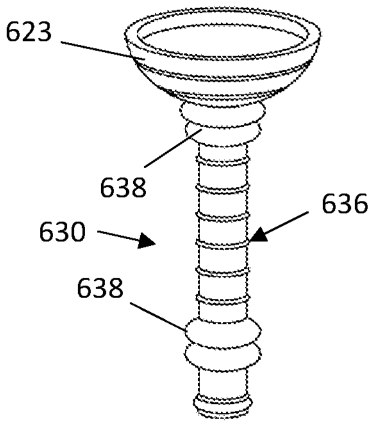
Figure 6C:
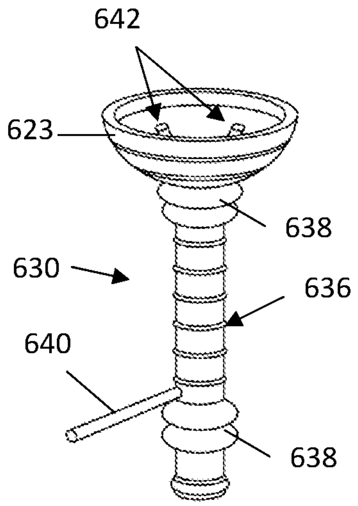

FIGS. 6A-6C show examples of receptacles including features that may be included in any of the receptacles described herein. The receptacles shown in FIGS. 6A-6C are configured with multiple ribs to increase the collapse strength (resistance to collapsing the waste lumen, for example) against negative pressure and compression. These receptacles may include one or more regions with concertinaed sides ("bellows") 638 to allow it to expand and contract during operation. These bellows regions at one or more location may improve receptacle flexibility and prevent any kinking in the conduit when transiting from the anorectal junction and the anus. In FIGS. 6A-6C each of the receptacles includes supporting rings 636 arranged along the length of the neck/shaft region 630, as well as the cup region 623. In FIG. 6A a single bellow region is positioned between the cup region and the shaft. FIG. 6B shows an example with a bellows region between the cup region and the shaft as well as at a proximal region (e.g., before transitioning to the connecting tube. FIG. 6C also includes multiple bellows regions (similar to FIG. 6B) but also show one example of an irrigation channel 640 with multiple irrigation outlets 642. In FIG. 6C the irrigation channel is shown exiting the receptacle and may be coupled to a separate irrigation line or to an irrigation line integrated into the connecting tube, as will be described in further detail below. In some examples the irrigation line(s) may remain integrated into the receptacle proximal end and may couple with integrated irrigation lines in the connecting tube.

The receptacles described herein may be a soft, compliant, sheath/tube/lay-flat that traverses through the anal canal without eroding the canal, causing any injury and by limiting the foreign body sensation to the patient. As mentioned above, the connecting tube may be a conduit that houses the independent channels to deliver fluid and vacuum pressure. The conduit may be configured to not collapse under vacuum, thereby preventing vacuum lock in the system, and to not cause any erosion of the anal canal. The conduit may have a co-extruded lumen to optimize for space and sensitivity to the anatomy, may have secondary braiding or molded features along the horizontal axis to create micro-corrugated structure, and/or may be made of materials that are lubricious, of a pre-determined tensile strength, non-amorphous and biocompatible to all bodily secretions. The durometer of the material in the trans-sphincteric zone (e.g., the "neck region" of the receptacle) may be selected to provide comfort to patient yet provide a certain column strength to the receptacle such that in does not collapses or kinks. Various silicones and thermoplastic elastomers in the range of 10-100 Shore A have been found to optimal and reduced to practice, however harder materials may also be used with appropriately designed geometry. For example, the sheath in the trans-sphincteric zone (neck region) may be made of at least one corrugated like shape fold, such that lumen patency in maintained. For example, FIGS. 6A-6C show "corrugated" receptacles in which the outer surface includes ridges. In this example, multiple corrugated folds are formed adjacent to each other. The corrugated structures may cover at least 1% of the circumferential length and covers 100% of the circumference is the preferred embodiment. The corrugated structures may be formed such that the axis running through the corrugate is at 0-degree angle but does not exceed 89 degree angle when measure with axis running along the length of the conduit. The corrugated structure is part of the trans-sphincteric conduit such that there be more than one zone where these structures are present, and these zones can be located on the either side of or within the anal canal. The corrugated structures may be circumferential, i.e. when measured perpendicular to the axis of the conduit but can also be of elliptical shape on a planar axis or of an elliptical shape but on two planar axis that may be opposing each other, or be discontinuous and be made of multiple segments.

Figure 7A:
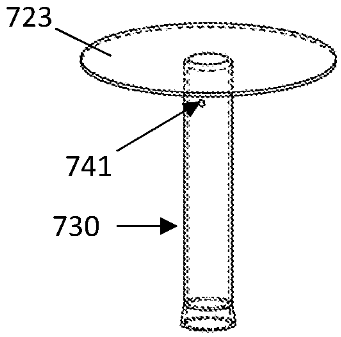
FIGS. 7A-7C show examples of receptacles including features that may be used with any of the apparatuses described herein. The receptacles in FIGS. 7A-7C include air vents (e.g., holes) that may prevent vacuum lock with the rectum.
Figure 7B:
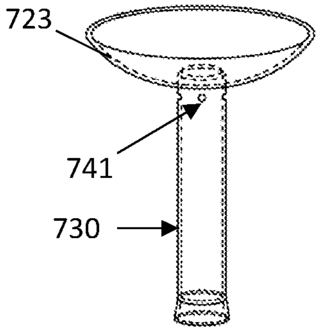
Figure 7C:
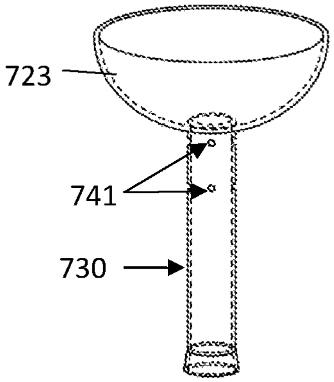

FIGS. 7A-7C illustrate examples of receptacles having air passage/release features that may be included in any of the receptacles included herein. FIGS. 7A and 7B show receptacles each including an air hole 741 positioned proximally to the cup region 723. In FIG. 7C multiple air holes, spaced apart longitudinally along the shaft 730 are shown. In some examples multiple air holes may be positioned radially around the shaft. The air holes may allow outside air into the rectal vault to prevent any vacuum lock. In some examples the air holes may be valved to allow air in but to prevent fluid or waste from leaving. The air holes may be positioned on the shaft proximal to the cup so that it is within the anal canal. These one or more holes on the receptacle may individually, or in tandem, provide a way to release negative pressure and may result in recalibration of the pressure in the suction device and release of a vacuum lock. Thus, these holes may be referred to as suction holes or pressure release holes. In some examples the pressure release holes are placed on both ends of the anal canal and designed to work in tandem (as shown in FIG. 7C). For example, the lower (more proximal) opening may be connected via a lumen within the wall of the receptacle to the upper (more distal) opening, preventing a vacuum seal. In general, the suction holes may connect to an opening outside of the patient (e.g., via an air lumen within the receptacle and/or the connector tube. The lumen may extend within the wall of the receptacle and/or connector tube or may be separate from the wall.

Thus, FIGS. 7A-7C illustrate examples of receptacles including a trans-sphincteric zone having one or more holes. Each of these holds either individually, or in tandem, provide a mechanism where there is release of negative pressure and resulting in recalibration of the pressure in the suction source and release of a vacuum lock. These holes may be placed on the portions of the receptacle in both ends of the anal canal and may be configured to work in tandem. In some examples the holes are on the corrugated features, and is placed either in line, or in an alternating manner, such that movement of this structure in any direction, results in a faster release of negative pressure from the system. A trans-sphincteric zone can be a conduit, tube, sheath, lay flat tubing, single lumen, multi-lumen or where multiple tubes are affixed together.

Figure 8A:
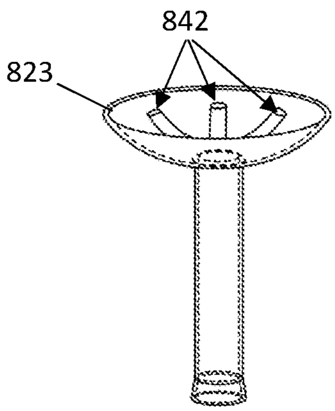
FIGS. 8A-8B illustrate examples of receptacles including features that may be used with any of the apparatuses described herein. The receptacles shown in FIGS. 8A-8B include air passages and irrigation channels and outlets.
Figure 8B:
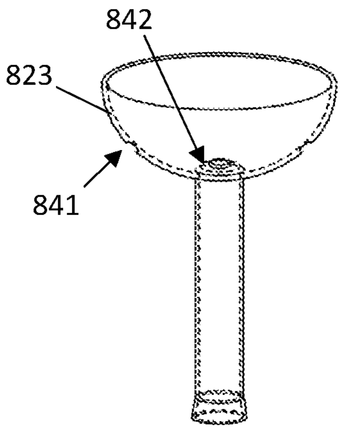

In some examples the receptacle includes both irrigation channels 842 and pressure release holes 841. For example, in FIG. 8A, the receptacle includes a plurality of irrigation channel outputs 842 integrated into the cup region 823. The irrigation channel outputs may release fluid into the rectum to help remove fecal material. In FIG. 8B the receptacle includes both an irrigation channel output 842 and an opening an air release opening 841. Thus, the outside of the cup region 823 may include one or more pressure release openings. In some examples the pressure release holes may be on the posterior part of the receptacle and/or may be connected to the fluid irrigation conduit(s) so that the fluid also provides a pushback pressure to release the tissue.

Figure 9A:
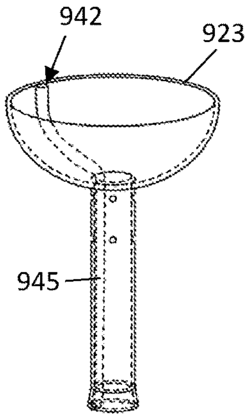
FIGS. 9A-9E show examples of receptacles including features that may be used with any of the apparatuses described herein, including irrigation channels.
Figure 9B:
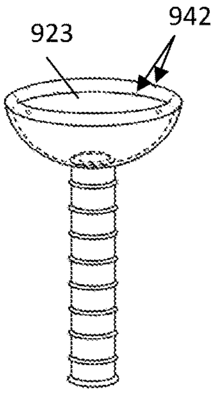
Figure 9C:
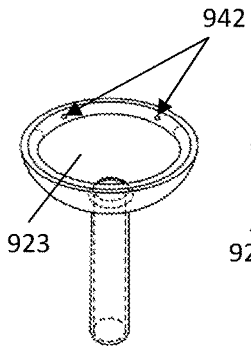
Figure 9D:
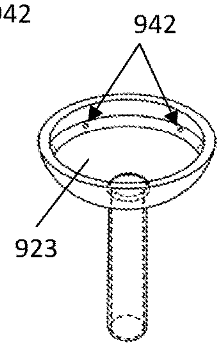
Figure 9E:
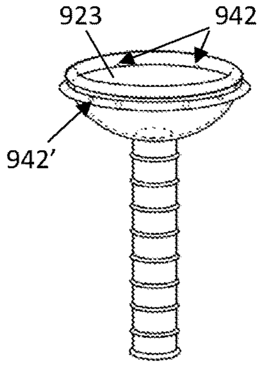

FIGS. 9A-9E also show examples of features that may be used with any of the receptacles described herein. In particular, any of the receptacles may include irrigation (e.g., one or more irrigation channels and one or more irrigation outlets) for applying fluid material into the body to help remove fecal material. The irrigation channel may be within the wall of the receptacle or external to the wall and attached to the wall. The irrigation outlet(s) may be arranged inside of the cup region, and/or on an edge of the cup region, and/or on an outer surface of the cup. For example, FIG. 9A shows a receptacle with a single outlet 942 from an irrigation channel 945 at the outer edge of the cup region 923. FIG. 9B shows an example of a receptacle including a plurality of irrigation outlets 942 around the rim of the cup region 923. The irrigation outlets may be oriented out of the (away from) the receptacle. In some examples the irrigation channels are also or alternatively oriented into the receptacle, including towards the waste channel opening. FIG. 9B shows an example in which the irrigation channel is positioned both out of and into the cup region around the distal edge. FIG. 9C shows an example in which the irrigation outlets 942 (which may also be referred to as ports) are oriented just within the lip of the cup region 923. In FIG. 9D the irrigation outlets 942 are positioned within the mouth of the cup region 923. FIG. 9E shows an example in which the receptacle includes a plurality of irrigation outlets 942' on the outer surface of the cup region as well as having irrigation outlets 942 around the distal edge of the cup region 923.

Figure 10A:
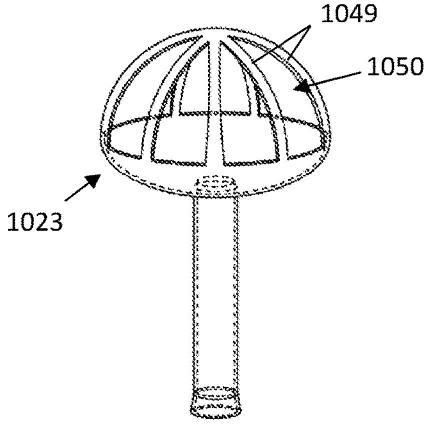
FIGS. 10A-10C show examples of receptacles including features that may be used with any of the apparatuses described herein.
Figure 10B:
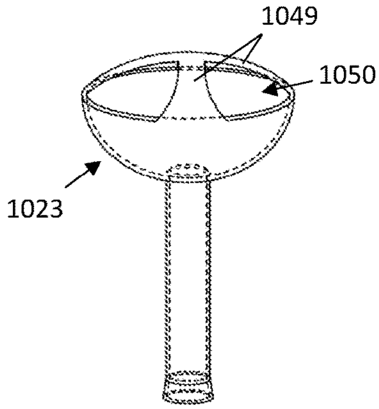

Any of the receptacles described herein may also or alternatively include a support region on the distal end of the receptacle to prevent it from collapsing or clogging. For example, FIGS. 10A and 10B show examples of receptacles in which the distal cup-shaped region 1023 is supported open by one more struts 1049. The struts may leave openings 1050 to allow fecal material to pass but may prevent blockage and may help support the receptacle in an open configuration. Excessive pressure or single point pressure in closed anatomical structures can impact blood flow at the mucosal or subcutaneous level and can result in erythema, necrosis, or similar injuries. Thus, any of these receptacles may be configured as (or may include) an internal diverter (e.g., the supports or struts 1049), which act on the distal end of the receptacle to prevent the rectum from folding into the cup and potentially causing injury. The layer can cover the entire cup or just partially cover the cup. In some examples the cup has a softer layer made of natural or artificial filaments, sintered mesh, or fish scale like design that diverts fecal material without folding the rectal mucosa into or towards the cup.

Figure 10C:
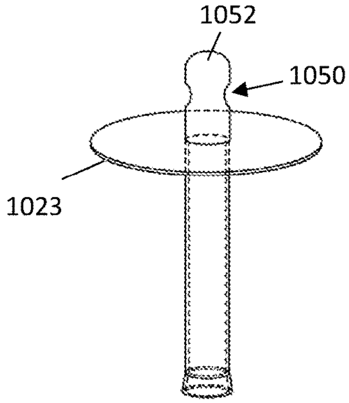

FIG. 10C shows another example of a receptacle including an internal diverter structure, projecting from just the suction (waste) inlet port. In FIG. 10C, the suction inlet is partially covered or capped by a diverter 1052 having side-facing openings. In FIG. 10C the distal end region 1023 may be flat (as shown) or cup-shaped, or any of the other shapes described herein. Any of these receptacles may include a diverter structure such as any of these shown in FIGS. 10A-10C. As suction is applied through the receptacle from a vacuum source connected on the proximal/posterior end of the cup, the distal-facing diverter may prevent contact with the mucosa and/or clogging. To improve the diversion of fecal material that is more viscous or lower on the Bristol Stool scale, the vacuum pressure be increased (e.g., over 50 mm Hg) and/or the size of the vacuum tube may be increased. The distal tip of the vacuum source may therefore be defected by the diverter away from the mucosa. The diverter may also provide multiple openings through which suctioning can occur in the event one of the openings gets clogged.

Figure 11A:
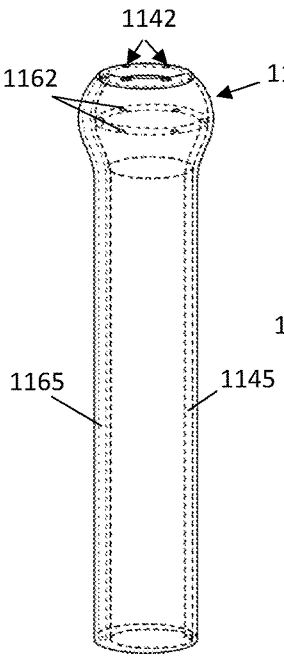
FIGS. 11A-11D show examples of receptacles including features that may be used with any of the apparatuses described herein. The receptacles in FIGS. 11A-11D include both air and fluid outlets.
Figure 11B:
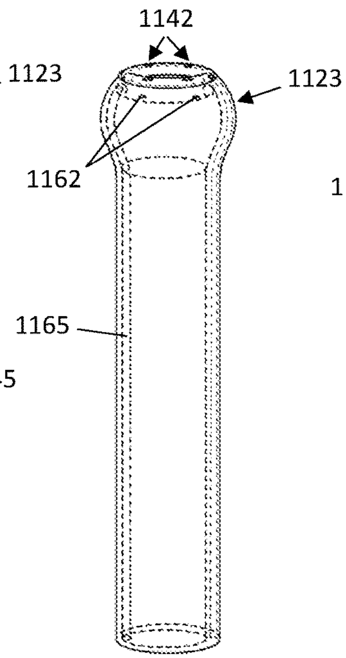
Figure 11C:
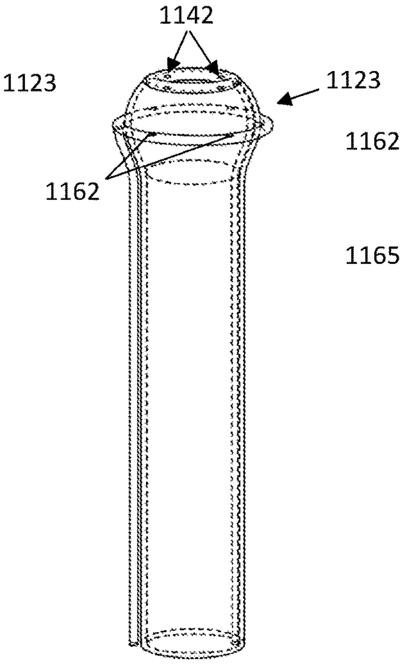
Figure 11D:
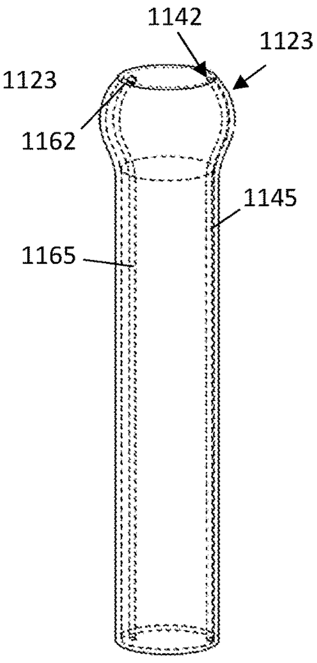

FIGS. 11A-11D illustrate alternate designs for receptacles with both air and fluid outlets that include features that may be used in any of the receptacles described herein. In FIGS. 11A-11D the distal end region 1123 of the receptacle is cup shaped but may have a smaller diameter than the larger cup-shaped examples shown in FIGS. 3A-10C. Further, the distal end has a bulb-like configuration in which a distal opening provides access into the central suction (waste) lumen). These examples may also include one or more fluid outlets 1142 (connected to a fluid line/irrigation channel 1145) as well as one or more air outlets 1162 (connected to an air channel or line 1165). For example, FIGS. 11A-11B a plurality of irrigation (fluid) outlets 1142 are arranged along the upper distal face of the distal end region of the receptacle and a plurality or air outlets 1162 are arranged within the inside of the distal end region; in FIG. 11A they are arranged circumferentially and slightly proximally from the distal end while in FIG. 11B they are arranged circumferentially more distally. The air outlets and irrigation (fluid) outlets may be switched, in any of these examples, so that the air outlets are more distal than the irrigation outlets. Alternatively, air outlets and irrigation outlets may be arranged at the same longitudinal level (e.g., all distally arranged around the outer perimeter, as shown in FIG. 11D). In FIG. 11C the air (or alternatively fluid) outlets are arranged circumferentially around the outer surface of the distal end (e.g., cup) region of the receptacle. The air channel (or alternatively fluid/irrigation channel) may be arranged on the outside of the receptacle as shown in FIG. 11C.

Figure 12A:
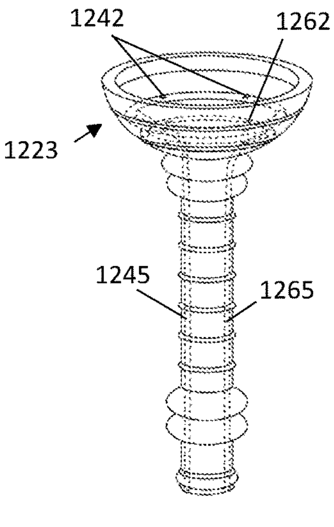
FIGS. 12A-12B illustrate an example of a receptacle including features that may be used with any of the apparatuses described herein, showing both air and water (irrigation) channels.
Figure 12B:
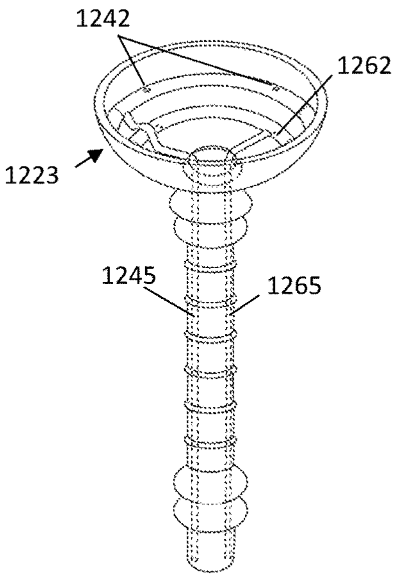

FIGS. 12A and 12B also illustrate an example of a receptacle having both air 1265 and water/irrigation 1245 fluid channels and air outlets 1262 and irrigation outlets 1242. In FIGS. 12A and 12B the air outlets 1262 and the outlets for fluid 1245 (e.g., irrigation) are located within the distal end region (e.g., within the cup region 1223). The air outlets are shown more proximally within the cup region than the irrigation outlets; this configuration may be reversed, with the irrigation outlets more proximally located relative to the air outlets. FIG. 12B shows a perspective view into the distal end region of the apparatus of FIG. 12A.

Any of the apparatuses descried herein may include sensors for monitoring the status of the patient and/or the status of the apparatus. For example, the apparatus may include receptacle that has one or more sensors for detecting: pressure, flow, temperature, pH, and/or waste volume. Theses sensors may be electrically coupled via one or more wires that extend along the connector tube and/or receptacle to the apparatus outside of the patient anatomy; alternatively, the one or more sensors may be coupled wirelessly. These sensors may be configured to read and transmit physiological parameters like intra-rectal pressure, radial pressure (e.g., on the receptacle), capillary compression, muscle motion, temperature, and volume of the rectal vault. The readings of these parameters may aid in either a manual or automatic trigger to calibrate negative pressure, positive pressure, fluid flow, cycle time, hold time or reset of the system. For example, the controller within the apparatus may receive the one or more sensor inputs and may process sensor data, e.g., may amplify, filter, sample, including digitally sample, an analyze the sensor data. The controller may include one or more processors and/or circuitry for performing the analysis.

As mentioned above, the receptacle may be applied to the patient's anatomy for the purpose of collecting and diverting fecal matter in a variety of ways, either or both external to the body, e.g., using an adhesive, strap, gravity reliant flat pad, wrap-around garment, or two-way attachment mechanisms like Velcro, double-sided tapes, magnets or crystalizing/fast cure chemicals, and/or by internally retaining the receptacle, e.g., using an expanding, such as a self-expanding and/or inflating member.

When the receptacle is inserted either inside the patient's body or on the anal verge, the receptacle may be applied using finger digital insertion of fingers or mechanical constructs (e.g., applicators), in singular or plural forms, that rely on push, pull, rotate, twist, peel, and sliding mechanisms. Insertion apparatus may also include mechanisms in which activation is triggered by an external device. These apparatuses may include, for example but not limited to, inflation devices, telescopic devices, devices that function on the principles of an Iris or a ratchet, linear or horizontal screws, etc.

In some examples, the receptacle may be compressed by folding. A foldable receptacle may be digitally inserted past the anal canal. For example, the receptacle may be folded in a FIG. 8 formation, and then folded over a second time to create a cylindrical shape, that can be inserted in the anatomy. The two folds can further be manipulated to also form a torpedo-like structure to ease the insertion of the receptacle.

In some examples, the receptacle may include pocket to hold the care-givers finger (e.g., an index finger) to standardize insertion technique, and/or to maintain hygiene for the caregiver and to provide a tactile confirmation while inserting the receptacle. The pocket can also be used in conjunction with an applicator structure to insert the receptacle.

The external application and securing mechanisms can be configured in various shapes like circular, horse-shoe shaped (U), cross U shape where both vertical arms overlap, oval and other shape that contour along with the pelvic-buttock anatomy. Materials like derma friendly tapes, adhesives, silicon or colloid based adhesives that can be used over follicles, breathable, moisture absorbing, fluid channeling, material designed with modified surface properties, that facilitate the anchoring, affixation, collection and diversion of fecal material, can be used.

For example, a silicon-based adhesive that houses the receptacle, and subsequent suctioning paraphernalia, may be used to adhere to the outside of the anorectal anatomy. The adhesive is applied to cover the anal opening, perineum and on the buttocks of the patient. The adhesive has multiple layers, where the layers extent towards the receptacle and provide a specific clinical and ergonomic function. Collectively the adhesive is designed to be skin friendly, easy to apply and peel off, works over hair follicles and is not painful to peel off, is moisture resistant, breathable and flexible. For example, an adhesive may be configured in the shape of two palms touching each other with thumbs and fingers pointing in opposite direction. The periphery of the adhesive may be shaped to act as a strain relieve mechanism. In one example, the adhesive may be configured with an infection control agent like silver.

In some examples a garment may be used in conjunction with the apparatus, and particularly the receptacle. For example, a diaper- or underpants-like garment can be used to hold the receptacle close to the anal opening. The garment may also reduce or prevent leakage and odor. The receptacle can be inserted into a customized pocket for placement or in some examples can be held in place by applying pressure. In one example, the applicant's skin may be lubricated and/or treated with an anti-bacterial/anti-microbial agent to prevent or reduce infection.

Any of the apparatuses described herein may be used with a deployment tool to help deploy the receptacle, particularly when the receptacle is deployed for anchoring within the rectum. The apparatuses described herein may be used with one or more insertion rods that may use a longitudinal pushing element. An insertion rod can include single or of multiple parts, wherein may perform different functions. For example, a two-part applicator may include an internal plunger or pusher that pushes the receptacle, which can then be retrieved by either pulling the back the outer tube first, deploying the receptacle, and then removing the internal plunger or pusher. In some examples the applicator may include an outer tube that is perforated along a pre-determined axis to deploy the receptacle and then remove an internal pusher or plunger. In some examples the applicator may include an outer tube that is not a complete circle but includes an open surface through which an internal pusher or plunger can be slid out of once the receptacle is deployed.

Thus, a receptacle can be digital inserted in the patient anatomy, e.g., using an index finger, and/or with the assistance of a deployment device, which may include a mechanical pusher, fluidic forces, or mechanisms where kinetic forces are transferred from outside the body to inside the body. In some examples an inflation device can be used as applicator. The inflation applicator can either be a stand-alone system (barrel, plunger, and fluid) or a system that is integrated with the vacuum source and/or fluid pump of the apparatus.

In some examples, the deployment tool may include a cylindrical member that contains the receptacle in a compressed/constricted configuration. The deployment tool may then be inserted into the anal canal with a relatively small profile and manually or automatically actuated to drive the receptacle out of the deployment tool to expand, including self-expand, into the deployed and anchored configuration. The deployment tool may include a shell that is removed (e.g., in two or more parts) over the deployed receptacle without disturbing the receptacle. In some examples the deployment tool may include or be formed of a biocompatible material that may be left in place.

In some examples the receptacle may be formed of a bioresorbable material. For example, the receptacle may be used without a separate deployment tool but may be held in the compressed configuration by a bioresorbable material that constricts or constrains it to a narrower configuration that may be more easily inserted. Upon deployment the bioresorbable material securing the receptacle may dissolve or break, releasing and deploying the receptacle. In some examples the receptacle may include or be formed (at least in part) of a bioresorbable material that may be configured to breakdown after a predetermined period of use (e.g., 1 to 29 days), so that a withdrawal mechanism only needs to be used if the patient gets discharged sooner than day of degradation. PGA or similar materials can be used for the bioresorbable material. For example, an outer tube of an applicator may be made of a bio- or water-degradable material that dissolves once in contact with rectal mucosa and exposes the receptacle at the desired location.

In some examples an indwelling receptacle can be an indwelling structure that can be inflated with fluids and may include an anchoring region (e.g., at the distal end region and/or a more proximal region configured to sit outside of the anal passage) shaped like a sphere, cuff, doughnut, squared, circular or tubular sleeve, or in the form of an elliptical, spherical disc. In some examples the inflatable structure may reside within the rectum and may be made of either an amorphous or semi-crystalline polymer and its molecular orientation is customized to aid safe retention inside the anatomy. In some examples, the apparatus may include a polymer for an inflatable cuff that is relatively soft (e.g., has a shore durometer of between 10 and 100 A).

In some examples portion of the receptacle that is configured to reside within the body (e.g., the anal cavity and/or the rectum) can include one or more internal structures that open or close, either partially or completely. For example, any of the receptacles described herein may open or close to a fixed form or a compliant form. Fixed form structures may include an expanding (e.g., irising or dilating) portion that can be open and close to a predetermined amount. For example, a telescopic tubular fixed form mechanism may be used for the receptacle. In some examples the controller may control the amount that that the receptacle is "open" or "closed" along the primary lumen (e.g., suction lumen).

Any of the receptacle described herein may include one or more pads, wicks, gels, woven or non-woven fabrics, natural fibers, and/or mop or broom like filaments that use capillary force-based transmission as part of the receptacle. Any of the receptacles described herein may include suctioning and/or diverting flows from a distal end towards a proximal end, ending in a collection chamber of the apparatus, such as a collection bag.

In some examples, the receptacle, and particularly an internal region of a receptacle, may be configured to collect/divert fecal matter, as well as to break-down the fecal matter in smaller particles. This may be accomplished by one or more of grinding, compression, squeezing, surface abrasion, filtration, chemical or thermal decompression, or by vibration. For example, the internal wall of the receptacle may be modified to break down the fecal matter by sending the flow of fecal matter down a pre-determined path at relatively high velocity; the path may be lined with one or more protrusions and indentations in the form of spikes, ribs, cavities, bulbs, etches, etc. In any of these examples, the region for breaking down the fecal matter may be heated; for example, protrusions and indented features within the internal path region may be heated to further assist in breaking down the material. In some examples a multilayered filtration system may be used to loosen the fecal matter and the filtered material may be either exchanged/replaced in a cassette within the apparatus (e.g., within the housing) or it may be flushed or washed out.

In some examples the receptacle may be deployed by using suction, including the suction of the apparatus. For example, suction may be used to pull back a casing (deployment casing) to deploy the receptacle in the anatomy. The pullback force may be created by applying differential pressure in the two parts of the application, so that there is a higher negative pressure existing on longitudinal axis coming out of the anatomy, deploying the receptacle.

As mentioned, any of the deployment devices described herein for deploying a receptacle may include a mechanical mechanism such as an iris, scissor, telescoping tube, ratchet, or spirometer-like mechanism to deploy the receptacle past the anal canal and towards the posterior part of the rectum.

In general, any of these apparatuses, including the receptacle and/or the applicator, may be used with lubrication. For example, the applicator may be coated with lubricant. Thus, the applicator may be coated and/or dipped in a clinical grade lubricant before insertion. In some cases the lubricant may have a small dosage of a local anesthetic.

As mentioned above, the receptacle may be delivered in a compressed form using one of the application methods described above and may be withdrawn from the anatomy after use. For example, a receptacle that is substantially circular in shape with a diameter of 5 mm, or larger, may be disoriented and removed from the anatomy by application of forces near the transit conduit. For example, the forces may be transferred longitudinally along this conduit, which in turn disorients the receptacle to a linear form and can be moved out of the anatomy.

In some examples, the receptacle may be removed from the anatomy by deflation or collapse of at least a portion of the receptacle, such as by puncturing the receptacle, collapsing, folding or rolling the receptacle before being removed from the anatomy. In some examples the receptacle may include a wrap-around mechanism that operates similar to a draw-string purse and may be configured to return the receptacle to a collapsed configuration. For example, the draw-string configuration may collapse the receptacle for retrieval but may use a unidirectional ratchet like lock-in using gears, frictional forces, mechanical blocks, or free-flowing draw strings that relies of the user's physical force to collapse and retrieve the receptacle. Other withdrawal mechanisms may include peel-away adhesives, rebalancing the negative pressure to assist in removal of the product, activation of bioresorbable agents, and unwinding of tethers, tapes, or other support systems to facilitate the removal of receptacle away from the body.

FIGS. 13-16B illustrate examples of housings, which may be referred to as cannisters, that may be used with any of the apparatuses described herein. For example, a housing may be rigid or semi-rigid and may be configured to enclose and protect the components of the apparatus, such as the electronic and mechanoelectrical components, e.g., controller, vacuum pump, fluid pump, power source, etc. For example, the apparatus may be configured to secure the components in a fluid- and vapor-impermeable manner. The housing may also be configured to make connections, including releasable but sealing connections with one or more containers for collecting fecal matter (e.g., collection bags) and/or fluid reservoirs. The housing may also make secure and sanitary connections to the connecting tube(s) that are continuous with the receptacle. In some examples the housing may also include an intermediate collection region, which may be within the housing (e.g., partially or completely enclosed within the housing). The housing may also include inputs (e.g., buttons, controls, etc.) and outputs (e.g., displays, speakers, LEDs, etc.).

Figure 13:
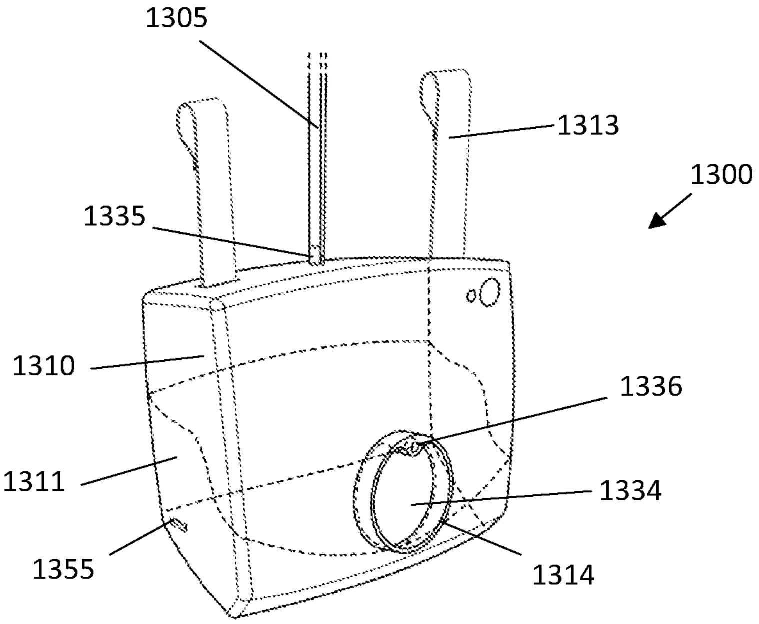
FIG. 13 shows one example of a housing (e.g., cannister) portion of an apparatus as described herein.
Figure 14:
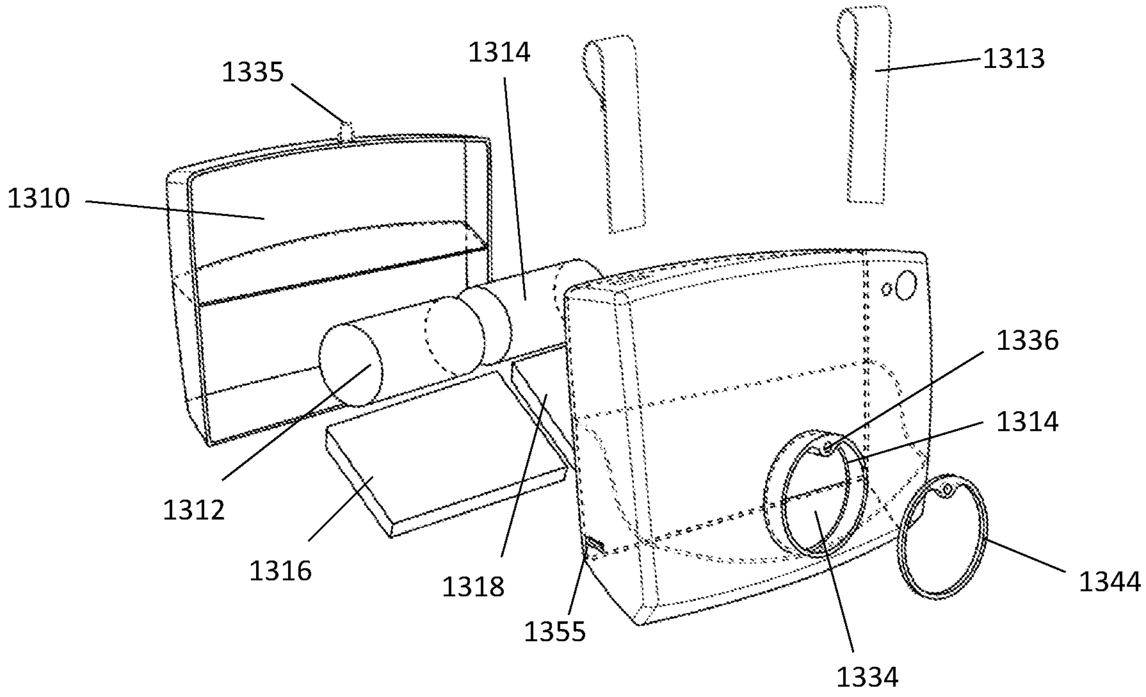
FIG. 14 shows an exploded view of the housing (e.g., cannister) of FIG. 13.

For example, FIGS. 13, 14, 15A-15B and 16A-16B illustrate examples of a housings or cannisters that may be used as described herein. The cannister may be configured as a portable canister unit that is configured to be suspend by the bedside. The cannister 1300 may include straps, handles, or the like 1313, as shown in FIGS. 13 and 14. The cannister may include an intermediate rigid chamber to hold vacuum; since a flexible bag that is directly connected to a vacuum will collapse, any of these apparatuses may include a small rigid chamber 1310. Once negative pressure is activated, all fecal material from the receptacle may be collected in the intermediary collection chamber 1310 first, and then may move to the disposable bag (not shown in FIGS. 13-14) through a bag connection interface 1314 on the outside of the cannister, under gravity after the vacuum is turned off. In some examples rectal waste can alternatively or additionally be collected directly in a larger rigid canister, which may be disposable or washable (and in some examples may be lined with a flexible disposable bag). The cannister may also include a second chamber that holds the vacuum pump 1312, irrigation pump 1314, battery 1318, controller 1316 and other electronics.

A canister may include ports for connection of transit conduit and irrigation fluid, an on-off switch, displays for various parameters, an interface that houses the pump(s), power source, and programmable relays, an intermediary flow chamber, and connection to a disposable collection bag and fluid reservoir.

The intermediary chamber may be configured such that the fluid flows to the chamber and then flows into a disposable collection bag(s). The chamber may be made of a semi-crystalline polymer, and may include flow-enhancing channels, a lubricious coating, and an outlet that is designed to be unidirectional to both flow of fluids and fecal material. The intermediary hold chamber may include a sensor to detect that the chamber is full, or nearly full; for example, the apparatus may include a float valve, a hydrophobic cut-off valve or an electronic sensor, that is configured to signal when the chamber is full. In some examples the intermediary chamber has a flow-meter, to measure total output of fecal material. In some examples the intermediary chamber may have an internal pressure that is lower or different than the transit conduit and may be configured to withstand the pressure demands (e.g., of the lower pressure). The intermediary chamber may have an internal pressure that is different when compared to the disposable bag. The intermediary chamber may have an inlet from where fluid or vapor-based disinfectants can be inserted to clean the chamber.

The intermediary chamber may be coupled to a quick connect, disconnect port on the housing (cannister) that may be used to collect fecal material in a leak-proof manner. The collection bag may have an interface that slides, encapsulates, and/or mates with the outlet in the intermediary chamber and provides for an odor-proof, leak proof connection.

The canister may be configured to be soundproof by insulating the internal walls using foam, neutral zones, or a similar mechanism. The canister may also be formed of a material that is significantly shatter proof and leak-proof.

In some examples the canister may be connected to a rigid container that acts as an intermediary chamber but may be adjacent to the canister, and the material may be manually emptied from this rigid container to a disposable collection bag. The canister may be ergonomic, consumer friendly and configured to be hung of the bed, wheelchair, surgical bed, or a fluid pole.

The canister may also include a mechanism that shuts off the vacuum source in case the canister gets full. The shut-off mechanism may be configured so that the vacuum source is not reactivated until the canister is completely or sufficiently empty.

In the example shown in FIGS. 13 and 14, the apparatus includes a connection 1335 to the connecting tube 1305 that is continuous with the receptacle. In this example the apparatus includes a link both to the irrigation line and the waste collection line in the connecting tube. In some examples the connecting line may also include an air lumen which in some examples is connected to an air pump or source of positive pressure. In FIGS. 13 and 14, the canister includes a split internal compartment, a first compartment 1311 to house the electronics, and a second rigid compartment 1310 to receive the rectal effluents. The cannister may also include connections to hanger straps, one or more bag connectors 1314 and I/O interface 1355.

FIGS. 13 and 14 also show a connection for attachment of a dual bag that holds both a supply of irrigation fluid (e.g., water) and to a separate waste storage. The larger opening 1324 of the connector is for waste storage and the smaller opening 1326 is for irrigation fluid. The opening may include a sealing ring 1344.

The arrangement of components in FIGS. 13-14 is exemplary only. Other shapes and configurations of the cannister (housing) may be used, including using wall suction rather than including a suction pump. For example the housing may include a connection line for connecting to a source of wall suction, and the controller may control one or more suction adapters (including valves, manifolds, etc.) to adjust and control the suction applied to predetermined levels and pattern. A suction adapter may also be used when the apparatus includes a suction pump and may be within the housing or outside of the housing. In general the components within the housing may be separated. In some examples a separate source of irrigation fluid may be used (as shown in FIG. 1B); the housing may then include separate connectors and the like.

Figure 15A:
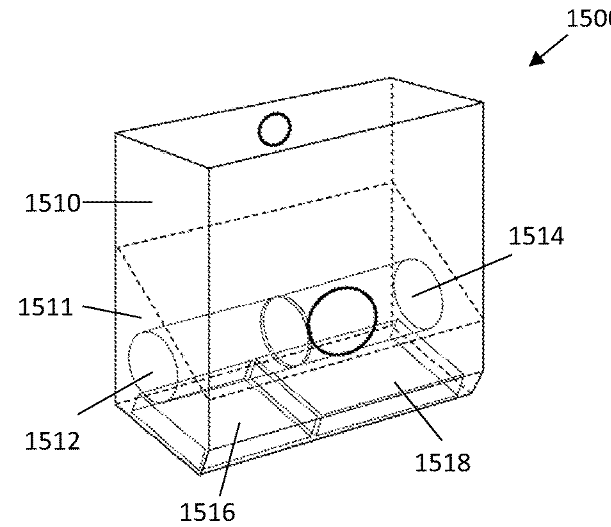
FIGS. 15A-15B show examples of housings (e.g., cannister) having features that may be used with any of the apparatuses described herein.
Figure 15B:
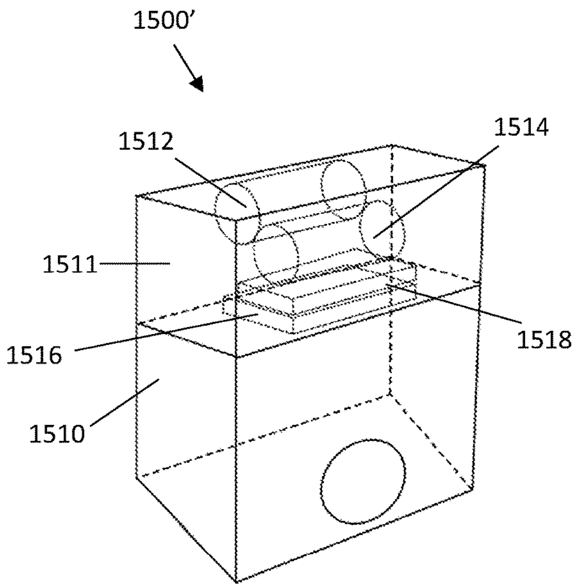

FIGS. 15A, 15B and 16A-16B illustrate other examples of housings 1500, 1500' (cannisters) having features that may be used in any of the apparatuses described herein. For example, In FIGS. 15A and 15B the two cannister includes two chambers (e.g., an electronic chamber 1511 and a waste collection chamber 1510) that are oriented in different orientations to achieve the same end outcome. In FIG. 15A the rigid waste collection chamber 1510 is on the top, above the electronics chamber 1510, while in FIG. 15B the rigid waste collection chamber 1510 is on the bottom, below the electronics chamber 1510. The electronics chamber in this example holds the electronics (e.g., controller, circuitry, etc.) 1516 and battery 1518 as well as the suction pump 1512 and irrigation pump 1514. Since the waste storage bag is filled by gravity driving fecal waste material from the rigid waste collection chamber into the bag, it may be beneficial to include the waste storage chamber on the upper surface.

Any of the apparatuses described herein may include a source of vacuum (e.g., vacuum pump), including within the housing or separate from the housing. For example, a vacuum pump may be a 3.7V diaphragm pump which can generate up to 450 mmHg negative pressure. In some cases the same vacuum pump may also be used to apply positive air pressure; for example, discharge from the vacuum pump may be used to inject air though an airline. Or in some case another pumps may be used.

These apparatuses may also include an irrigation pump (such as a water pump). For example, a 3.7V diaphragm pump may (which can generate an output head of around 3 m) may be used. The irrigation pump and vacuum pump may be small, compact, and lightweight. And may be enclosed within the cannister (e.g., housing) or may be external.

The apparatuses described herein may generally include one or more valves and valve controls for directing the application of negative pressure (suction) and/or controlling the level of negative pressure, for pumping irrigation fluid, etc. For example, these apparatuses may include one or more solenoid valves, such as (but not limited to) 3V solenoid valves to control the fellow of vacuum, air and irrigation fluid (e.g., water).

Any power source may be used, including a battery (e.g., rechargeable battery). For example, a battery may be a 5000 mAh Li battery, which may power all of the included components (e.g., pumps, valves, controller, etc.). The controller may also include one or more clocks, processors, memory and the like. The controller may also include or couple to a charging circuit, which may be used to charge the battery.

Figure 16A:
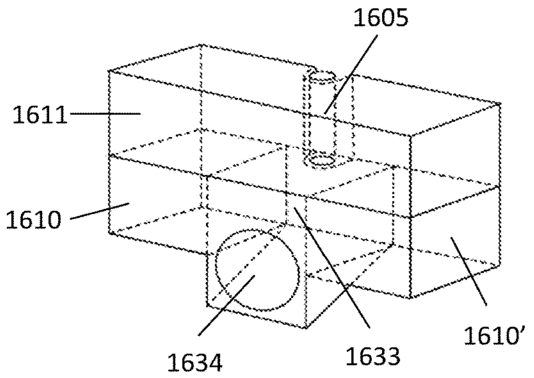
FIGS. 16A-16B show an example of a housing (e.g., cannister) having features that may be used with any of the apparatuses described herein. The cannister shown in FIGS. 16A-16B is modular.
Figure 16B:
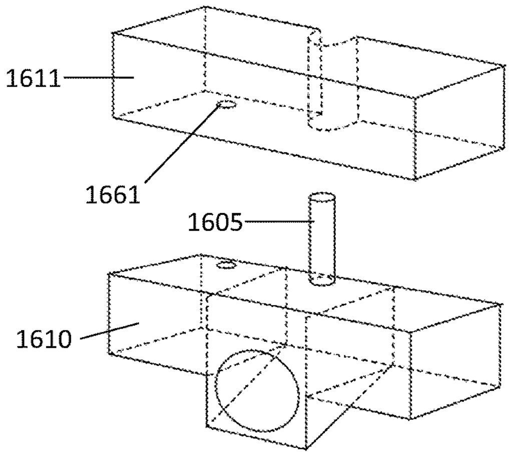

Any of these cannisters may be modular, and in particular, may allow for removal (and disposal or sanitizing) of the rigid waste collection chamber portion, which may allow for reuse of the electronics portion. For example, FIGS. 16A and 16B illustrate an example in which the cannister is modular so that a rigid waste collection chamber 1633 is on the bottom portion, and includes two electronics chambers 1610, 1610' (e.g., holding the controller, pump(s), valves, etc.). The upper portion 1611 may be configured to hold irrigation solution (e.g., water) and may be refillable. The two portions may be secured together during operation but separated from each other (as shown in FIG. 16B) for cleaning, refilling (e.g., of irrigation solution) and the like. In FIG. 16A the chambers are shown coupled together (and may be secured together by a latch, lock, etc.). The two may include multiple connections to connect 1661 the source of positive or negative pressure (e.g., vacuum) from the electronics chamber into the rigid waste collection chamber and/or irrigation solution. The rigid waste collection chamber includes the connection 1634 to the waste collection bag (not shown) and is shown coupled to the connecting tube 1605 (or a connector for the connecting tube). Alternatively, in some examples the rigid-walled waste collection chamber (internal waste collection chamber) may be removable for cleaning, etc. The housing (cannister) may include one or more seals between the regions for preventing leaking, maintaining pressure, etc. For example any of these apparatuses may include sealing rings (e.g., O-rings, etc.) between the components, including between the housing chambers, between the housing and the external collection chambers (e.g., bags), etc.

As mentioned above, any of the apparatuses may include a source of vacuum or may couple to and control an external source of vacuum (suction). Vacuum forces are commonly used in healthcare settings to suction out various bodily secretions. The use of vacuum varies from bedside to operating rooms or even in patients' domestic environments. Clinical care related to suctioning of intubated patients, tracheostomy patients, suctioning of pleural effusion, in procedures related to dentistry, neurosurgery, fluid management at surgical sites, endoscopy, colonoscopy, and wound care are considered safe, efficacious and commonly used. The vacuum pressure in these procedures ranges from 10-500 mm Hg and based on application can be provided from in-line central wall vacuum sources, portable vacuum sources like electric or mechanical or manual powered pumps, gas- or water-powered venturi suction units, bellows, squeeze bulbs, etc.

Figure 17A:
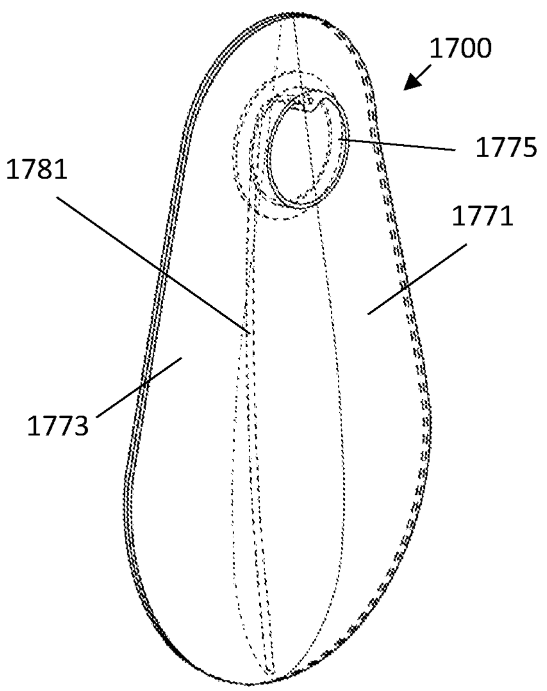
FIGS. 17A-17B illustrate an example of a collection chamber (e.g., bags) that may be used with the apparatuses described herein.

FIGS. 17A-19E illustrate examples of collection bags (e.g., disposable/removable collection chambers) that may be used. The collection bag may be a dual collection/irrigation source bag in some examples. Thus, any of these collection bags may include two compartments, one for stool collection and other for water storage, that may be arranged in a variety of configurations. For example, FIGS. 17A-17B show one variation of a collection bag 1700 in which the bag includes front/back sides for holding irrigation fluid (which may be sterile) 1771 and collection of fecal material 1773. FIG. 17A shows the front view, while FIG. 17B shows the rear view of the collection bag. The bag includes a liquid and gas-impermeable container (which may be formed of multiple layers) that include a connector interface 1775 that may securely connect to the canister. The fecal collection region may be larger or the same size as the irrigation fluid containing side. The irrigation fluid may be per-filled into the bag, while the fecal material containing side will be empty. The connector 1775 may include a connection for both the larger chamber to receive fecal material, and a smaller connector for coupling to the source of irrigation fluid. The connection to the source of irrigation fluid may be closed (e.g., sealed) and may be opened by connection to the connector on the housing. For example, the connection to the source of irrigation fluid may be covered by a frangible material (e.g., foil, etc.) that may be manually removed or pierced when connecting. The connection between the bag and the housing may be friction fit, and/or it may include a locking component to avoid accidental disconnection. In some cases the connector may be threaded. The irrigation side of the bag may also include a tube 1781 or another channel to couple into the chamber. For example, the irrigation chamber may include a tube running from the bottom of the compartment to the interface connector (shown in dotted lines in FIGS. 17A-17B).

Figure 17B:
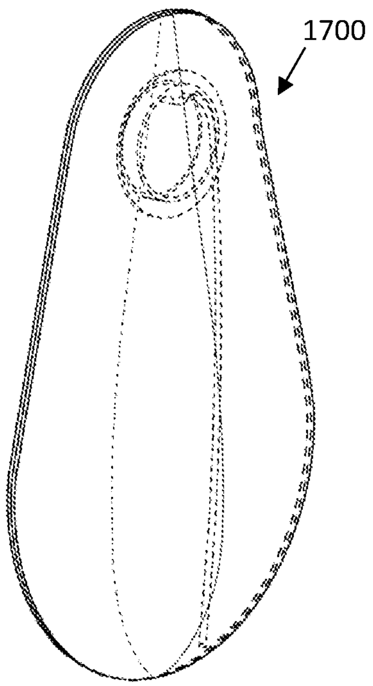
Figure 18:
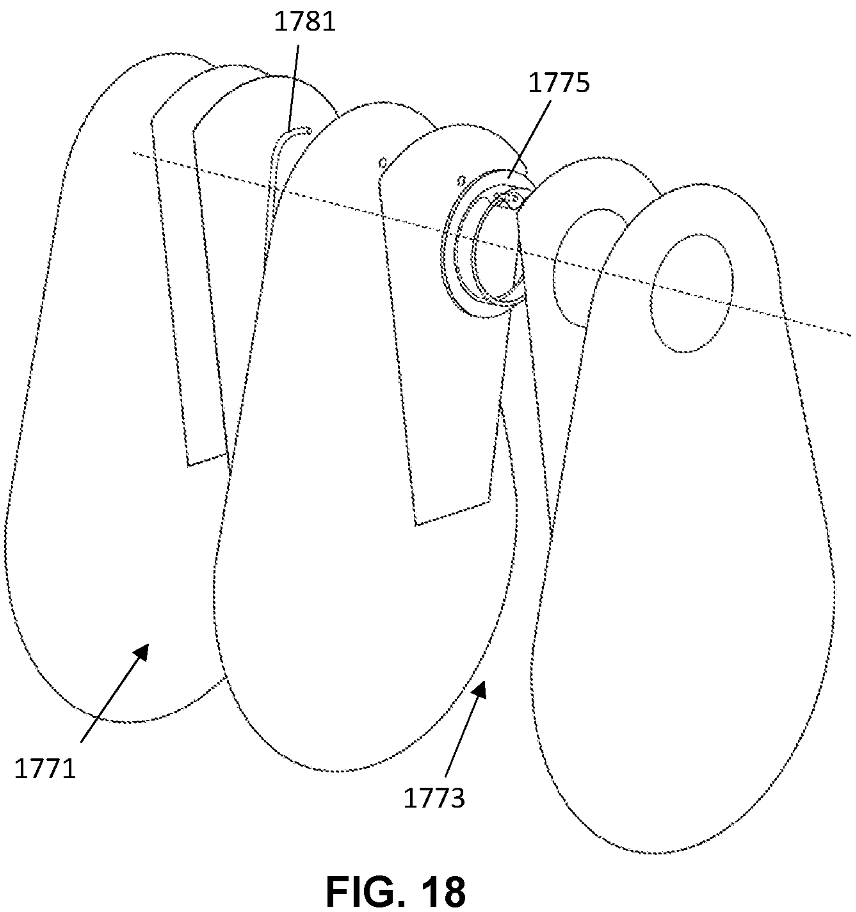
FIG. 18 shows an exploded view of the collection chamber (e.g., bag) of FIGS. 17A-17B.

FIG. 18 shows an example of an exploded view of the collection bag of FIGS. 17A-17B. The irrigation fluid 1771 back region of the bag may be formed by the outer (back) sheet and an inner sheet, while the front fecal material collection region 1773 may be formed by the front sheet and an intermediate sheet. Any of the external collection chambers (collection bags) described herein may include a valve at the inlet (or inlets in the case of dual bags). For example, a flutter valve may be included at all or some of the inlets to prevent backflow and subsequent leakage. For example, a flutter valve in the stool compartment may also prevent communication between the disposable bag and the stool chamber in the canister when vacuum is generated, which may prevent backflow from the stool compartment of the collection bag into the stool chamber of the canister.

In general, the bags may be single-use, which may prevent nosocomial infections. A disposable bag that is at least 200 ml in volume is highly desired by the care providers. The bag may have a volume of greater than 200 ml (e.g., 300 ml or greater, 400 ml or greater, 500 ml or greater, 600 ml or greater, 700 ml or greater, 800 ml or greater, etc.). In some examples the bag may be a flexible bag that is made of two or more layers of olephins, acetates and chlorides that results in a structure that is leak proof and may also be odor proof, has features that enable easy and leak-proof connect-disconnect features, and is designed in a way where the nurses can visualize, record and monitor fecal material.

The bag may operate in combination with the vacuum pump to creates a differential pressure that enables the flow of fecal waste material and prevents the bag from collapsing or creating a vacuum lock. The disposable bag may have a separate fluid reservoir that can be filled by the nurse/user on a regular basis. The reservoir is connected to a fluid pump by way of a rigid or flexible conduit that is kink resistant.

In some examples the bag may include has small aperture for visualization for material but may otherwise be either opaque, translucent, or such that it does not impact patient dignity. The bag may be made of polymeric blend or co-extruded or laminated such as EVA/PVDC to contain odor. It may have a pocket to house charcoal filter assembly to facilitate the release of flatus; and has a load cell or scale for effective output measurement.

Figure 19A:
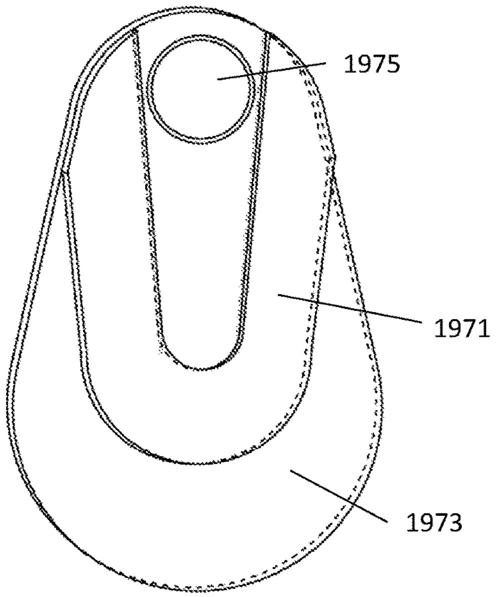
FIGS. 19A-19E illustrate examples of collection chambers (e.g., bags) having features that may be used with any of the apparatuses described herein.
Figure 19B:
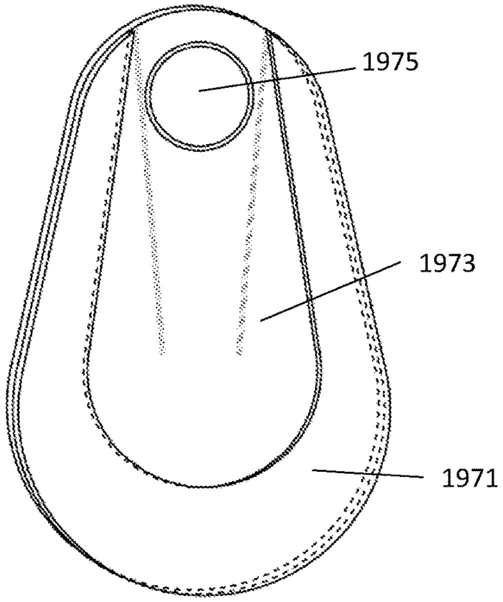
Figure 19C:
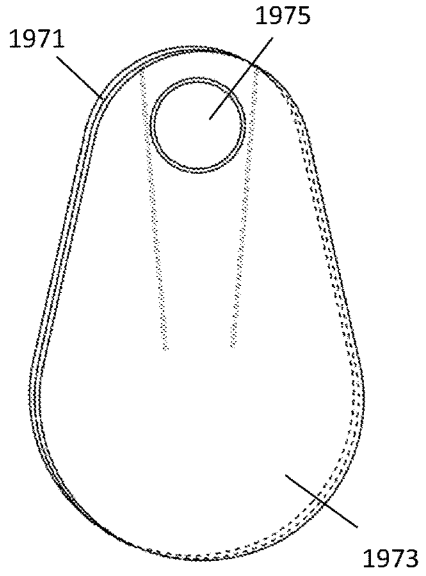
Figure 19D:
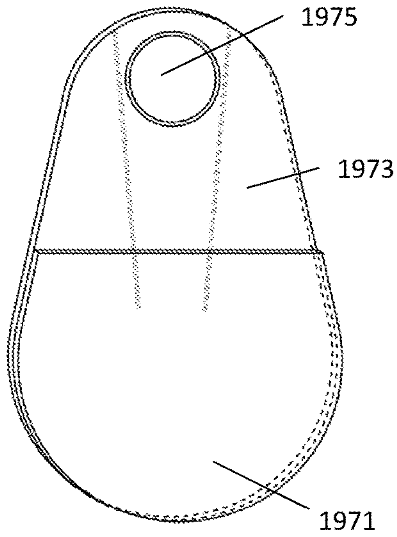
Figure 19E:
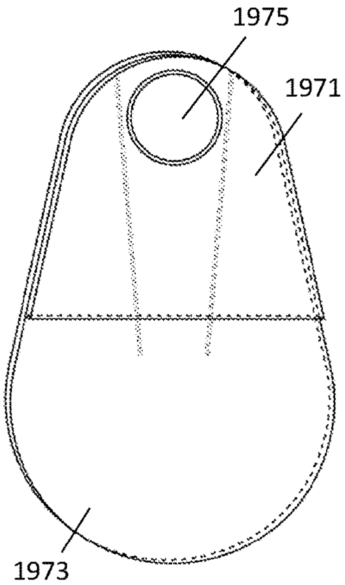

FIGS. 19A-19E illustrate different configurations of collection bags, each of which includes both a fecal material collection region 1973 and an irrigation fluid source region 1971. The bags also include a connector 1975. FIG. 19A shows a bag with an upper chamber 1971 holding irrigation fluid and a U-shaped lower chamber for holding fecal material 1973. FIG. 19B shows the reverse configuration, having a U-shaped lower chamber 1971 holding irrigation fluid and an upper chamber for holding fecal material 1973. FIG. 19C shows a bag similar to that shown in FIGS. 17A-17B with a back chamber 1971 holding irrigation fluid and a front chamber for holding fecal material 1973. FIG. 19D shows an example with a larger chamber (extending from the upper to lower ends of the bag) for holding fecal material 1973 and a lower chamber 1971 for holding irrigation fluid. FIG. 19E shows another example with a larger chamber (extending from the upper to lower ends of the bag) for holding fecal material 1973 and an upper chamber 1971 for holding irrigation fluid.

Figures 20A, 20B, 20C, 20D:
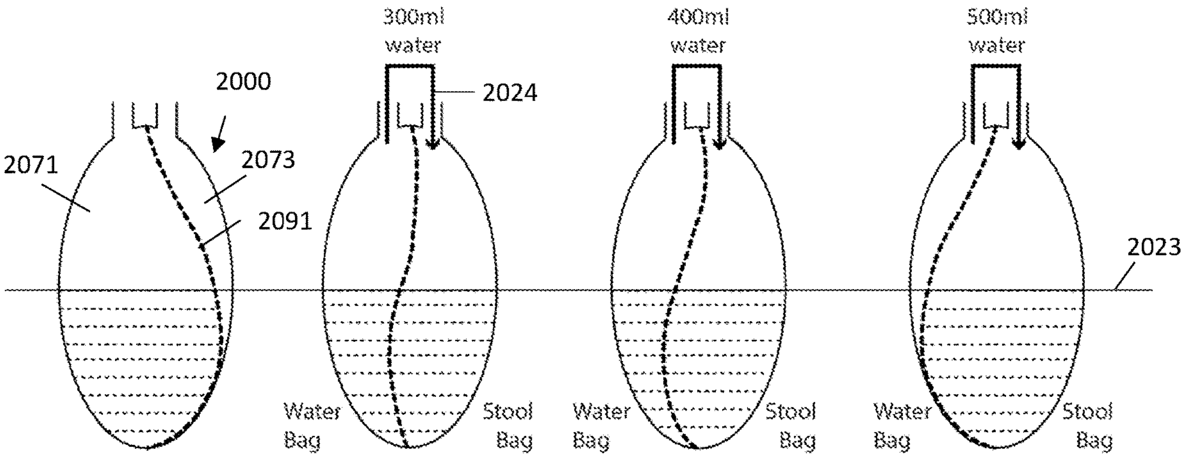
FIGS. 20A-20D illustrate the operation of a collection chamber (e.g., bag) in an example of an apparatus as described herein.

In some examples it may be advantageous to use a collection chamber (e.g., bag) includes both the source of irrigation material and the chamber for collection of fecal matter, both for ease of use and reduction of parts, but also because this configuration may allow easy estimation of stool output using the single bag. For example, as stool is collected within the fecal material collection chamber of the collection bag, it may displace the source of irrigation. This is illustrated in FIGS. 20A-20D in the case of just water transfer between two chambers that share a compliant barrier between them. This may occur, for example, when the irrigation fluid is applied into the rectum, but no stool is present. In FIG. 20A, the collection bag 2000 includes a first side 2071 (e.g., front side, left side, etc.) holding the irrigation fluid (in this example, water) and a second, adjacent, side 2073 configured to hold fecal material. The outside of the chamber (bag) may be rigid or fixed in shape or flexible, while the dividing membrane 2091 between the first and second chambers may be compliant.

Figures 21A, 21B, 21C:
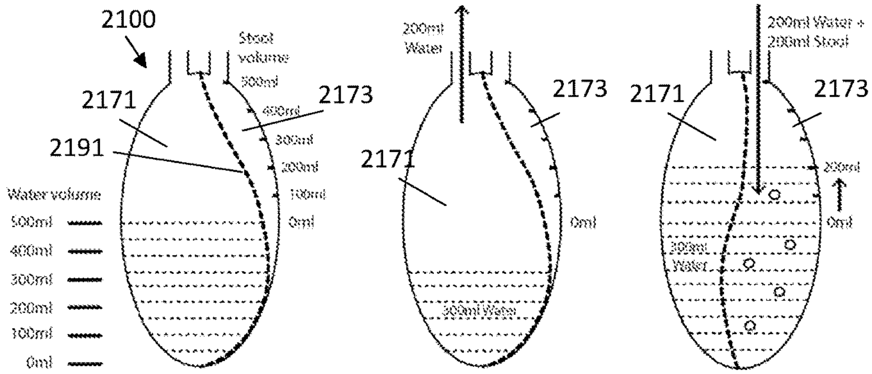
FIGS. 21A-21C illustrate the operation of another example of a collection chamber as described herein.

In the initial state (FIG. 20A) the first side holding a fixed amount of irrigation fluid, show by the dashed line (e.g., 500 ml) and the fecal material receiving container 2073 is empty, so overall volume in the bag is 500 ml. As fluid is transferred 2024 by the apparatus to irrigate the rectum, it is pumped out of the irrigation container 2071. For example, if 300 ml water is used for irrigation, it is pumped out of the irrigation container to irrigate the rectum. Suction is then applied, and material (including the 300 ml of irrigation water) will get pumped from the rectum, via the receptacle, and then collected in the fecal matter compartment 2073 of the bag. In this case, where it is assumed that there is no stool in the rectum, only the irrigation solution (e.g., water) will return to the stool compartment. When this happens, the middle layer separating the water and stool compartment will move left, but the overall level in the bag will remain same, i.e. 500 ml, as shown in FIG. 20B. FIGS. 20C and 20D demonstrate the same result; further irrigation from the irrigation container 2071 pumped into the rectum results in only irrigation fluid returning by suction through the receptacle and connecting tubing into the stool compartment 2073; the overall height of the content in the bag will remain the same. Thus the first side and the second sides may change the amount being held, but the fill line 2023 does not change. Any difference in the height of the bag following irrigation and suction will therefore represent the volume added (e.g., by removing fecal matter). Thus, these collection bags may be used to approximate the volume of fecal material collected, as illustrated in FIGS. 21A-21C. The bag may be marked with approximate calibration levels, as shown. In some examples the fill level of the irrigation side, with the fecal material collection side empty, may be set to the baseline level. Initially, as shown in FIG. 21A, the irrigation fluid containing side of the bag 2071 contains 500 mL of irrigation fluid (water) and the fecal material collection sides 2073 does not include any material. A compliant membrane 2191 separates the two sides; the outer walls of the collection chamber 2100 are rigid or fixed in shape or flexible. In FIG. 21B 200 mL of water is used to irrigate the rectum, e.g., by using the irrigation pump apply the irrigation fluid into the rectum through a receptacle that has been placed into the rectum. Thereafter, suction may be applied from the receptacle through the suction channel and fecal material (including the original 200 mL of irrigation fluid) may be sucked and removed from the rectum, into the suction lumen of the receptacle and then into the collection chamber 2100 as shown in FIG. 21C. The resulting volume returned is 400 ml, including the initial 200 ml of irrigation fluid and an additional 200 mL of fecal material that is returned to the fecal material collection side 2173; the difference in level between the initial volume of irrigation solution and the final volume after suction is 200 mL, which is the approximate volume of stool removed.

Thus the external collection chambers (e.g., bags) may be dual bags (dual external collection chambers) and may be calibrated. Thus, any of the external collection chambers (collection bags) described herein may include one or more (e.g., may consists of two mutually separate) compartments. This disposable bag may be discarded either when the collection compartment of the bag is full. In variations including dual external collection chambers, the disposable bag may be discarded when the irrigation compartment of the bag is empty.

Figure 22:
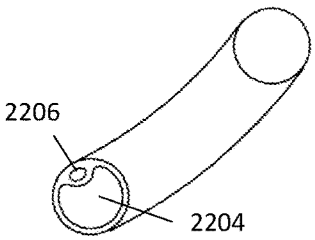
FIG. 22 shows one example of an interface tube (connecting tube) that may be used, e.g., between a receptacle and the housing of an apparatus as described herein.
Figure 23:
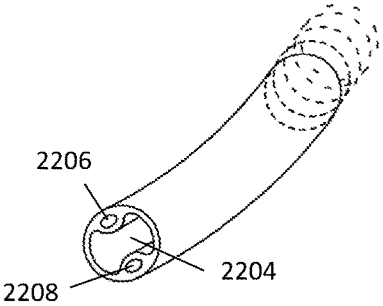
FIG. 23 shows an example of an interface tube (connecting tube) that may be used, e.g., between a receptacle and the housing of an apparatus as described herein.

FIGS. 22 and 23 illustrate examples of interface tubes (collecting tube) that may be used between the cannister (e.g., housing) and the receptacle. In FIG. 22, the connecting tube includes a central suction lumen 2204 and an additional irrigation lumen 2206. The tubing may be flexible but sufficiently stiff or rigid to as to prevent collapse under the suction applied through the central suction lumen. FIG. 23 shows another example of a connecting tube include three lumen: a central suction lumen 2304, an irrigation lumen 2306, and a second (e.g., air) lumen 2308. The connecting tubing may be flexible and/or may include one or more joint (bending) regions. As mentioned, the connecting tubing may be integrally connected or formed with the receptacle. The connectors connecting the tubing to other portions of the apparatus may be secured to prevent leaking.

Figure 24:
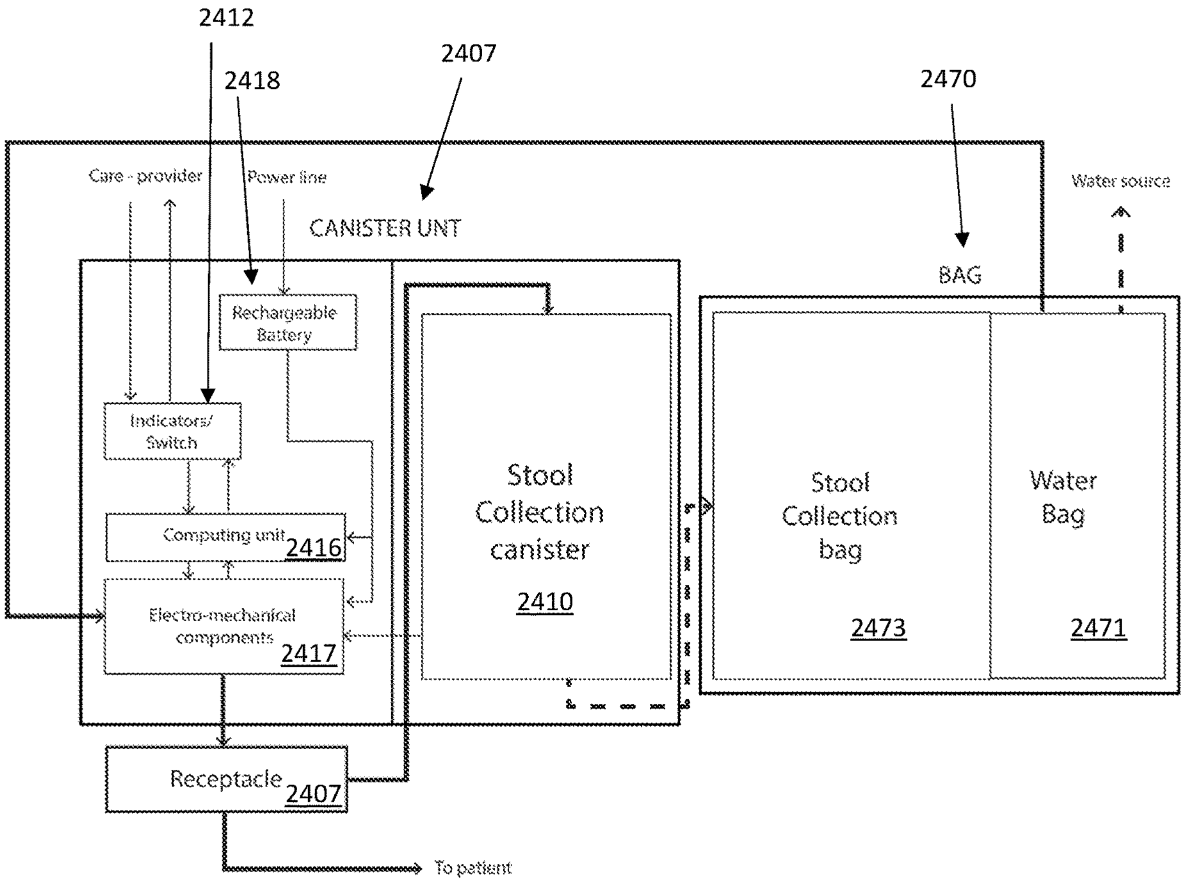
FIG. 24 schematically illustrates one example of an apparatus as described herein.
Figure 25:
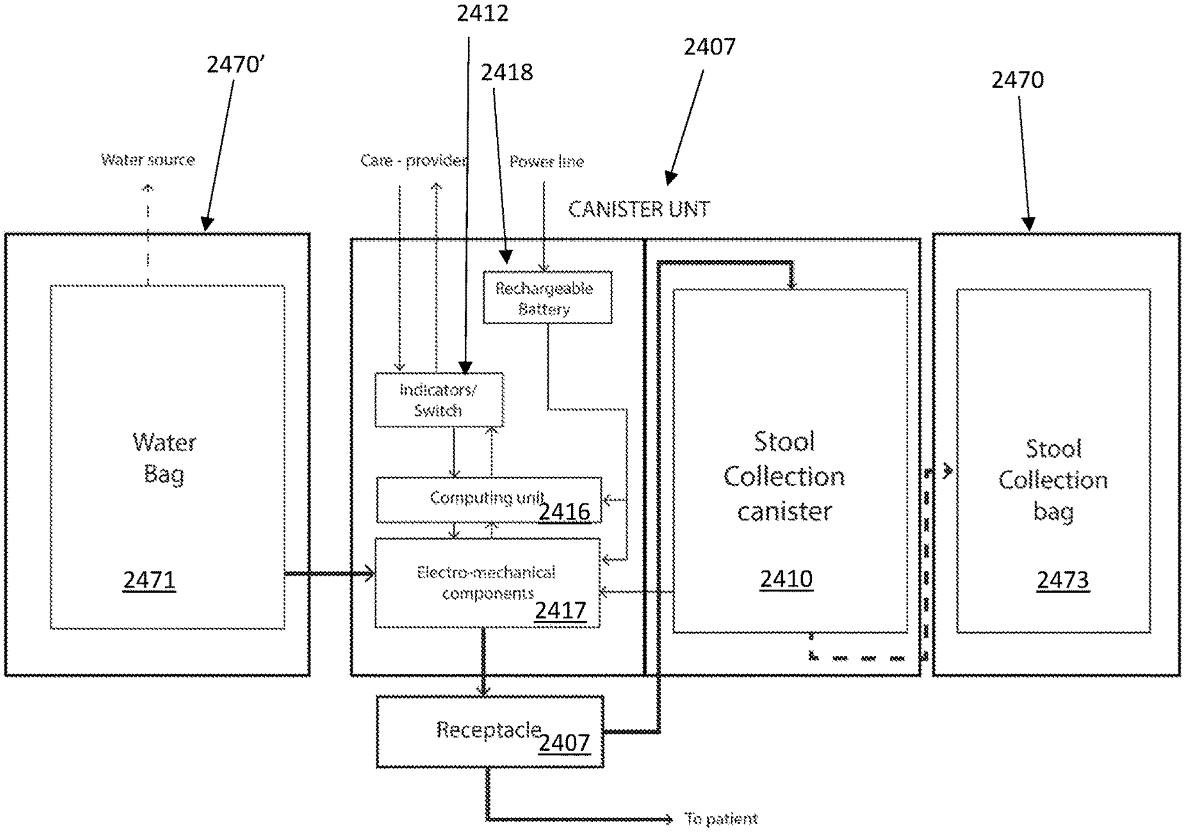
FIG. 25 schematically illustrates an example of an apparatus as described herein.
Figure 26:
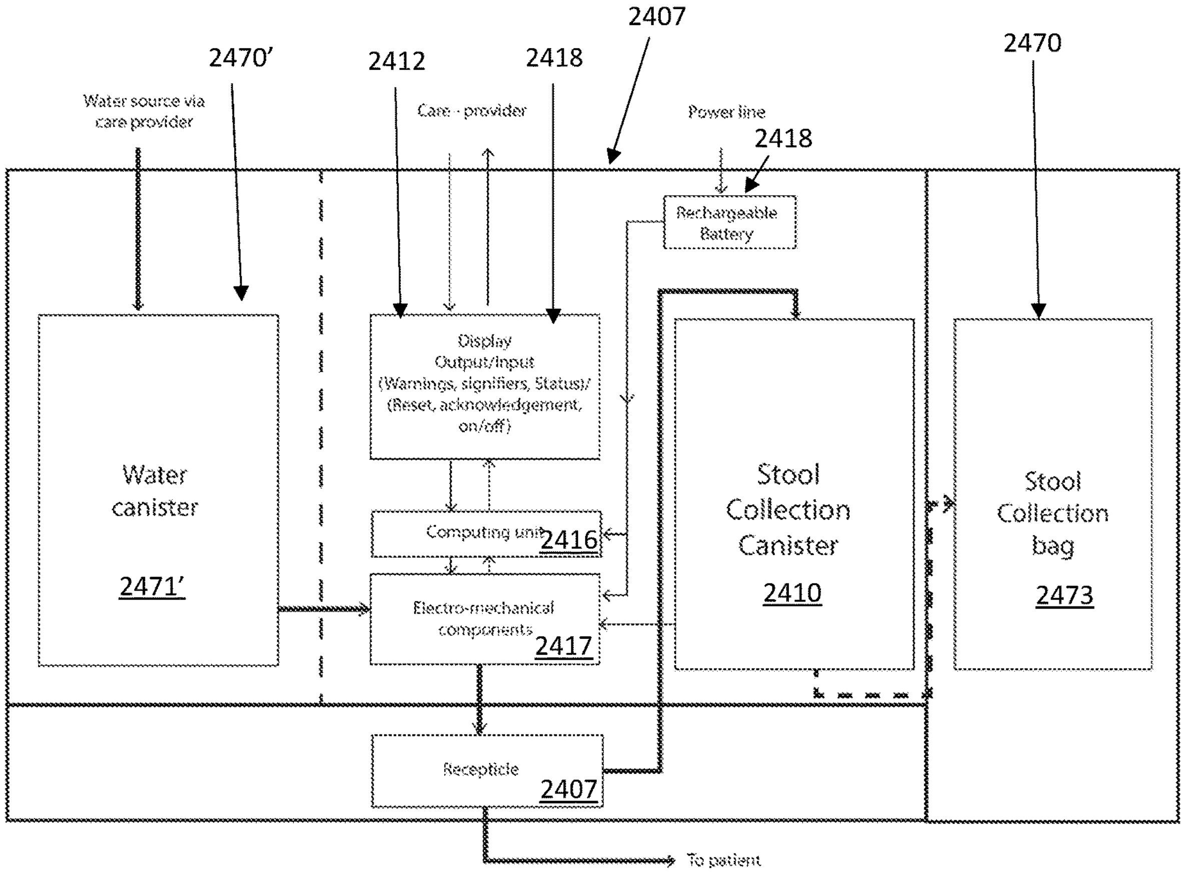
FIG. 26 schematically illustrates an example of an apparatus as described herein.

FIGS. 24-26 show schematic diagrams of examples of apparatuses as described herein. In FIG. 24 the apparatus (e.g., system for collecting fecal matter from a patient) may include a cannister 2407 ("cannister unit" or housing) that includes the internal stool collection canister 2410 that may have rigid sides, so as not to collapse when drawing suction through the receptacle 2403. The cannister also at least partially includes the controller 2616 ("computing unit") and inputs 2412, the battery and/or power circuits 2418, and other electronics or control circuitry (such as, but not limited to) other electromechanical components 2417 (such as pumps, valves, etc.). As shown in FIGS. 13 to 16B, the apparatus may continue to operate, drawing irrigation fluid from the water bag 2471, pumping it into the rectum, then applying suction to withdraw material from the rectum through the receptacle 2407 and into a rigid walled container such as the stool collection cannister 2410 or in some variations directly into an external collection chamber 2470 ("bag"), and more specifically into a stool collection bag 2473 within the external collection chamber.

Thus, in FIG. 24 the cannister unit couples to a dual bag including both the stool collection chamber 2473 and an irrigation supply or source 2471. FIG. 25 schematically illustrates an example of an apparatus as described herein including the same canister unit as in FIG. 24, but with separate irrigation fluid bags (2471) stool collection bags 2473. Similarly, FIG. 26 schematically illustrates an apparatus in which the irrigation fluid is integrated and held in a container 2471' within the cannister 2407. The cannister also includes the stool collection canister 2410 (which may act as an intermediate holding area for the collected fecal matter). The cannister may also house the controller 2416 and electromechanical components 2417 (e.g., pumps, valves, etc.) as well as inputs and outputs, such as display input/outputs and controls 2412.

Operation

The apparatuses described herein are generally vacuum-based apparatuses that can be placed on either side of, or within the anal opening, and/or on either side of a stoma, to effectively manage fecal waste collection, before, during or after the defecation process. Each of the examples and related apparatuses disclosed herein may be use for treating or managing incontinence, impaction, constipation, colonic irrigation, pain management, stoma management, anastomosis site management and reconstructive surgeries. In a healthy state, fecal material is discharged from the colon into the rectum, which is further expelled from the body by a wave like muscular contraction of the colon and rectal walls (peristalsis) and a corresponding relaxation of the puborectalis muscle and sphincter. Peristaltic contractions cause the rectal walls to expand and contract to move fecal matter towards the anal opening.

The methods and apparatuses described herein may include a receptacle for coupling to the patient to receive fecal matter and to apply irrigation that is connected to a vacuum source, such that a pre- or self-calibrated vacuum pressure is created over a pre- or self-determined period of time, to collect fecal material, before, during or after the defecation process, without completely harming the colorectal anatomy, dehydrating the anorectal apparatus, or causing any injury, trauma or foreign body sensation to the patient.

These apparatuses may account for the nerves and physiology of the rectum and anal canal. The anorectal junction (the boundary between rectum and anal canal) provides a limiting boundary for particular nerve types. Visceral nerves are found above the anorectal junction, while somatic nerves are found below the said junction. Somatic nerves are capable of sensing pain, while visceral nerves only sense pressure and not pain. Because of the presence of somatic nerves, the portion between anorectal junction and anal verge is extremely sensitive and can cause a high level of discomfort in case of pressure, vacuum, or other similar forces are applied or large bore/rigid objects that may be placed within the anal canal or at the anorectal junction.

The vacuum that is applied to the receptacle may be applied at a specific location, such that vacuum conduit is flush at the lowest point of the receptacle, and the vacuum forces are diffused and directed in a manner, such that there is no pain, discomfort or injury at the ano-rectal apparatus. The vacuum source may be configured to be in-line and programmed to a pre-determined force and frequency. The vacuum may be generated by means of a vacuum pump and transferred to the receptacle via a transit conduit (e.g., connecting tube). Those skilled in the art would appreciate that the vacuum pressure, size of the tube, length of the tube, shape of the tube, placement of unidirectional valve, pressure release valves and vacuum locks, may be controlled as described herein and the application of irrigation and suction may be coordinated, e.g., by the controller, to optimize collection and operation (e.g., power usage, conservation of irrigation material, etc.) of the apparatus.

In general, the methods and apparatuses described herein may use a vacuum pump that is connected to a receptacle that may generates vacuum in the range of 0-500 mm Hg. The vacuum pump may be programmable via either mechanical, electromechanical or solid state relays. For example, the controller may control the operation of the vacuum pump either directly or indirectly (including using a vacuum modulator to adjust the applied pressure). The vacuum pump may be powered by a battery/cell or connect to a power source. The vacuum pump and/or controller may be connected to one or more sensors that may be positioned on the receptacle or along the transit conduit (connecting tube) to regulate the vacuum pressure in the system and to facilitate on, off and reset of the pump. The vacuum pump may be insulated or muffled to neutralize its operating sound to ensure the ambient noise of the care environment is not impacted.

In some examples the vacuum pump may be connected to a flatus release mechanism involving a charcoal filter and layers of fluoropolymers to facilitate the release of flatulence or other odorous, or non-odorous gases from the system, without creating a leakage or a vacuum lock in the system. In some examples a portable, lightweight vacuum pump may be used as the vacuum source. In some examples the vacuum source can be a central source of the healthcare facility; the apparatus may instead use a vacuum modulator to adjust the applied suction (on/off, level of suction, etc.) by controlling valves, a manifold, etc. In some examples the vacuum source can be an external vacuum source involving one or all of, a cylinder, plunger, piston, bellow, squeeze ball or other venturi devices. These embodiments have the same features similar to an in-line pump disclosed above.

In addition to the vacuum (negative pressure) source the methods and apparatuses described herein may also use one or more sources of irrigation solution (e.g., water). The use of fluid, in conjunction with vacuum, may also enable the collection of fecal material of varied Bristol Scale. As the patient overall clinical condition improves, their stool typically hardens. However, most indwelling fecal management devices, are rendered useless, once the stool changes from a Bristol scale 7 to a Bristol scale 5 or more firm. The apparatuses described herein may operate with fecal material from Bristol scale 7 to Bristol scale 2.

For example, the flow of irrigation fluid may be configured to flow in a pre-determined pattern, location and pressure inside the anatomy (e.g., within the rectum) upon delivery from the receptacle or an associated irrigation port, and irrigation may be configured to assists in removal of residual fecal material that may be within the device (e.g., the receptacle, connecting tube, stool collection cannister, etc. The irrigation solution may also reduce odor emanating from the fecal material collected.

Generally, as the stool moves towards the rectum, moisture is absorbed during peristalsis by the lower GI anatomy, resulting in the formation of feces. While this natural process does not dehydrate the anatomy, one or a combination of comorbidities, therapeutic dosages and changes in the intra-rectal pressures caused by external triggers, including the application of (as here) negative pressure, could dehydrate the anatomy and impact patient pathophysiology. Thus, coordinating the application of suction with irrigation may be surprisingly helpful.

The controller may apply suction and/or irrigation and/or air in a variety of patterns. In some case the apparatus may apply irrigation for an irrigation duration and/or volume, followed immediately by suction for a suction duration and/or intensity. In general, the irrigation duration may be less than the suction duration. For example, the suction may be applied for between 1.5 to 200 fold longer (or more) than the irrigation (e.g., suction may be applied for greater than 2 fold, 3 fold, 4 fold, 5 fold, 6 fold, 7 fold, 8 fold, 9 fold, 10 fold, 11 fold, 12 fold, 13 fold, 14 fold, 15 fold, 50 fold, 100 fold, 150 fold, 200 fold, etc. or longer). Alternatively in some examples the apparatus may include an enema mode in which an excess of irrigation solution is applied (e.g., greater than 300 ml, 250 ml or more, 300 ml or more, 350 ml or more, 400 ml or more, 450 ml or more, 500 ml or more, etc.). When the apparatus is operating in the enema mode, the irrigation cycle may be longer than vacuum cycle and the irrigation pump flow rate may be much smaller (~100 ml/min) when compared to vacuum pump (~4 L/min). The larger amount of irrigation fluid injected in the patient rectum in enema mode to flush the rectum may require longer to add fluid then to remove it.

In general, the apparatus may inject the fluid (irrigation fluid) to irrigate the bowel at any appropriate rate. The controller may set the irrigation rate by controlling the operation of the fluid pump and/or valves. The apparatus may include one or more flow or pressure sensors within the housing (e.g., monitoring the fluid pump, within the connecting tubing, etc.). The controller may measure the load on the pump(s). For example, the fluid pump may inject fluid (irrigation fluid) at a rate of between about 5 ml/min and 500 ml/min, etc.). The apparatus may adjust the irrigation rate during the application (to apply pulsatile irrigation). In some examples the apparatus may apply at a different rate or with a different rate profile based on the user-selected mode or the automatically-selected mode (e.g., enema mode, irrigation mode, etc.).

Either the irrigation and/or the suction may be applied continuously or in a pulsatile manner. In some examples, the application of irrigation may be pulsatile while the suction is continuous. In some examples the application of irrigation may be continuous while the suction is applied in a pulsatile manner. In some examples both irrigation and suction are applied in a pulsatile manner. In some examples, irrigation may be applied to deliver between 2 and 300 mls of irrigation solution (e.g., water), or more (e.g., during enema mode, as described in further detail below). For example, each round of irrigation may apply between 2 and 200 mls of irrigation solution (e.g., between 1 and 175 mls, between 5 and 200 mls, between 5-175 mls, between 2-150 mls, between 5-150 mls, between 10 and 250 mls, between 10-200 mls, between 10-150 mls, between 2-125 mls, between 5-125 mls, between 10-125 mls, between 2-100 mls, between 5-100 mls, between 10-100 mls, between 2-75 mls, between 5-75 mls, between 10-75 mls, between 2-50 mls, between 5-50 mls, between 10-50 mls, etc.). For example, irrigation fluid may be delivered in a quantum of 1-100 ml per sequence. During enema mode, the apparatus may deliver between 200 ml and 1 L (e.g., between 200 mL and 800 mL, between 200 mL and 600 mL, etc.). The volume of fluid applied may be based on a patient characteristic (e.g., patient weight, age, gender, etc.). The controller may adject the volume and may alter the volume (increasing or decreasing) for different cycles.

In some examples vacuum may be applied concurrently or overlapping with irrigation.

In some examples air may be applied instead or in addition to irrigation fluid to create positive pressure in the rectum. For example, a brief pulse of air may be applied (e.g., for between 0.5 seconds to 10 seconds, between 1 second to 8 seconds, etc.), followed by suction; suction may be applied longer than the air is applied.

In any of these apparatuses and methods air may be applied into the rectum, before or after the application of suction. For example air may be applied to assist in removing waste material and/or it may be applied to equalize the pressure within the rectum and/or air may be applied if the negative pressure within the rectum (as detected by one or more sensors) exceed a threshold, to prevent damage or pain.

In general, the apparatuses described herein may measure either or both negative and positive pressure. For example, negative and positive pressure may be detected using an air pressure sensor which is incorporated into the apparatus electronics. Negative pressure may be measure, for example, in the collection canister. In some examples positive pressure may be measured in the rectum. Suction may be applied directly to the collection canister (e.g., to the internal collection chamber within the cannister housing) and negative pressure may be highest in the canister. Pressure (typically positive pressure) may be measured within the rectum using one or more sensors in/on the receptacle. As mentioned, an any of these apparatus air may be pumped directly in the rectum, and thus positive pressure may be highest in the rectum even though both rectum and collection canister are connected with the transit tube.

The apparatuses descried herein may include a fluid (irrigation fluid) reservoir and pump (or in some examples the irrigation fluid may be driven by gravity from the bag, chamber, etc.) that may be in-line and connected to a receptacle via a transit conduit. The receptacle may have one or more outlets for fluid, that may be placed between the orifice where suction is applied and the periphery of the receptacle, more towards the periphery of the receptacle, and that may be spaced at least 1 mm from each other to create a fluid flow for irrigation such that this flow both irrigates the rectum and flows the material towards the orifice where suction is applied. For example, fluid outlets can be in a single circumferential row, in multiple rows, in a zig-zag pattern, and can be of same of different diameters, or some outlets are at a different angle to project fluid at different trajectories, or may be either flush, or slightly protruding to both irrigate and flow the output in a specific direction. The reservoir may be configured to hold up to 2 liters of fluid and can be refilled as needed. In one example the reservoir is designed to be towards the base of the device to provide additional stability but can be anywhere along the length of the device.

The reservoir may be connected to a fluid pump via a kink resistant conduit. The pump may be capable of delivering fluids from reservoir to the receptacle, in specific volumes and in forms of a stream, jet, spray, rotational or mist in continuous or pulsating form. The pump can be powered either using a battery or wall power source and may be configured for the length of product use. The pump may be programmable by either a mechanical, electromechanical or solid state relay (e.g., software, hardware of firmware). The pump may be programmed to function in tandem with a vacuum source to hydrate the anatomy, break the fecal material, assist in collecting and suctioning of fecal material, ensuring the lumen remains patent, push back on any tissue that may be suctioned towards the receptacle, and helping in control of odor. Irrigation may be used to deliver therapeutic agents as well along with the fluid.

The irrigation solution may be applied by use of a pump or by other mechanisms. For example, manual infusion may be performed using syringes, inflation devices, a squeeze bag, siphon method, gravity bag, or vacuum linked.

As mentioned above, irrigation (e.g., hydration) and suction may be performed sequentially and separately, either in tandem, or separated by a delay period (e.g., 0.1 second, 0.5 seconds, 1 second, 1.5 seconds, 2 seconds, 3 seconds, 4 seconds, 5 seconds, 6 seconds, 7 seconds, 8 seconds, 9 seconds, 10 seconds, 12 seconds, 15 seconds, 20 seconds, 30 seconds, etc., or more). The vacuum suction, size of the suction tube and travel length may be adjusted to improve suction of fecal material and may rely on secondary mechanisms to hydrate the anatomy. Although the examples described herein include hydration by irrigation of fluid in the rectum, hydration can be achieved with delivery of fluids by way of intra venous transfusion, or transdermal delivery, or orally, or via intraosseous route.

The anal canal is about 25-50 millimeters in length and is supported by internal and external sphincter muscles. For a healthy individual, internal diameter of anal canal in resting state is close to zero, but it can distend to about 30 millimeters in diameter to facilitate the outward purge of fecal material and flatulence. The anal canal is surrounded by internal and external sphincter muscles and works in close conjunction with puborectalis muscle, which aligns the rectum to a 90 degree position during fecal evacuation. The contraction of the puborectalis is initiated with changes in intrarectal pressure and a secondary signal to the sphincter muscles and corresponding somatic nerves.

The transit conduit (also referred to herein as connecting tube) typically starts at the anal opening, rests between the legs of the patient and on the proximal end is connected to a vacuum and fluid source and may be a conduit that houses independent channels to deliver fluid and vacuum pressure. The conduit may be configured to remain patent (e.g., not collapse) under vacuum, thereby preventing any vacuum lock in the system, and should not manifest any injury to the lower extremities by way of scrapping, rough edges, hard features or excessive moisture wicking properties.

The methods and apparatuses described herein may use a tube and sheath (e.g., connecting tube), that may be co-extruded to provide independent conduits for both fluids and vacuum as shown in FIGS. 22 and 23. The transit sheath may use a webbed, braided or tube of a preferred durometer to maintain lumen patency at all times and prevent vacuum lock. Kinking, bending of tubes during patient care is an unavoidable occurrence. The tube/sheath material may be selected with a specific flexural modulus such that it enables extrusion of the sheath, both with or without an intermediary surface like a braid or web, and helps in springing back the conduit when collapsed, kinked or bent.

Vacuum lock of the receptacle within the rectum can also be averted by connecting a pressure balancing mechanism that is in-line or not in-line with the transit conduit. The pressure balancing mechanism can have a one-way mechanism to prevent the outward flow of fluid but allow inward flow of air/gas. The vacuum lock can also be prevented by placing a lattice like structure in the transit conduit that is either continuous or intermittent. The transit conduit can have a suction channel for transporting stool. Any of the tubing or connectors described herein may include valves, including unidirectional flow valves like flutter valve, leaf valve, duck-bill valve, etc. to facilitate the movement of material only during suction.

In some examples the transit conduit (connection tubing) is made of either silicon, TPE or a blend of polymers, lined or not lined with oxygen barrier polymers like PVDC or EVOH, in a manner where the conduit is either opaque, translucent or transparent for the most part. A small aperture may be provided to visualize the output for monitoring and recording of color, consistency, output, etc. The conduit may be configured to rest between the legs of the patient and can be connected to the vacuum source towards the end of the bed. The conduit may be configured to be odor containing by use of layered polymers like EVOH and PVDC.

Any of these apparatuses may also include an interface that will act as the main hub of activities for the nurses. The interface has dedicated port where the transit conduit attaches to a vacuum source, fluid pump (irrigation source), air source, a power/battery source, and electronics that support either solid state or electromechanical relays, are housed together. The interface is designed to have external on/off switch, visual display and other connection paraphernalia. The interface may have a dedicated port where the transit conduit attaches to a vacuum Source via connection mechanisms like snap fit, interference fit, friction fit, screwed, clipped on, or by way of various temporary adhesion and securing mechanism. The connection to the vacuum source may be external to the interface but may be coupled to the vacuum source via an intermediary conduit. This assembly may be configured to provide an efficient environment for care and provide a leak proof assembly.

In the event, the negative pressure in the transit conduit or the vacuum source exceeds a pre-determined threshold, the pump may be programmed to shut off temporarily and or reset to the programmed parameters (e.g., by operation of the controller, which may monitor the sensor(s)). A detection mechanism may be placed at the interface module and can comprise of a pressure sensor, space sensor, or a similar mechanism related to visual, sound, pressure, force, distance or flow. An interface may have a dedicated port where the transit conduit attaches to a fluid pump (irrigation pump) via a connection mechanism such as one or more Leur locks, 3 way stop cocks, O-ring compression, ball-bearing spring, snap fit, interference fit, friction fit, screwed, clipped on, or by way of various temporary adhesion and securing mechanism. A connection to the fluid pump can be external to the interface but can further be connected to the fluid pump via an intermediary conduit. Such an assembly must be easy to connect, disconnect and be completely leak proof.

An elongated, flexible conduit, that is kink and puncture resistant, and that is further connected to a fluid reservoir may be included, e.g., on the proximal side of the pump. The reservoir may be a part of the interface in a rigid or semi-rigid structure (e.g., housing, bag, etc.), and in some examples the reservoir is part of the disposable bag. The flexible conduit may deliver the fluid from the reservoir to the receptacle by aid of the fluid pump and via the transit sheath.

The proximal side of the vacuum source may be connected to a fecal material intermediary hold chamber (also referred to herein as a "stool collection canister" as described above) and may include another outlet for release of air/flatus. The hold chamber may be a rigid or semi-rigid chamber that in configured to collect the flow of material from the vacuum line and flow towards the central portion of this chamber. In addition to the shape of the chamber, the surface of the chamber may be made lubricious, by way of material selection and surface modifications like silicon lubricants, oil, etc., to facilitate the flow of viscous material. A part of the intermediary hold chamber may be configured to taper into an opening that further connects to a one-way flow valve and a disposable bag. The intermediary hold chamber may be configured to create and maintain a certain internal pressure that when synchronized with the operation of vacuum pump creates a certain differential pressure that enables the flow of material in a specific direction towards the distal part and prevents the hold chamber from collapsing or creating a vacuum lock. In some examples the intermediary hold chamber also has a float valve, that is designed to signal when the chamber is full. In another embodiment, a hydrophobic cut-off valve is used. The valves are connected to vacuum pump and fluid pump, such that the suction and irrigation system shuts off when excessive material is accumulated in the hold chamber.

The housing or cannister (which may be referred to herein as an interface) can be configured as a rigid, semi-rigid, flexible, disposable, opaque and transparent structure. The housing may be designed to have external on/off switch, visual display and other connection paraphernalia to further connect the two pumps to a reservoir for fluid and a multi-chamber construct, with differential pressure, to house a bag or a container for collection and disposal of fecal material.

At the manifold of vacuum pump within the housing, a compact filter for management of flatulence and malodor may be included. The apparatus described herein may include the use of carbon, charcoal, and other filters, in conjunction with other soft or hard semi-crystalline structures to neutralize malodor before releasing to the environment. The inner walls of the housing may be insulated to contain the sound/noise from the two pumps to make the environment more relaxing and conducive for patient recovery.

The vacuum pump, fluid pump, power source, power switch, control valves and display units may be connected using electrical circuitry. In some examples one or more sensor, that may contact the user's anatomy, may also be connected to the electrical circuit. This circuit may be insulated from moisture and housed inside the interface. Any of these apparatuses may include one or more mechanical, electromechanical and solid state relays to operate the pumps at pre- or self-determined frequency and per the synchronized parameters. Solid state relays may be used to operate the various components of the system. For example, a solid-state relay may be used to program a unique sequence of functions, that works complimentary to the patients' GI motility and physiology, to facilitate the transfer of fecal material from the rectum to an external collection source. In some examples the parameters for operating the apparatus can be customized and auto-programmed based on physiological, motility and other anatomical changes in real time. For example, programming may be done when hard wired using a programmable circuit board; in some examples the programing can be done remotely using either a Bluetooth or WiFi or other similar wireless technologies. The user (doctor, nurse, technician, caregiver) may adjust the operation (e.g., programming) of the apparatus during use.

The electronics may be configured to function at different supply voltages, which may occur across various geographies. The apparatus may include a central on-off switch for the entire system to simplify the operations from a care providers perspective, and also an external display mechanism to inform the user when a specific function like irrigation, vacuum, vacuum pressure about to breach threshold, and presence of vacuum lock is present (e.g., LED display, etc.)

The apparatus may be pre-calibrated or may be user calibrated. In general, the apparatus may limit the pressures applied through the receptacle. To prevent harm to GI motility, anorectal anatomy including the material properties of rectum, any exposed mucosa, internal hemorrhoids, polyps, fissures, and other pathologies, initial vacuum suction and positive air pressure may be limited to the range of 10-500 mm Hg. An initial high suction level may be followed by another burst of the same, higher or lower vacuum force. The system is configured to deliver fluids and vacuum that is reasonably precise and accurate.

In some examples, the apparatus may be configured to deliver a pattern of suction and irrigation that follows the sequence of flush-suction-flush-suction or suction-flush-suction or flush-suction-air-flush-suction-air or suction-flush-air-suction-flush-air. Other patterns or combinations may be used. Following delivery of the pattern, the apparatus may determine the status of the system (e.g., pressure, flow or volume) to determine if stool removed, and if additional suction and/or flushing should be applied or if the system should return to a standby state. Within the flush/suction or suction/flush suction pattern, the applied suction and/or applied flushing may be constant or may be varying. Varying the applied suction and/or irrigation ("flushing") may include applying pulsatile suction (rapidly transitioning between low and high flow), or increasing and/or decreasing gradually (e.g., ramping up/down).

For example sequences that may be applied include flush-suction-flush or suction-flush-suction-flush or in similar other combinations; the last flush may aid in both hydrating the anatomy as well as pushing back on any tissue that may be pulled towards the receptacle. Alternatively, in some cases the apparatus may instead apply suction last, or in some examples a lower level of suction.

In some examples, the amount of irrigation fluid applied during flushing may be between about 1 to 500 ml of fluid. The irrigation fluid may be saline, distilled water, tap water, or any of these, including mixtures with a therapeutic or wellness substance, which may be discharged at every irrigation for the total duration of device use.

In some examples between 10-500 mm Hg of vacuum pressure is applied for up to 30 minutes for each vacuum cycle. In the event, a vacuum lock is detected, or vacuum pressure breaches its upper defined threshold, the vacuum source may be reset, and the sequence started afresh after waiting for certain time, or immediately, with a fluid irrigation or air flush. The vacuum source may also reset automatically, and restart the programmed sequenced, if the intermediary hold chamber is full, after allowing time to clear (empty) the intermediary hold chamber into the collection bag. In any of these apparatuses, the applied vacuum may be interrupted periodically by a flush with air that may effectively bring vacuum pressure to zero. The cycle of suction and air flush (or in some cases application of positive pressure of air or $CO_2$) may be repeated in order to help remove material as described above. In some cases irrigation fluid may also be applied as part of the cycle. The period of the cycle may be regulated by the apparatus based on time and/or by pressure feedback from one or more sensors (including pressure sensors). For example, the apparatus may cycle the application of suction and air and/or irrigation fluid so that the cycle is repeated every few minutes (e.g., approximately every 1 minute, approximately every 2 minutes, approximately every 3 minutes, approximately every 4 minutes, approximately every 5 minutes, approximately every 6 minutes, approximately every 7 minutes, approximately every 8 minutes, approximately every 9 minutes, approximately every 10 minutes, etc.), as long as the operational parameters (pressure flow, etc.) remain within tolerance ranges to prevent discomfort, pain and harm to the patient.

The specific force range and duration may accommodate variation in stool consistency (e.g., Bristol 4-7) and notional loss of vacuum pressure between the source, receptacle, collection chamber and connectors in between.

The apparatuses described herein may also be configured to aid in management of gas, flatulence, odor, debris, lint, etc. is extremely critical. Any of these secretions could occlude the system and render it inoperable. A lot of research and innovation has gone behind understanding and describing the physiology of solid and liquid based material. However, gas or flatulence is largely ignored. The apparatuses described herein may include a flatulence releasing assembly that is connected to the suction outlet line in a manner, where the secretions are neutralized for odor and then expelled from the system.

For example these apparatuses may include a carbon filter, charcoal filter, or another odor absorbing/neutralizing substrate, that is either encapsulated, shielded or layered with non-porous structure. For example, the charcoal filter may be covered with a film of fluoropolymers, that has been optimized for barrier transmission, absorption of malodor and release of gases. The film may have multiple pores, of 0.1 or more microns, that are placed on this film, before being adhered to the filter. In some examples the charcoal filter is kept dry by creating a pocket from multiple films, that uses valves that are conducive to passing of gases but obstruct the flow of any fluid.

In general, any of the apparatuses described herein may be configured to apply suction, irrigation solution and air (or carbon dioxide) through the receptacle in order to remove fecal material. As described above, the receptacle may include a large suction channel inlet, and one or more irrigation channel outlets and/or air (gas) channel outlets. In any of these apparatuses the irrigation channel (fluid channel) outlet may also be configured to apply air. Alternatively or additionally a separate and dedicated air (gas) channel outlet may be included the connecting tubing may therefore include a separate or combined irrigation fluid and air (gas) channels.

In any of these apparatuses the controller may be configured to use the same pump for generating a suction and for generating positive air pressure. Alternatively a separate pump or source of positive air pressure, including external source of positive air pressure, may be used. In some cases, air may be delivered from into the rectum passively, by allowing air from outside of the apparatus to pass through the apparatus and into the rectum from the receptacle to prevent or release a vacuum (negative pressure) within the rectum. Alternatively or additionally air may be applied to actively increase the positive pressure, by pumping air (and/or $CO_2$) into the rectum.

The controller may be configured to apply positive pressure by injecting or otherwise delivering air or $CO_2$ into the rectum from the receptacle. In some cases the controller may be configured to apply a cycle of irrigation and/or positive pressure (air, $CO_2$, etc.) for a predetermined time period, and/or fluid volume and/or pressure, followed by the suction for a predetermined time period, and/or pressure. In some examples (e.g., for patients with more liquid stool), the apparatus may work without application of irrigation and instead may apply or allow air into the rectum through the receptacle (e.g., air inlet). The application of air through the receptacle as part of the fecal removal cycle may be particularly in patients with strong sphincter tone. In such patients, since there is no air escaping into the rectal vault, the apparatus may become locked so that noting moves from the rectum to the canister even at very high vacuum pressure. Allowing (passively) or pumping (actively) air into the rectum between periods of suction may therefore allow removal of fecal material without locking up the apparatus.

Figure 27A:
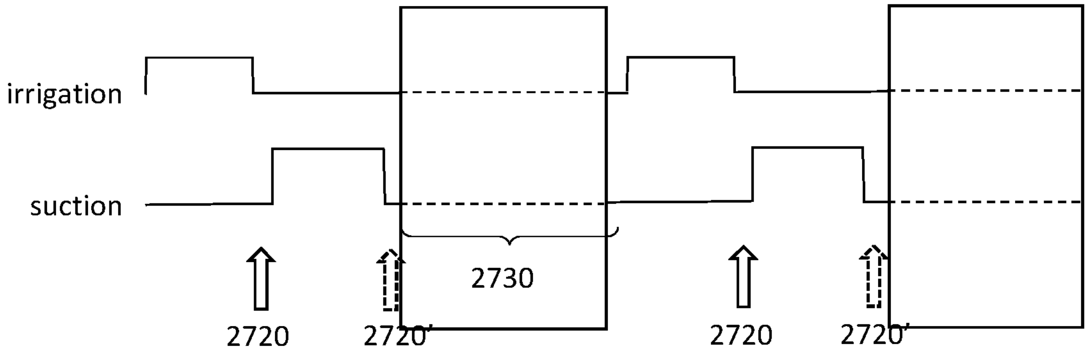
FIGS. 27A-27F show schematic examples of fecal removal cycles as described herein.

For example, FIGS. 27A-27F illustrate examples cycle profiles of suction/air/irrigation that may be used by any of these apparatuses, e.g. operating in a fecal removal mode. In FIG. 27A the controller may first apply irrigation (e.g., between 5-200 mL of irrigation) into the rectum, following by suction. In this example the suction is applied shortly or immediately after the irrigation fluid is applied; alternatively, the controller may wait a delay period (e.g., 1 second, 5 seconds, 30 seconds, 1 minute, 2 minutes, 3 minutes, 5 minutes, 10 minutes, etc.) before applying suction. In general, these apparatuses may be configured to establish a pressure deferential between the rectum and the collection container in order to drive collection of fecal material from the rectum. In FIG. 27A the controller may also be configured to allow or apply a release pressure 2720, 2720' either or both before and/or after the application of suction, as shown by the arrows. The release pressure may be provided by opening a channel through the receptacle (from the rectum) from the outside of the apparatus (e.g., through the connecting tube and capsule, including any filtration, odor filtration, etc. within the capsule), e.g., atmosphere. Alternatively, pressure may be positively applied by a pump. The controller may determine the duration and volume of irrigation solution added and the duration and rate of suction applied; the profiles shown in FIGS. 27A-27F are examples only, and do not represent actual duration or intensity of applied irrigation, suction and/or air. After the initially cycle, the cycle may be repeated, following a cycle interval (delay) 2730. The same cycle may be repeated, or a new cycle may be used (e.g., FIGS. 27B-27F).

Figure 27B:
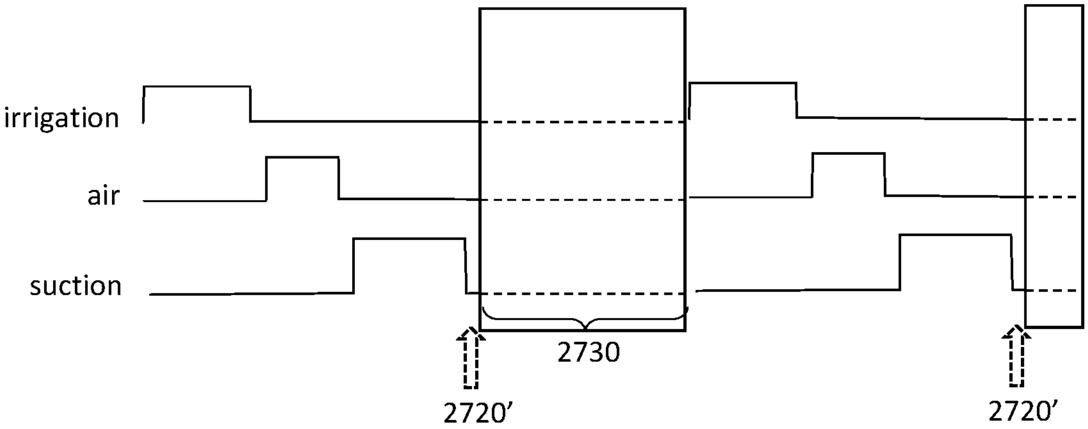

In some cases the apparatus may apply irritation and air (positive air pressure) through the air inlet in the receptacle. For example, FIG. 27B schematically illustrates one example of a profile for the application of irrigation, air and suction during each cycle. In FIG. 27B, the irrigation fluid may be applied at the start of the cycle, followed by the application of positive air pressure and then (immediately or after a delay), the application of suction. A release pressure may also be used after suction is applied 2720'.

Figure 27C:
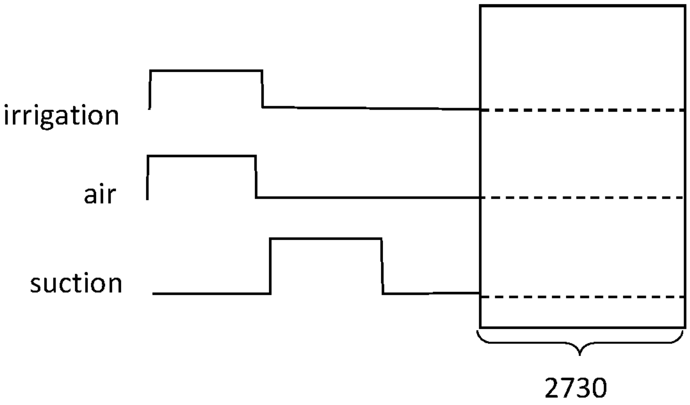

Alternatively or additionally, irrigation and air may be applied at the same time (or air may be applied before irrigation), as shown in FIG. 27C. In any of these examples, the duration that air is applied may be shorter or longer than the duration that irrigation is applied. A release pressure may be applied after the application of suction.

Figure 27D:
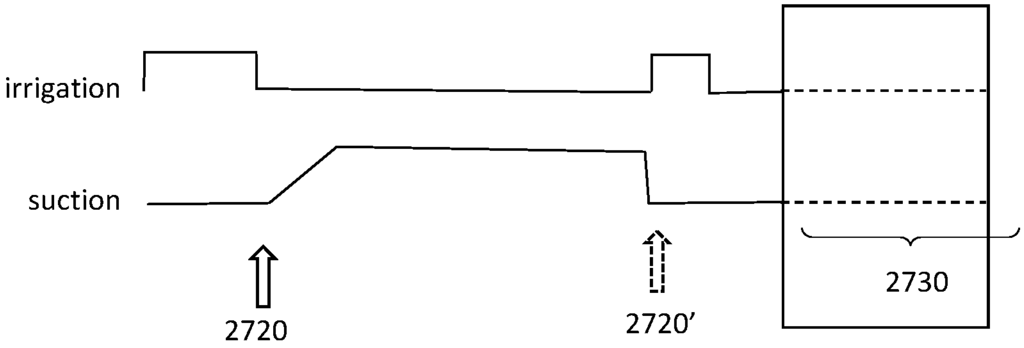

In some examples, not shown, the pressure may be applied with a varying pressure profile. For example the suction may be applied in a pulsatile fashion, in which suction is periodically released (as described above), including passively released. Irrigation may be applied at the start and/or end of the pulsatile pressure. In examples, pressure may be applied at a constant level and/or ramped up or down. For example, FIG. 27D illustrates an example of suction is applied in a ramp (e.g., ramping up) to a steady state. In FIG. 27D irrigation is applied both before and after the application of suction.

Figure 27E:
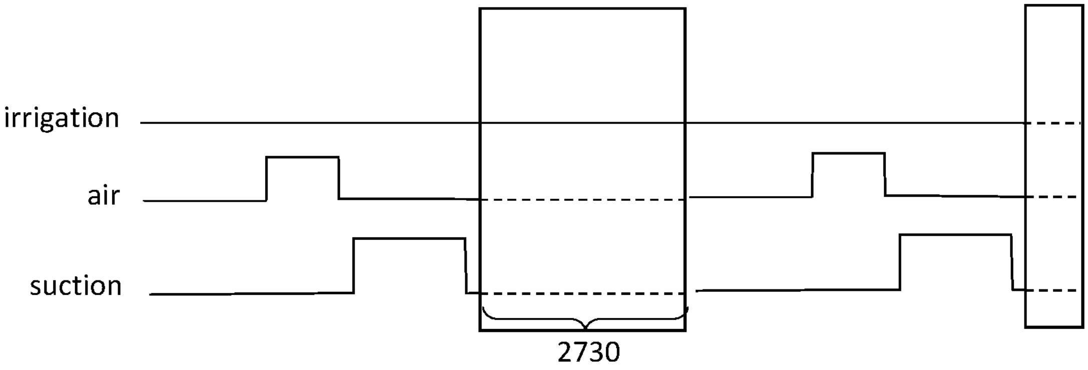

The apparatuses described herein may be used with just air and suction, without irrigation, as shown in FIG. 27E. In this example, positive pressure may be applied into the rectum followed by negative pressure (suction), as shown.

Figure 27F:
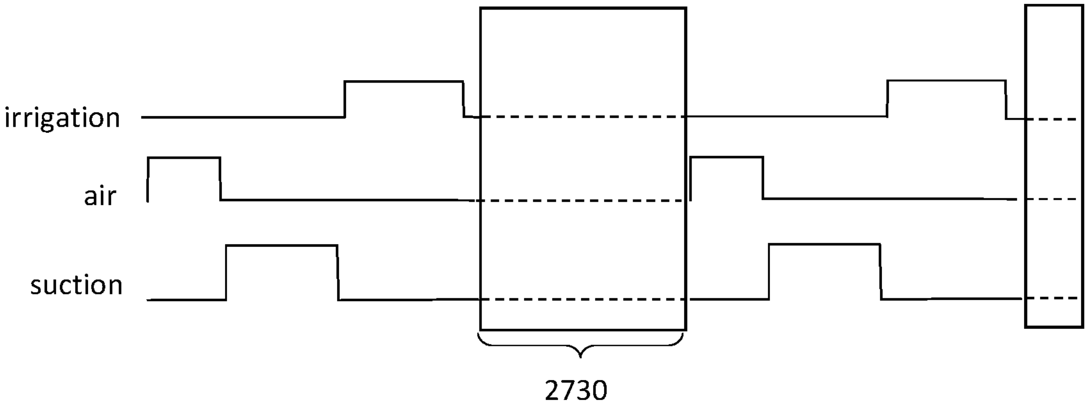

FIG. 27F illustrates another example, showing the application of air (positive pressure) into the rectum before suction is applied, finishing with irrigation. In the example shown in FIGS. 27A-27F the cycle includes just a single application of suction; in some examples, multiple periods of suction may be included in one cycle, as well as in some example, multiple periods of irrigation and/or multiple periods of air.

The apparatuses described herein may also be configured to operate in an enema mode, during which the apparatus may provide a relatively larger volume of irrigation solution (e.g., water, saline, etc.) followed by suction. In some cases the apparatus includes one or more controls on inputs to allow a user (e.g., nurse, caregiver, etc.) to trigger or schedule the application of the enema mode and/or to toggle the device between a fecal removal mode (e.g., using any of the cycles described above, and in FIGS. 27A-27F) and an enema mode. The apparatus may be configured to automatically operate in enema mode, based on a predefined schedule (e.g., once per 3 days, once per week, etc.) and/or based on one or more sensed inputs. For example the apparatus may detect the hardness and/or size of the stool. Harder, smaller stool may indicate enema mode is appropriate. When operating in enema mode, the apparatus may initially deliver a volume of between about 100 ml and 1 L (e.g., between about 200 ml and 900 ml, between about 200 ml and 600 ml, between about 500 ml and 900 ml, etc.). Generally, the volume of irrigation fluid used may be entered by the user and/or may be predetermined. In some examples the apparatus may select the volume of irrigation solution to apply based on the user-entered patent-specific information, such as patient weight, age, sex, condition, etc.

The present invention is also directed towards methods, systems and computer program products for controlling and/or operating the apparatuses that have been described hereinabove.

FIGS. 28 to 32 show flowcharts illustrating various methods for controlling and/or operating the apparatuses that have been described hereinabove.

FIG. 28 is a flowchart illustrating a first method according to the teachings of the present invention—wherein the method comprises method steps for controlling a fecal management apparatus (according to any of the embodiments described in connection with FIGS. 1 to 27F hereinabove) for eliminating buildup or accumulation of substantial amount of fecal matter in the rectum of a subject or user of said apparatus. The method of FIG. 28 achieves this objective by controlling the apparatus in a manner that enables periodic evacuation of bowel contents of the subject or user of said apparatus—thereby eliminating or reducing the likelihood of accumulation of substantial amount of fecal matter within the rectum. In various embodiments, the method of FIG. 28 may be implemented through one or more processors or controllers configured to control the apparatus(es) of the present invention based on the method steps of said method. In an exemplary embodiment, the method of FIG. 28 is implemented for controlling any of the apparatuses 100, 100', 100" that have been described in detail hereinabove. The method of FIG. 28 may be performed by implementing one or more of steps 2802 to 2806 as described in detail below.

Step 2802 comprises responding to detection of a first suction operation session initiation event, by implementing a first suction operation session. A first suction operation session initiation event may comprise any event that is predefined as a trigger event for initiating a first suction operation session—and may include any user input or any digital or analog signal, for example a user input provided through one or more buttons or through a user interface provided on or coupled with the apparatus 100, 100', 100". In response to detection of a first suction operation session initiation event, a first suction operation session is implemented.

Implementing the first suction operation session comprises initiating application of suction, for generating negative pressure at the receptacle (for example receptacle 200, 200', 200", 200'", 200"") of the apparatus 100, 100', 100". Suction may be applied at the receptacle through any mechanism for applying suction that is either internal to the apparatus 100, 100', 100" (for example suction pump 1312, suction pump 1512) or through any other vacuum or suction pump or any other source of suction that is external to the apparatus 100, 100', 100". The suction is applied upto detection of a first suction operation session termination event. The first suction operation session termination event may comprise any event that is predefined as a trigger event for terminating a first suction operation session—and may include any user input or any digital or analog signal, for example a user input provided through one or more buttons/switches or through a user interface provided on or coupled with the apparatus 100, 100', 100". In response to detection of a first suction operation session termination event, the first suction operation session is terminated or concluded.

In an embodiment of the method of FIG. 28, application of suction (at step 2802) upto detection of a first suction operation session termination event comprises applying suction in a continuous or pulsed operation cycle comprising alternately (i) generating negative pressure at the receptacle, and (ii) delivering fluid (for example, a liquid, a gas, water or air) to a region where the receptacle is positioned. In an embodiment, delivery of fluid may be implemented through a fluid outlet wherein the fluid outlet is coupled with a fluid source by a fluid channel that provides a fluid path between fluid source and the fluid outlet. In another embodiment, where the fluid is air, delivery of the fluid may occur through air vents or air channels or holes provided within the receptacle, or within a conduit connected to the receptacle, or at a junction of the receptacle and said conduit—wherein said air vents or holes allow air to be drawn in from the external environment in response to a negative pressure being generated at the receptacle. In a specific embodiment, the fluid outlet is one of the air or fluid outlets that re illustrated and described in connection with FIGS. 6C, 9A to 9E, 11A-11D and 12A to 12B. In a further embodiment, delivery of the fluid to the region wherein the receptacle is positioned, is controlled in accordance with one or more of predefined pressure, volume, flow or time parameters—i.e. fluid is delivered at a predefined fluid delivery pressure, and/or in a predefined volume, and/or in a predefined flow rate, and/or for a predefined delivery duration.

The application of suction (at step 2802) is continued until a first suction operation session termination event is detected. In response to detection of a first suction operation session termination event, the first suction operation session is terminated. A first suction operation session termination event may comprise any event that is predefined as a trigger event for terminating a first suction operation session—and may include any user input or any digital or analog signal, for example a user input provided through one or more switches/buttons or through a user interface provided on or coupled with the apparatus 100, 100', 100". In response to detection of a first suction operation session termination event, the first suction operation session is terminated—wherein termination of the first suction operation session comprises terminating application of suction for generating negative pressure at the receptacle.

Step 2804 comprises responding to either of (i) determining elapse of a predetermined interval of time from occurrence of a predefined event associated with a preceding suction operation session (for example the first, suction operation session at step 2802), and/or (ii) detection of a next suction pump operation session initiation event—by implementing a next suction operation session. A predetermined interval of time for the purposes of step 2804 may comprise any defined time interval between a previous suction operation session and a successive suction operation session. A next suction pump operation session initiation event may comprise any event that is predefined as a trigger event for initiating a next suction operation session—and may include any user input or any digital or analog signal, for example a user input provided through one or more switches/buttons or through a user interface provided on or coupled with the apparatus 100, 100', 100", or may include a determination that a predetermined interval of time has elapsed since occurrence of a predefined event associated with a preceding suction operation session (for example the first, suction operation session at step 2802). In response to determining that a predetermined interval of time has elapsed from occurrence of a predefined event associated with a preceding suction operation session (for example the first, suction operation session at step 2802), or detecting a next suction operation session initiation event—the next suction operation session is implemented. In an embodiment, the next suction operation session is initiated between at least 0.5 seconds after termination of the first suction operation session. In another embodiment, the next suction operation session is initiated prior to elapse of 240 minutes after termination of the first suction operation session. In another embodiment, the next suction operation session is initiated between 0.5 second and 240 minutes after termination of the first suction operation session.

Implementing the next suction operation session comprises initiating application of suction, for generating negative pressure at the receptacle (for example receptacle 200, 200', 200", 200'", 200"") of the apparatus 100, 100', 100". Suction may be applied at the receptacle through any mechanism for applying suction that is either internal to the apparatus 100, 100', 100" (for example suction pump 1312, suction pump 1512) or through any other suction or suction pump or any other source of suction that is external to the apparatus 100, 100', 100". The suction is applied upto detection of a next suction operation session termination event. The next suction operation session termination event may comprise any event that is predefined as a trigger event for terminating a next suction operation session—and may include any user input or any digital or analog signal, for example a user input provided through one or more switches/buttons or through a user interface provided on or coupled with the apparatus 100, 100', 100". In response to detection of a next suction operation session termination event, the next suction operation session is terminated or concluded. In an embodiment, initiating application of suction within the next suction operation session occurs at least 0.5 second after terminating application of suction within the first suction session. In another embodiment, initiating application of suction within the next suction operation session occurs not more than 240 minutes after terminating application of suction within the first suction session. In an embodiment, initiating application of suction within the next suction operation session occurs between 0.5 second and 240 minutes after terminating application of suction within the first suction session. Critically, the receptacle is (or remains) positioned at least partially within a patient's lower gastrointestinal tract for the interval of time separating the application of suction within the first suction session and the initiation of application of suction within the next suction operation session.

In an embodiment of the method of FIG. 28, application of suction (at step 2804) upto detection of a next suction operation session termination event comprises applying suction in a continuous or pulsed operation cycle comprising alternately (i) generating negative pressure at the receptacle, and (ii) delivering fluid (for example, a liquid, a gas, water or air) to a region where the receptacle is positioned, through a fluid outlet wherein the fluid outlet is coupled with a fluid source by a fluid channel that provides a fluid path between fluid source and the fluid outlet. In a specific embodiment, the fluid outlet is one of the air or fluid outlets that re illustrated and described in connection with FIGS. 6C, 9A to 9E, 11A-11D and 12A to 12B. In a further embodiment, delivery of the fluid to the region wherein the receptacle is positioned, is controlled in accordance with one or more of predefined pressure, volume flow, or time parameters—i.e. fluid is delivered at a predefined fluid delivery pressure, and/or in a predefined volume, and/or in a predefined flow rate, and/or for a predefined delivery duration.

The application of suction (at step 2804) is continued until a next suction operation session termination event is detected. In response to detection of a next suction operation session termination event, the next suction operation session is terminated or concluded. A next suction operation session termination event may comprise any event that is predefined as a trigger event for terminating a next suction operation session—and may include any user input or any digital or analog signal, for example a user input provided through one or more switches/buttons or through a user interface provided on or coupled with the apparatus 100, 100', 100". In response to detection of a next suction operation session termination event, the next suction operation session is terminated or concluded.

Step 2806 is an optional step, comprising repeating step 2804 upto detection of an event signaling termination of further suction operation sessions—for example a user input or a signal switching the apparatus 100, 100', 100" off or to a standby mode or power saver mode.

By repeatedly cycling through successive suction operation sessions—each separated by a predefined interval of time, the apparatus 100, 100', 100" periodically (and regularly) evacuates the contents of a subject's or user's rectum—thereby preventing accumulation or build-up of substantial amount of fecal matter in the rectum. This has been found to be advantageous for immobile patients (such as patients in an intensive care unit) as it eliminates the need to periodically remove or clean up fecal matter that is voluntarily or involuntarily expelled from the patient's rectum through bowel movement, as well as the various problems associated with incontinent patients such as constipation and stool impaction.

Figure 29:
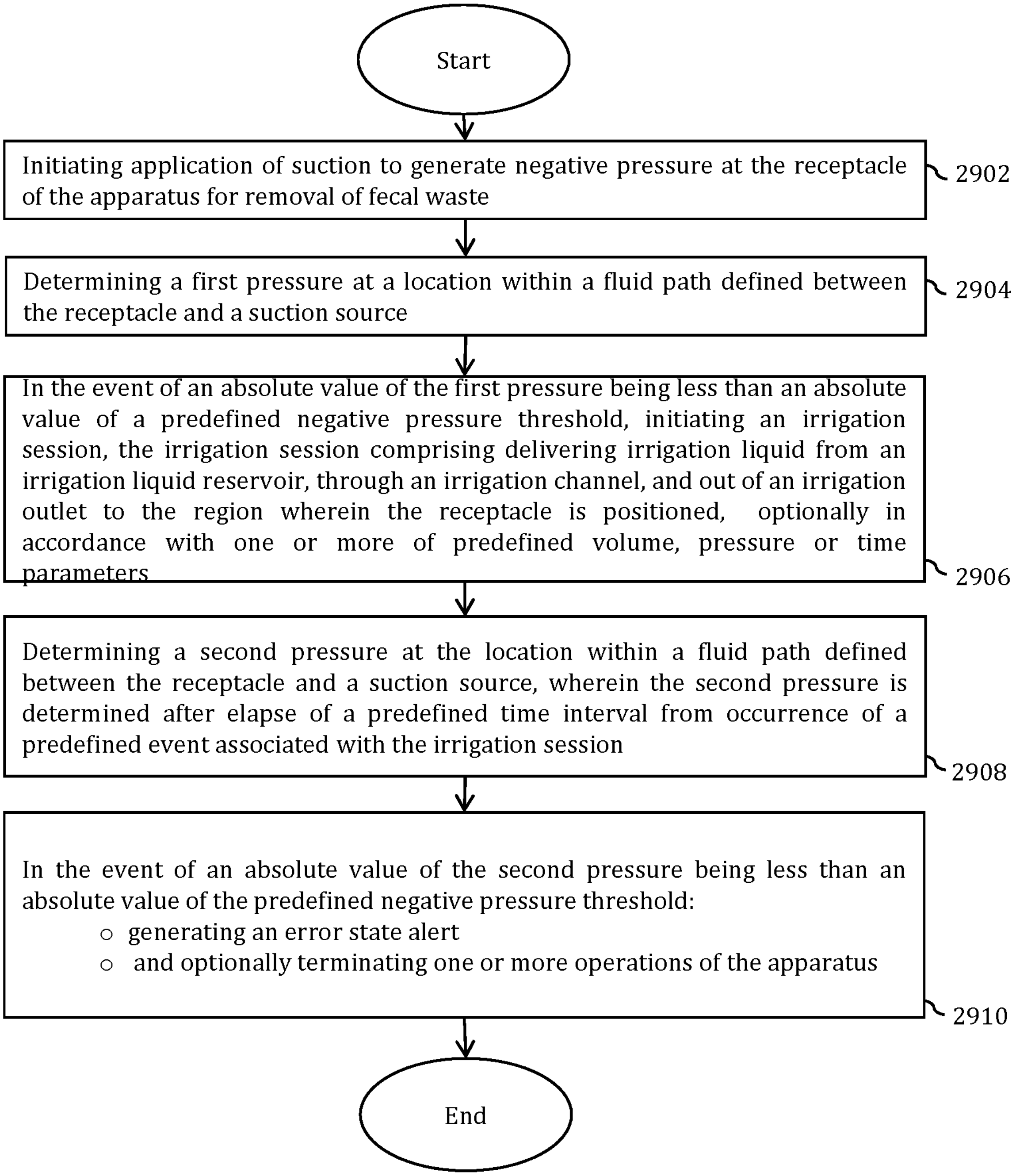
FIG. 29 is a flowchart illustrating a method for detecting an error state in a fecal management apparatus.

FIG. 29 is a flowchart illustrating a method according to the teachings of the present invention—wherein the method comprises method steps for detecting an error state in a fecal management apparatus (according to any of the embodiments described in connection with FIGS. 1 to 27F hereinabove). Detection of an error state in the placement or operation of such apparatuses ensures that the apparatuses are in fact disposed and utilized in a manner that enables such apparatuses to successfully implement the intended functionality of such apparatuses.

By way of example, factors that have been found to significantly give rise to an error state of an apparatus 100, 100', 100" have been (i) failure to position the receptacle (for example receptacle 200, 200', 200", 200'", 200"") of the apparatus 100, 100', 100" properly within the subject's/user's anal anatomy, and (ii) atonicity of the subject's sphincter, and/or (iii) an improper connection between, or a failure to connect, components of apparatus 100, 100', 100" that are supposed to be joined in a fluid tight or air tight manner—as a result of any of which, suction applied within a subject's rectum does not result in fecal matter being drawn out of the rectum, and instead simply results in air being drawn into the receptacle through gaps between a stem of the receptacle, e.g. 532 and the adjacent walls of the sphincter or through unconnected or loosely connected components, and thereafter out of the system by action of the applied suction. The method of FIG. 29 enables detection of any one or more of these error states—and may therefore be implemented as a precursor to or during any of the other methods for removing fecal matter from a subject's rectum (for example as a precursor to or during the methods of any of FIGS. 28, 31 and 32).

In various embodiments, the method of FIG. 29 may be implemented through one or more processors or controllers configured to control the apparatus(es) of the present invention based on the method steps of said method. In an exemplary embodiment, the method of FIG. 29 is implemented for detecting an error state in any of the apparatuses 100, 100', 100" that have been described in detail hereinabove. The method of FIG. 29 may be performed by implementing one or more of steps 2902 to 2910 as described in detail below.

Step 2902 comprises initiating application of suction to generate negative pressure at the receptacle (for example receptacle 200, 200', 200", 200'", 200"") of the apparatus 100, 100', 100". Suction may be applied at the receptacle through any mechanism or source for applying suction that is either internal to the apparatus 100, 100', 100" (for example suction pump 1312, suction pump 1512) or through any other suction or suction pump or any other source of suction that is external to the apparatus 100, 100', 100".

Step 2904 comprises determining a first pressure at a location within a fluid path defined between the receptacle and a suction source. Determination of pressure may be achieved through a pressure sensor located within or configured to determine pressure within a fluid path defined between the receptacle and the suction source.

In the event an absolute value of the first pressure is less than an absolute value of a predefined negative pressure threshold, step 2906 comprises initiating an irrigation session—wherein the irrigation session comprises delivering irrigation liquid from an irrigation liquid reservoir (e.g. first side 2071 of collection bag 2000), through an irrigation channel 1265, and out of an irrigation outlet 1245 to the region wherein the receptacle is positioned. In an embodiment, delivery of the irrigation liquid to the region wherein the receptacle is positioned, is controlled in accordance with one or more of predefined pressure, volume flow or time parameters—i.e. irrigation liquid is delivered at a predefined liquid delivery pressure, and/or in a predefined volume, and/or in a predefined flow rate, and/or for a predefined delivery duration. The predefined negative pressure threshold may comprise any negative pressure threshold that is selected according to the dimensions of the apparatus and its components—and may be selected such that detection of an event or occurrence wherein absolute value of negative pressure measured at step 2906 is less than an absolute value of the predefined negative pressure threshold, may be understood as being indicative that negative pressure that is being generated at the receptacle is insufficient for successful implementation of the present invention's methods of evacuating fecal matter from a subject's/patient's rectum.

Step 2908 thereafter comprises determining a second pressure at the location within a fluid path defined between the receptacle and a suction source—wherein the second pressure is determined after elapse of a predefined time interval from occurrence of a predefined event associated with the irrigation session. Again, determination of pressure may be achieved through a pressure sensor located within or configured to determine pressure within a fluid path defined between the receptacle and the suction.

In the event of an absolute value of the second pressure being less than an absolute value of the predefined negative pressure threshold, step 2910 comprises generating an error state alert (for example alerting a care provider to check if the receptacle 200, 200', 200", 200'", 200' is properly positioned within the subject's anatomy), and optionally terminating one or more operations of the apparatus (for example, with a view to enable the error state to be rectified prior to resumption of such operations).

Figure 30:
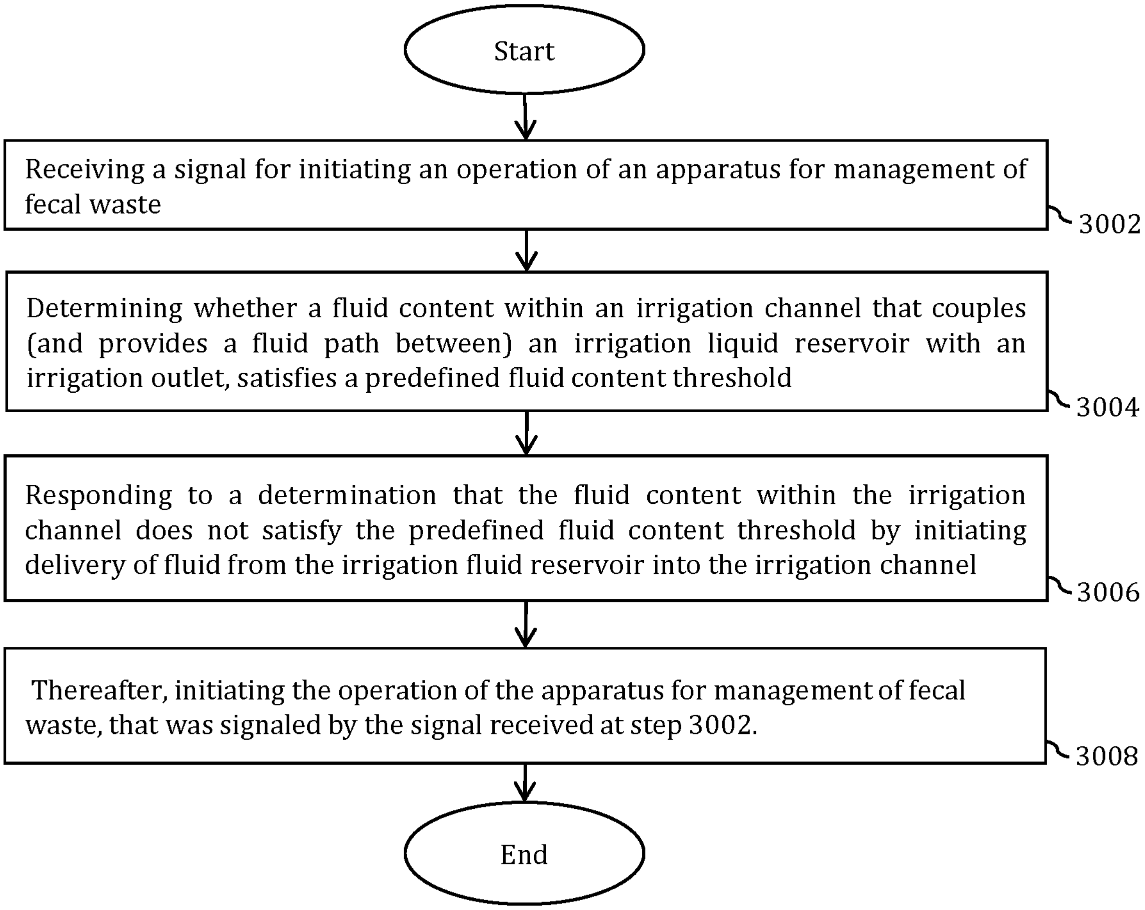
FIG. 30 is a flowchart illustrating a method for priming an irrigation channel within a fecal management apparatus with fluid/water.

FIG. 30 is a flowchart illustrating a method according to the teachings of the present invention—wherein the method comprises method steps for priming an irrigation channel (for example, irrigation channel 1265) with fluid/water prior to or while initiating operation of the apparatus for the purposes of removal of fecal matter from a subject's rectum. By ensuring that the irrigation channel is primed prior to operation, the method of FIG. 30 eliminates the likelihood of errors arising due to an irrigation liquid reservoir (e.g. first side 2071 of collection bag 2000) being depleted or empty, or due to time taken for liquid to be drawn from the irrigation liquid reservoir through the irrigation channel and thereafter delivered out of an irrigation outlet (e.g. irrigation outlet 1245) into a subject's rectum. The method of FIG. 30 may therefore be implemented as a precursor to any of the other methods for removing fecal matter from a subject's rectum (for example as a precursor to the methods of any of FIGS. 28, 31 and 32).

In various embodiments, the method of FIG. 30 may be implemented through one or more processors of controllers configured to control the apparatus(es) of the present invention based on the method steps of said method. In an exemplary embodiment, the method of FIG. 30 is implemented for ensuring priming of an irrigation channel in any of the apparatuses 100, 100', 100" that have been described in detail hereinabove. The method of FIG. 30 may be performed by implementing one or more of steps 3002 to 3008 as described in detail below.

Step 3002 comprises receiving a signal for initiating an operation of an apparatus for management of fecal waste. The received signal may comprise any user input or any digital or analog signal, for example a user input provided through one or more switches/buttons or through a user interface provided on or coupled with the apparatus 100, 100', 100". In an embodiment, the operation that is initiated by the received signal is an operation that applies suction to generate negative pressure at the receptacle (for example receptacle 200, 200', 200", 200'", 200') of the apparatus 100, 100', 100".

Step 3004 comprises determining whether an irrigation fluid content (e.g. water content) within an irrigation channel (e.g. irrigation channel 1265) that couples (and provides a fluid path between) an irrigation liquid reservoir (e.g. first side 2071 of collection bag 2000) with an irrigation outlet (e.g. irrigation outlet 1245), satisfies a predefined fluid content threshold. In an embodiment, the predefined fluid content threshold may comprise presence of fluid, a predefined fluid volume value, a predefined fluid pressure value, or a predefined location at which fluid is determined to be either present or not present.

Step 3006 comprises responding to a determination that the fluid content within the irrigation channel does not satisfy the predefined fluid content threshold, by initiating delivery of fluid from the irrigation fluid reservoir into the irrigation channel, for example, by using a fluid pump or gravity to impel fluid from the irrigation fluid reservoir into the irrigation channel. In the event the irrigation fluid reservoir is found to be empty, the irrigation fluid reservoir may first require to be refilled before initiating delivery of fluid from the irrigation fluid reservoir into the irrigation channel.

Thereafter, step 3008 comprises initiating the operation of the apparatus for management of fecal waste that was signaled by the signal received at step 3002. In an embodiment, step 3008 comprises thereafter initiating application of a suction, to generate negative pressure at the receptacle (for example receptacle 200, 200', 200", 200'", 200') of the apparatus 100, 100', 100".

Figure 31:
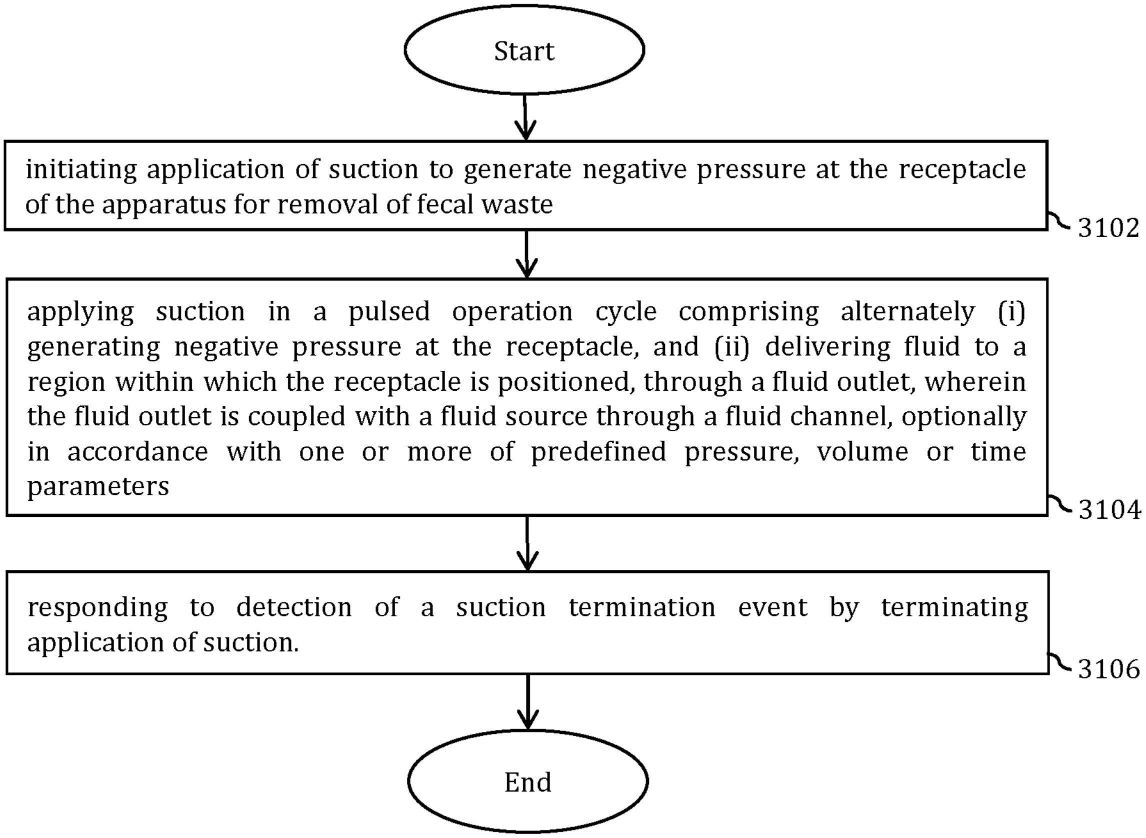
FIG. 31 is a flowchart illustrating a first method for controlling application of suction within a fecal management apparatus.

FIG. 31 is a flowchart illustrating a method according to the teachings of the present invention—wherein the method comprises method steps for controlling application of suction within a fecal management apparatus (according to any of the embodiments described in connection with FIGS. 1 to 27F hereinabove) for optimizing evacuation of fecal matter from the rectum of a subject or user of said apparatus. The method of FIG. 31 has been particularly efficient at eliminating blockages in the apparatus arising as a result of vacuum locks and/or blockages caused by high viscosity of fecal matter and/or high density of fecal matter and/or accumulation of substantial amount of fecal matter within tubes provided for transport of fecal matter away from the rectum (e.g. within connecting tube 105).

In various embodiments, the method of FIG. 31 may be implemented through one or more processors or controllers configured to control the apparatus(es) of the present invention based on the method steps of said method. In an exemplary embodiment, the method of FIG. 31 is implemented for controlling any of the apparatuses 100, 100', 100" that have been described in detail hereinabove. The method of FIG. 31 may be performed by implementing one or more of steps 3102 to 3106 as described in detail below.

Step 3102 comprises initiating application of suction to generate negative pressure at the receptacle (for example receptacle 200, 200', 200", 200'", 200'"") of the apparatus 100, 100', 100". Suction may be applied at the receptacle through any mechanism or source for applying suction that is either internal to the apparatus 100, 100', 100" (for example suction pump 1312, suction pump 1512) or through any other suction or suction pump or any other source of suction that is external to the apparatus 100, 100', 100".

Step 3104 comprises controlling the apparatus 100, 100', 100" and/or one or more components of said apparatus, and/or the suction source that is generating the suction, to apply suction in a continuous or pulsed operation cycle comprising alternately (i) generating negative pressure at the receptacle, and (ii) delivering fluid (for example, a liquid, a gas, water or air) to a region where the receptacle is positioned, through a fluid outlet wherein the fluid outlet is coupled with a fluid source by a fluid channel that provides a fluid path between fluid source and the fluid outlet. In a specific embodiment, the fluid outlet is one of the air or fluid outlets that are illustrated and described in connection with FIGS. 6C, 9A to 9E, 11A-11D and 12A to 12B. In a further embodiment, delivery of the fluid to the region wherein the receptacle is positioned, is controlled in accordance with one or more of predefined pressure, volume, flow or time parameters—i.e. fluid is delivered at a predefined fluid delivery pressure, and/or in a predefined volume, and/or in a predefined flow rate, and/or for a predefined delivery duration.

At step 3106, in response to detection of a suction termination event, the application of suction to the receptacle is terminated. A suction termination event may comprise any event that is predefined as a trigger event for terminating application of suction to the receptacle—and may include any user input or any digital or analog signal, for example a user input provided through one or more switches/buttons or through a user interface provided on or coupled with the apparatus 100, 100', 100". In response to detection of a suction termination event, the application of suction to the receptacle is terminated.

Figure 32:
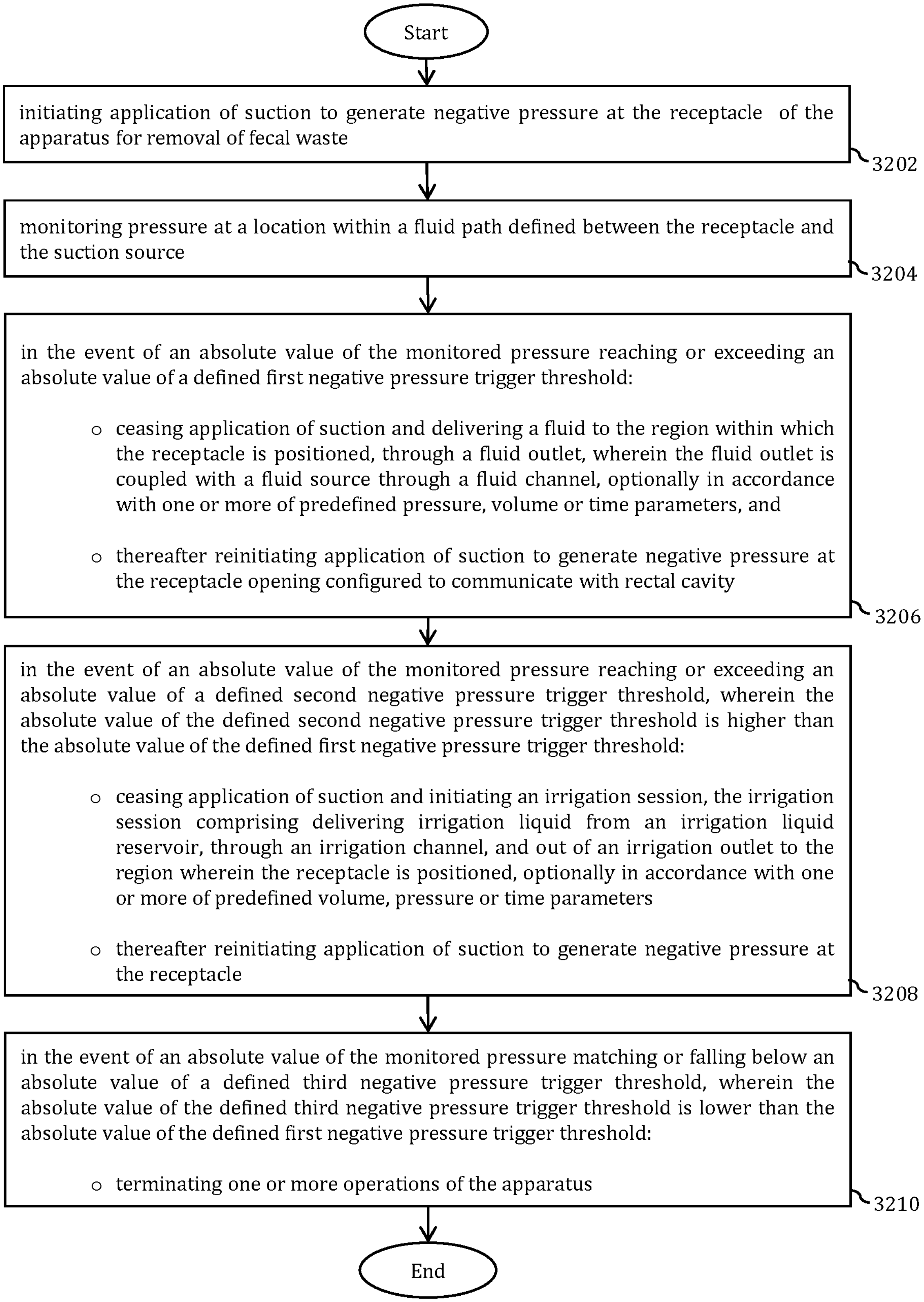
FIG. 32 is a flowchart illustrating a second method for controlling application of suction within a fecal management apparatus.

FIG. 32 is a flowchart illustrating another method according to the teachings of the present invention—wherein the method comprises method steps for controlling application of suction within a fecal management apparatus (according to any of the embodiments described in connection with FIGS. 1 to 27F hereinabove) for optimizing evacuation of fecal matter from the rectum of a subject or user of said apparatus. The method of FIG. 32 improves elimination of blockages in the apparatus arising as a result of vacuum locks and/or blockages caused by high viscosity of fecal matter and/or high density of fecal matter and/or accumulation of substantial amount of fecal matter within tubes provided for transport of fecal matter away from the rectum (e.g. within connecting tube 105).

In various embodiments, the method of FIG. 32 may be implemented through one or more processors or controllers configured to control the apparatus(es) of the present invention based on the method steps of said method. In an exemplary embodiment, the method of FIG. 32 is implemented for controlling any of the apparatuses 100, 100', 100" that have been described in detail hereinabove. The method of FIG. 32 may be performed by implementing one or more of steps 3202 to 3210 as described in detail below.

Step 3202 comprises initiating application of suction to generate negative pressure at the receptacle (for example receptacle 200, 200', 200", 200'", 200'"") of the apparatus 100, 100', 100". Suction may be applied at the receptacle through any mechanism or source for applying suction that is either internal to the apparatus 100, 100', 100" (for example suction pump 1312, suction pump 1512) or through any other suction or suction pump or any other source of suction that is external to the apparatus 100, 100', 100".

Step 3204 comprises monitoring a pressure at a location within a fluid path defined between the receptacle and a suction source. Determination of pressure may be achieved through a pressure sensor located within or configured to determine pressure within a fluid path defined between the receptacle and the suction source.

In the event an absolute value of the monitored pressure reaches or exceeds an absolute value of a predefined first negative pressure trigger threshold, step 3206 comprises (i) ceasing application of the suction and (ii) delivering fluid (for example, a liquid, a gas, water or air) to a region where the receptacle is positioned, through a fluid outlet, wherein the fluid outlet is coupled with a fluid source by a fluid channel that provides a fluid path between fluid source and the fluid outlet. In a specific embodiment, the fluid outlet is one of the air or fluid outlets that are illustrated and described in connection with FIGS. 11A-11D. In a further embodiment, delivery of the fluid to the region wherein the receptacle is positioned, is controlled in accordance with one or more of predefined pressure, volume, flow or time parameters—i.e. fluid is delivered at a predefined fluid delivery pressure, and/or in a predefined volume, and/or in a predefined flow rate, and/or for a predefined delivery duration.

Subsequent to delivery of the fluid to the region within which the receptacle is positioned, step 3206 further comprises reinitiating application of suction to generate negative pressure at the receptacle.

The outcome of implementing step 3206 is to eliminate blockages arising out of a vacuum lock condition—wherein continued application of a suction fails to result in further movement or evacuation of fecal matter due to the vacuum lock that has been generated. By ceasing application of the suction and delivering a fluid to the region within which the receptacle is positioned, step 3206 alleviates, reduces or eliminates the vacuum lock condition—such that when application of suction is reinitiated, fecal matter can once again be evacuated or drawn from the subject's rectum and into a container within the apparatus.

In the event an absolute value of the monitored pressure reaches or exceeds an absolute value of a predefined second negative pressure trigger threshold, wherein the absolute value of the defined second negative pressure trigger threshold is higher than the absolute value of the defined first negative pressure trigger threshold, step 3208 comprises (i) ceasing application of the suction and (ii) initiating an irrigation session—wherein the irrigation session comprises delivering irrigation liquid from an irrigation liquid reservoir (e.g. first side 2071 of collection bag 2000), through an irrigation channel 1265, and out of an irrigation outlet 1245 to the region wherein the receptacle is positioned. In an embodiment, delivery of the irrigation liquid to the region wherein the receptacle is positioned, is controlled in accordance with one or more of predefined pressure, volume, flow or time parameters—i.e. irrigation liquid is delivered at a predefined liquid delivery pressure, and/or in a predefined volume, and/or in a predefined flow rate, and/or for a predefined delivery duration.

Subsequent to delivery of irrigation liquid to the region within which the receptacle is positioned, step 3208 further comprises reinitiating application of suction to generate negative pressure at the receptacle.

The outcome of implementing step 3208 is to eliminate blockages arising out of fecal matter within the rectum having a high viscosity or high density or high level of compaction, which results in high resistance to the applied negative pressure—and wherein continued application of a suction therefore fails to result in further movement or sufficiently fast evacuation of fecal matter. By ceasing application of the suction and delivering an irrigation liquid to the region within which the receptacle is positioned, step 3208 reduces the viscosity, density and/or compaction of the fecal matter—such that when application of suction is reinitiated, fecal matter can once again be evacuated or drawn from the subject's rectum and into a container within the apparatus.

In the event an absolute value of the monitored pressure matches or falls below an absolute value of a predefined third negative pressure trigger threshold, wherein the absolute value of the defined third negative pressure trigger threshold is lower than the absolute value of the defined first negative pressure trigger threshold, step 3210 comprises terminating one or more operations of the apparatus. In an embodiment, an operation terminating one or more operations of the apparatus at step 3210 comprises terminating application of suction at the receptacle.

The outcome of implementing step 3210 is to terminate application of suction in case an error state develops. An error state of the kind that would lead to termination of application of suction at step 3210 may arise from (i) failure to position the receptacle (for example receptacle 200, 200', 200", 200'", 200"") of the apparatus 100, 100', 100" properly within the subject's/user's anal anatomy, (ii) atonicity of the subject's sphincter, and/or (iii) in the event a fluid path between the receptacle and the suction source is partially or wholly or substantially wholly blocked—any of which can be identified by identifying when an absolute value of the monitored pressure monitored pressure matches or falls below an absolute value of a predefined minimum pressure threshold. It would be therefore be understood that the defined third negative pressure trigger threshold is selected/defined such that a monitored pressure having an absolute value lower that the absolute value of said defined third negative pressure value is indicative of an error state.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Figure 33:
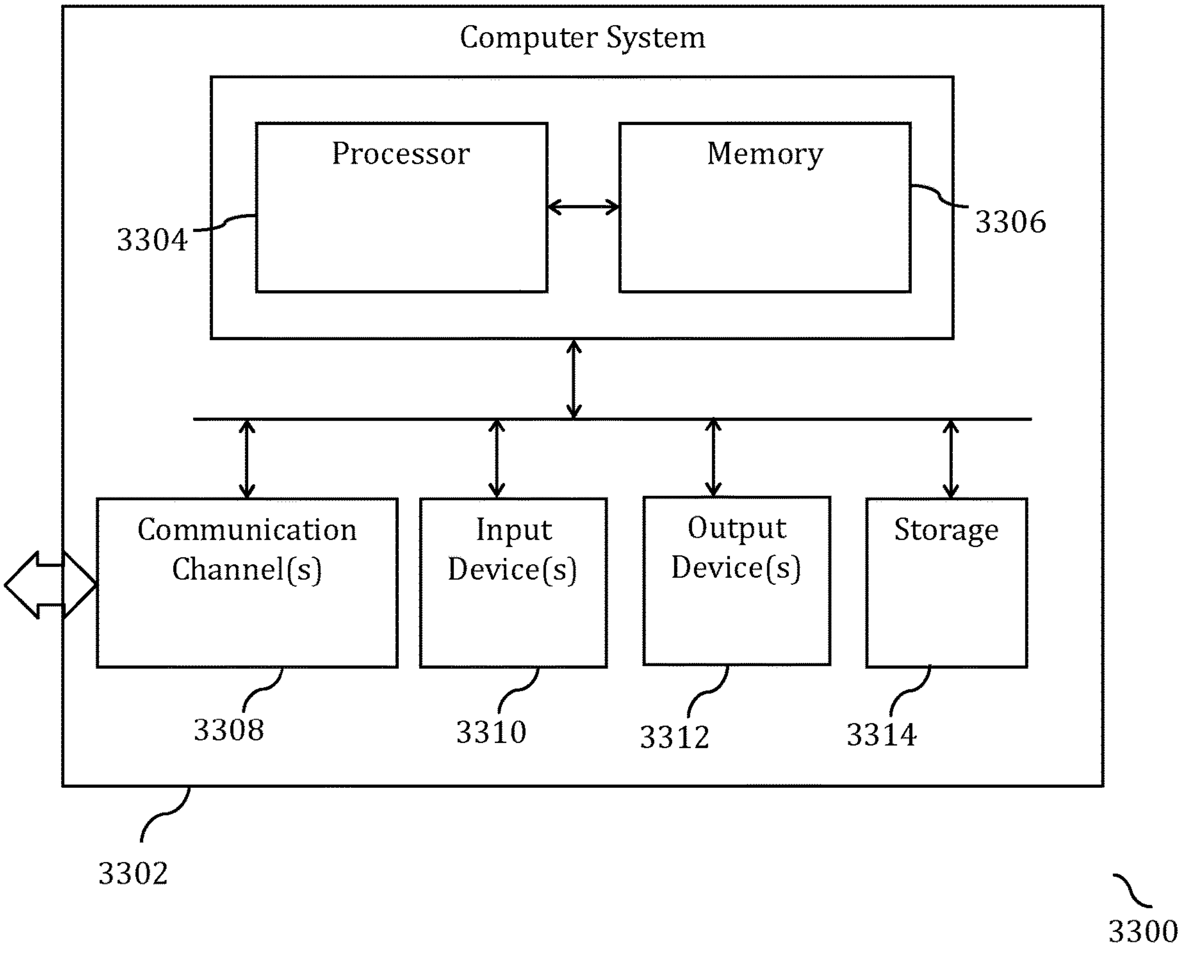
FIG. 33 illustrates an exemplary system 3300 for implementing the present invention.

FIG. 33 illustrates an exemplary system 3300 for implementing the present invention. The illustrated system 3300 comprises computer system 3302 which in turn comprises one or more processors 3304, at least one memory 3306 and optionally one or more internal or external power sources (not shown in FIG. 33). Processor 3304 is configured to execute program instructions—and may be a real processor or a virtual processor. It will be understood that computer system 3302 does not suggest any limitation as to scope of use or functionality of described embodiments. The computer system 3302 may include, but is not be limited to, one or more of a general-purpose computer, a programmed microprocessor, a micro-controller, an integrated circuit, and other devices or arrangements of devices that are capable of implementing the steps that constitute the method of the present invention. Exemplary embodiments of a computer system 3302 in accordance with the present invention may include one or more servers, desktops, laptops, tablets, smart phones, mobile phones, mobile communication devices, tablets, phablets and personal digital assistants. In an embodiment of the present invention, the memory 3306 may store software for implementing various embodiments of the present invention. The computer system 3302 may have additional components. For example, the computer system 3302 may include one or more communication channels 3308, one or more input devices 3310, one or more output devices 3312, and storage 3314. An interconnection mechanism (not shown) such as a bus, controller, or network, interconnects the components of the computer system 3302. In various embodiments of the present invention, operating system software (not shown) provides an operating environment for various softwares executing in the computer system 3302 using a processor 3304, and manages different functionalities of the components of the computer system 3302.

The communication channel(s) 3308 allow communication over a communication medium to various other computing entities. The communication medium provides information such as program instructions, or other data in a communication media. The communication media includes, but is not limited to, wired or wireless methodologies implemented with an electrical, optical, RF, infrared, acoustic, microwave, Bluetooth or other transmission media.

The input device(s) 3310 may include, but is not limited to, a touch screen, a keyboard, mouse, pen, joystick, trackball, a voice device, a scanning device, or any another device that is capable of providing input to the computer system 3302. In an embodiment of the present invention, the input device(s) 3310 may be a sound card or similar device that accepts audio input in analog or digital form. The output device(s) 3312 may include, but not be limited to, a user interface on CRT, LCD, LED display, or any other display associated with any of servers, desktops, laptops, tablets, smart phones, mobile phones, mobile communication devices, tablets, phablets and personal digital assistants, printer, speaker, CD/DVD writer, or any other device that provides output from the computer system 3302.

The storage 3314 may include, but not be limited to, magnetic disks, magnetic tapes, CD-ROMs, CD-RWs, DVDs, any types of computer memory, magnetic stripes, smart cards, printed barcodes or any other transitory or non-transitory medium which can be used to store information and can be accessed by the computer system 3302. In various embodiments of the present invention, the storage 3314 may contain program instructions for implementing any of the described embodiments.

In an embodiment of the present invention, the computer system 3302 is part of a distributed network or a part of a set of available cloud resources.

The present invention may be implemented in numerous ways including as a system, a method, or a computer program product such as a computer readable storage medium or a computer network wherein programming instructions are communicated from a remote location.

The present invention may suitably be embodied as a computer program product for use with the computer system 3302. The method described herein is typically implemented as a computer program product, comprising a set of program instructions that is executed by the computer system 3302 or any other similar device. The set of program instructions may be a series of computer readable codes stored on a tangible medium, such as a computer readable storage medium (storage 3314), for example, diskette, CD-ROM, ROM, flash drives or hard disk, or transmittable to the computer system 3302, via a modem or other interface device, over either a tangible medium, including but not limited to optical or analogue communications channel(s) 3308. The implementation of the invention as a computer program product may be in an intangible form using wireless techniques, including but not limited to microwave, infrared, Bluetooth or other transmission techniques. These instructions can be preloaded into a system or recorded on a storage medium such as a CD-ROM, or made available for downloading over a network such as the Internet or a mobile telephone network. The series of computer readable instructions may embody all or part of the functionality previously described herein.

While disclosed embodiments allows the user to measure stool output using the graduated marking on the collection bag as illustrated in FIGS. 20A to 20D and 21A to 21C, a more accurate or automated output measurement can be achieved in another embodiment of the present invention by using one or more optical, electrical, mechanical or electromechanical sensors, to measure flow rate, weight, volume of the stool removed from the rectum or weight, level, quantity, size, etc. of the stool collected in the collection chamber. One or more of these sensors can be integrated anywhere along the path taken by the stool from the receptacle to the collection chamber. The measured value of the stool can further be communicated to the user via indicator or digital/analogue display integrated with the product or be communicated using wired or one or more wireless connection methods to a separate and/or remote monitoring device or integrated with hospital electronic medical record system. Similarly, while the disclosed embodiments allow for the delivery of irrigation fluid from the fluid reservoir to the rectum, another embodiment of the present invention can be configured to deliver one or more medicinal or other fluids into the patient rectum either from the irrigation reservoir or one or more additional reservoirs. The fluids can be pumped using the irrigation fluid delivery/transport mechanism (e.g. fluid pump) or one more additional delivery/transport mechanism (e.g. pump, gravity, etc.) employed individually or collectively to deliver the said fluid from the said reservoir to the area where the receptacle is positioned. The quantity, flow rate, volume, etc. of the said fluid delivered in the area where the receptacle is positioned, can be controlled using control switches/buttons or user interface integrated with the product or from a separate device in wired or wireless communication with the present invention.

Further, the present invention can be configured with additional optical, mechanical, electrical or electromechanical sensors to measure body temperature, intra-rectal pressure, stool pH, stool consistency, stool water content, concentration of gases or to detect presence or absence of blood, *C. Diff* bacteria and other stool pathogens. The outcome of such measurements or detection methods can further be communicated to the user via indicator or digital/analogue display integrated with the product or be communicated using wired or one or more wireless connection methods to a separate and/or remote monitoring device or integrated with hospital electronic medical record system.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The terms 'vacuum' and 'suction' are used interchangeably throughout the specification and reference to generation or application of either 'vacuum' or 'suction' or 'negative pressure' shall be understood as a reference to generation or application of negative pressure state.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for controlling an apparatus configured for removal of fecal material from a patient's rectum, wherein the apparatus includes a receptacle configured to be positioned at least partially at a patient's anorectal junction, a connecting tube comprising at least a suction channel, the connecting tube configured to couple the suction channel to a suction port of the receptacle, one or more sensors in communication with the receptacle, and a controller configured to apply a plurality of fecal removal cycles including applying suction through the suction port and by controlling a source of negative pressure to deliver suction, the method comprising preventing buildup of fecal material within the rectum for the duration of the plurality of fecal removal cycles by:

responding to detection of a first suction operation session initiation event, by implementing a first suction operation session wherein implementation of the first suction operation session comprises:

applying suction for generating negative pressure at the receptacle; and responding to detection of a first suction operation session termination event by terminating the first suction operation session, and wherein terminating the first suction operation session comprises terminating application of suction for generating negative pressure at the receptacle;

implementing a next suction operation session in response to elapse of a predetermined time duration from termination of the first suction operation session, wherein implementation of the next suction operation session comprises:

applying suction for generating negative pressure at the receptacle; and responding to detection of a next suction operation session termination event by terminating the next suction operation session, and wherein terminating the next suction operation session comprises terminating application of suction for generating negative pressure at the receptacle;

wherein during the predetermined time duration between the termination of the first suction operation session and implementing of the next suction operation session, none of suction, irrigation or fluid movement is implemented within the apparatus and within the patient's rectum;

wherein triggering of pain signals from somatic nerves is avoided by positioning the receptacle at the patient's anorectal junction above the somatic nerve boundary at the anorectal junction, for the duration of the plurality of fecal removal cycles; and wherein the controller determines parameter(s) of one or more of the applied fecal removal cycles using sensor data received from the one or more sensors, wherein said sensor data indicates a condition within the patient's rectum.

2. The method as claimed in claim 1, wherein the next suction operation session, is implemented in response to either of:

determining elapse of a predetermined interval of time from occurrence of a predefined event associated with a preceding suction operation session; and detection of a next suction pump operation session initiation event.

3. The method as claimed in claim 1, wherein within the first suction operation session, applying suction for generating negative pressure at the receptacle comprises applying suction in a pulsed operation cycle, said pulsed operation cycle comprising alternately:

generating negative pressure at the receptacle, and delivering fluid to a region where the receptacle is positioned, through a fluid outlet wherein the fluid outlet is coupled with a fluid source by a fluid channel that provides a fluid path between fluid source and the fluid outlet.

4. The method as claimed in claim 3, wherein the fluid delivered through a fluid outlet is a liquid or a gas.

5. The method as claimed in claim 3, wherein the step of responding to detection of any of the first suction operation session initiation event or the second suction operation session event, includes performing prior to implementing respectively the first suction operation session or the second suction operation session, the step of:

determining whether a fluid content within the fluid channel satisfies a predefined fluid content threshold.

6. The method as claimed in claim 5, wherein the step of responding to detection of any of the first suction operation session initiation event or the second suction operation session event, includes performing prior to implementing respectively the first suction operation session or the second suction operation session, the step of:

responding to a determination that the fluid content within the fluid channel does not satisfy the predefined fluid threshold, by delivering fluid from the fluid source into the fluid channel.

7. The method as claimed in claim 1, wherein within the second suction operation session, applying suction for generating negative pressure at the receptacle comprises applying suction in a pulsed operation cycle comprising alternately:

generating negative pressure at the receptacle, and delivering fluid to a region where the receptacle is positioned, through a fluid outlet wherein the fluid outlet is coupled with a fluid source by a fluid channel that provides a fluid path between fluid source and the fluid outlet.

8. The method as claimed in claim 7, wherein the fluid delivered through a fluid outlet is a liquid or a gas.

9. The method as claimed in claim 1, wherein within any of the first suction operation session or the second suction operation session, the step of applying suction for generating negative pressure at the receptacle is followed by:

determining a first pressure at a location within a fluid path defined between the receptacle and a suction source;

responding to an absolute value of the first pressure being less than an absolute value of a predefined negative pressure threshold, by initiating fluid delivery from the fluid source and out of the fluid outlet through the fluid channels that provides a fluid path between the fluid source and the fluid outlet;

determining a second pressure at the location of the fluid path defined between the receptacle and the suction source, wherein the second pressure is determined after an elapse of a predefined time interval from occurrence of a predefined event associated with initiated fluid delivery; and responding to determining that an absolute value of the second pressure is less than the absolute value of the predefined negative pressure threshold, by generating an error state alert.

10. An apparatus configured for removal of fecal material from a patient's rectum, the apparatus comprising:

a receptacle configured to be positioned at least partially at a patient's anorectal junction;

a connecting tube comprising at least a suction channel, the connecting tube configured to couple the suction channel to a suction port of the receptacle;

one or more sensors in communication with the receptacle; and a processor implemented controller configured to apply a plurality of fecal removal cycles including applying suction through the suction port and by controlling a source of negative pressure to deliver suction;

wherein the controller is configured for preventing buildup of fecal material within the rectum for the duration of the plurality of fecal removal cycles by:

responding to detection of a first suction operation session initiation event, by implementing a first suction operation session wherein implementation of the first suction operation session comprises:

applying suction for generating negative pressure at the receptacle; and responding to detection of a first suction operation session termination event by terminating the first suction operation session, and wherein terminating the first suction operation session comprises terminating application of suction for generating negative pressure at the receptacle;

implementing a next suction operation session in response to elapse of a predetermined time duration from termination of the first suction operation session, wherein implementation of the next suction operation session comprises:

applying suction for generating negative pressure at the receptacle; and responding to detection of a next suction operation session termination event by terminating the next suction operation session, and wherein terminating the next suction operation session comprises terminating application of suction for generating negative pressure at the receptacle;

wherein during the predetermined time duration between the termination of the first suction operation session and implementing of the next suction operation session, none of suction, irrigation or fluid movement is implemented within the apparatus and within the patient's rectum;

wherein triggering of pain signals from somatic nerves is avoided by positioning the receptacle at the patient's anorectal junction above the somatic nerve boundary at the anorectal junction, for the duration of the plurality of fecal removal cycles; and wherein the controller is configured to determine parameter(s) of one or more of the applied fecal removal cycles using sensor data received from the one or more sensors, wherein said sensor data indicates a condition within the patient's rectum.

11. The apparatus as claimed in claim 10, wherein the controller is configured such that the next suction operation session, is implemented in response to either of:

determining elapse of a predetermined interval of time from occurrence of a predefined event associated with a preceding suction operation session; and detection of a next suction pump operation session initiation event.

12. The apparatus as claimed in claim 10, wherein the controller is configured such that, within the first suction operation session, applying suction for generating negative pressure at the receptacle comprises applying suction in a pulsed operation cycle, said pulsed operation cycle comprising alternately:

generating negative pressure at the receptacle, and delivering fluid to a region where the receptacle is positioned, through a fluid outlet wherein the fluid outlet is coupled with a fluid source by a fluid channel that provides a fluid path between fluid source and the fluid outlet.

13. The apparatus as claimed in claim 12, wherein the controller is configured such that the step of responding to detection of any of the first suction operation session initiation event or the second suction operation session event, includes performing prior to implementing respectively the first suction operation session or the second suction operation session, the step of:

determining whether a fluid content within the fluid channel satisfies a predefined fluid content threshold.

14. The apparatus as claimed in claim 13, wherein the controller is configured such that the step of responding to detection of any of the first suction operation session initiation event or the second suction operation session event, includes performing prior to implementing respectively the first suction operation session or the second suction operation session, the step of:

responding to a determination that the fluid content within the fluid channel does not satisfy the predefined fluid threshold, by delivering fluid from the fluid source into the fluid channel.

15. The apparatus as claimed in claim 12, wherein the fluid delivered through a fluid outlet is a liquid or a gas.

16. The apparatus as claimed in claim 10, wherein the controller is configured such that, within the second suction operation session, applying suction for generating negative pressure at the receptacle comprises applying suction in a pulsed operation cycle, said pulsed operation cycle comprising alternately:

generating negative pressure at the receptacle, and delivering fluid to a region where the receptacle is positioned, through a fluid outlet wherein the fluid outlet is coupled with a fluid source by a fluid channel that provides a fluid path between fluid source and the fluid outlet.

17. The apparatus as claimed in claim 16, wherein the fluid delivered through a fluid outlet is a liquid or a gas.

18. The apparatus as claimed in claim 10, wherein the controller is configured such that within any of the first suction operation session or the second suction operation session, the step of applying suction for generating negative pressure at the receptacle is followed by:

determining a first pressure at a location within a fluid path defined between the receptacle and a suction source;

responding to an absolute value of the first pressure being less than an absolute value of a predefined negative pressure threshold, by initiating fluid delivery from the fluid source and out of the fluid outlet through the fluid channels that provides a fluid path between the fluid source and the fluid outlet;

determining a second pressure at the location of the fluid path defined between the receptacle and the suction source, wherein the second pressure is determined after an elapse of a predefined tine interval from occurrence of a predefined event associated with initiated fluid delivery; and responding to determining that an absolute value of the second pressure is less than the absolute value of the predefined negative pressure threshold, by generating an error state alert.

19. A non-transitory computer usable medium having computer readable program code embodied therein for controlling an apparatus configured for removal of fecal material from a patient's rectum, wherein the apparatus includes a receptacle configured to be positioned at least partially at a patient's anorectal junction, a connecting tube comprising at least a suction channel, the connecting tube configured to couple the suction channel to a suction port of the receptacle, one or more sensors in communication with the receptacle, and a controller configured to apply a plurality of fecal removal cycles including applying suction through the suction port and by controlling a source of negative pressure to deliver suction so as to prevent buildup of fecal material within the rectum for the duration of the plurality of fecal removal cycles, the computer readable program code comprising instructions for implementing at a processor, the steps of:

responding to detection of a first suction operation session initiation event, by implementing a first suction operation session wherein implementation of the first suction operation session comprises:

applying suction for generating negative pressure at the receptacle;

responding to detection of a first suction operation session termination event by terminating the first suction operation session, and wherein terminating the first suction operation session comprises terminating application of suction for generating negative pressure at the receptacle;

implementing a next suction operation session in response to elapse of a predetermined time duration from termination of the first suction operation session, wherein implementation of the next suction operation session comprises:

applying suction for generating negative pressure at the receptacle; and responding to detection of a next suction operation session termination event by terminating the next suction operation session, and wherein terminating the next suction operation session comprises terminating application of suction for generating negative pressure at the receptacle;

wherein during the predetermined time duration between the termination of the first suction operation session and implementing of the next suction operation session, none of suction, irrigation or fluid movement is implemented within the apparatus and within the patient's rectum;

wherein triggering of pain signals from somatic nerves is avoided by positioning the receptacle at the patient's anorectal junction above the somatic nerve boundary at the anorectal junction, for the duration of the plurality of fecal removal cycles; and wherein the controller determines parameter(s) of one or more of the applied fecal removal cycles using sensor data received from the one or more sensors, wherein said sensor data indicates a condition within the patient's rectum.

* * * * *